United States Patent
Kim et al.

(10) Patent No.: US 9,271,969 B2
(45) Date of Patent: Mar. 1, 2016

(54) COMPOUNDS AS INHIBITORS OF DIACYLGLYCEROL O-ACYLTRANSFERASE TYPE 1 ENZYME

(71) Applicant: KAINOS MEDICINE, INC., Seoul (KR)

(72) Inventors: Dooseop Kim, Seoul (KR); Juhan Bok, Seoul (KR); Sunmi Shin, Gyeonggi-do (KR)

(73) Assignee: KAINOS MEDICINE, INC., Seoul (KR)

( * ) Notice: Subject to any disclaimer, the term of this patent is extended or adjusted under 35 U.S.C. 154(b) by 0 days.

(21) Appl. No.: 14/377,087

(22) PCT Filed: Feb. 6, 2013

(86) PCT No.: PCT/KR2013/000954
§ 371 (c)(1),
(2) Date: Aug. 6, 2014

(87) PCT Pub. No.: WO2013/119040
PCT Pub. Date: Aug. 15, 2013

(65) Prior Publication Data
US 2015/0157611 A1    Jun. 11, 2015

Related U.S. Application Data

(60) Provisional application No. 61/595,796, filed on Feb. 7, 2012.

(51) Int. Cl.

| A61K 31/44 | (2006.01) |
| C07D 471/02 | (2006.01) |
| A61K 31/437 | (2006.01) |
| C07D 471/04 | (2006.01) |
| A61K 31/429 | (2006.01) |
| C07D 513/04 | (2006.01) |
| A61K 45/06 | (2006.01) |

(52) U.S. Cl.
CPC .............. *A61K 31/437* (2013.01); *A61K 31/429* (2013.01); *A61K 45/06* (2013.01); *C07D 471/04* (2013.01); *C07D 513/04* (2013.01)

(58) Field of Classification Search
None
See application file for complete search history.

(56) References Cited

U.S. PATENT DOCUMENTS

| 2009/0209602 A1 | 8/2009 | Butlin et al. |
| 2009/0298853 A1 | 12/2009 | Bauer et al. |

FOREIGN PATENT DOCUMENTS

| CN | 101415683 A | 4/2009 |
| CN | 101460469 A | 6/2009 |
| CN | 101636155 A | 1/2010 |
| CN | 101772504 A | 7/2010 |
| CN | 101827842 A | 9/2010 |
| CN | 101932562 A | 12/2010 |
| JP | 2010-132590 A | 6/2010 |
| WO | WO2007/126957 | 11/2007 |
| WO | WO2008/067257 | 6/2008 |
| WO | WO 2009/016462 | 2/2009 |
| WO | WO 2009/024821 A2 | 2/2009 |
| WO | WO 2010/086820 A1 | 8/2010 |
| WO | WO 2010/107768 A1 | 9/2010 |

OTHER PUBLICATIONS

Silva, T. Mini Rev Med Chem 2005 vol. 5 pp. 893-914.*
International Search Report for Appl. No. PCT/KR2013/000954, mailed May 30, 2013.
Machine translation of JP 2010-132590; published Jun. 17, 2010.

* cited by examiner

*Primary Examiner* — Heidi Reese
(74) *Attorney, Agent, or Firm* — Cooley LLP

(57) ABSTRACT

The invention provides a novel compound having activity against diacylglycerol O-acyltransferase type 1 (DGAT1); a pharmaceutical composition for preventing or treating a disease, disorder or condition modulated by inhibition of DGAT1 comprising said compound; a method for preventing or treating a disease, disorder or condition modulated by inhibition of DGAT1 in an individual comprising administering said compound to the individual in need thereof; and a use of said compound for the manufacture of a medicament for preventing or treating a disease, disorder or condition modulated by DGAT1 inhibition.

9 Claims, No Drawings

COMPOUNDS AS INHIBITORS OF DIACYLGLYCEROL O-ACYLTRANSFERASE TYPE 1 ENZYME

This application is a U.S. national stage application of International Application No. PCT/KR2013/000954, which was filed on Feb. 6, 2013 and claims the benefit of priority to U.S. Provisional Application No. 61/595,796, which was filed on Feb. 7, 2012. The disclosures of each of these applications are hereby incorporated by references in its entirety for all purposes.

FIELD OF THE INVENTION

The present invention relates to a novel compound which inhibits diacylglycerol O-acyltransferase type 1 (DGAT1) activity; a preparation method thereof; a pharmaceutical composition for preventing or treating a disease, disorder or condition modulated by DGAT1 inhibition comprising said compound; a method for preventing or treating a disease, disorder or condition modulated by DGAT1 inhibition; and a use of said compound for the manufacture of a medicament for preventing or treating a disease, disorder or condition modulated by DGAT1 inhibition.

BACKGROUND OF THE INVENTION

Fatty acids are a key component of many human metabolic processes and are an important fuel source. Fatty acids are stored in multiple tissues, and often transported within the body in the form of triglycerides (triacylglycerols). Derangements in fatty acid and triglyceride metabolism are characteristic of obesity, type 2 diabetes, dyslipidemia, non-alcoholic fatty liver disease, metabolic syndrome, and other metabolic diseases. A key player in the conversion of fatty acids to triglycerides is the microsomal enzyme diacylglycerol O-acyltransferase 1 (DGAT1). DGAT1 catalyzes the final and only committed step in triglyceride synthesis. More specifically, DGAT1 couples a fatty acid Coenzyme A ester with 1,2-diacylglycerol to produce a triglyceride and Coenzyme A. There are two known DGAT enzymes types 1 and 2, but there is little homology between the two. DGAT1 activity can be detected in a number of mammalian tissues including intestine, liver and adipose. DGAT1 is a key component of triglyceride synthesis in multiple tissues, in the absorption of dietary triglycerides, and in the hepatic synthesis and secretion of triglyceride rich lipoproteins. DGAT1 activity may influence the release of intestinal peptides such as PeptideYY (PYY) and Glucagon-like peptide-1 (GLP-1) which play an important role in metabolic processes. The DGAT1 (−/−) knockout mouse is lean and resistant to high fat diet-induced obesity and insulin resistance. These animals have a higher metabolic rate and increased activity relative to wild type mice. The phenotype of the DGAT1 (−/−) animal suggests that DGAT1 inhibitors may be useful for the treatment of a number of metabolic diseases including type 2 diabetes and obesity.

Therefore, the present invention provides a novel compound having a medical utility including inhibition of DGAT1 activity, which can be useful in the prevention or treatment of a disease, disorder or condition modulated by DGAT1 inhibition, such as obesity-related disorders, type 2 diabetes, or diabetes-related disorders.

SUMMARY OF THE INVENTION

Therefore, it is an object of the present invention to provide a novel compound having a medical utility including inhibition of DGAT1 activity.

It is another object of the present invention to provide a pharmaceutical composition comprising said compound as an active ingredient.

It is a further object of the present invention to provide a method for preventing or treating a disease, disorder or condition modulated by DGAT1 inhibition in an individual comprising the step of administering said compound to the individual in need thereof.

It is a still further object of the present invention to provide a use of said compound for the manufacture of a medicament for preventing or treating a disease, disorder or condition modulated by DGAT1 inhibition.

In accordance with one aspect of the present invention, there is provided a compound of formula (IA), (IB) or (IC), or a pharmaceutically acceptable salt, solvate, ester or prodrug thereof:

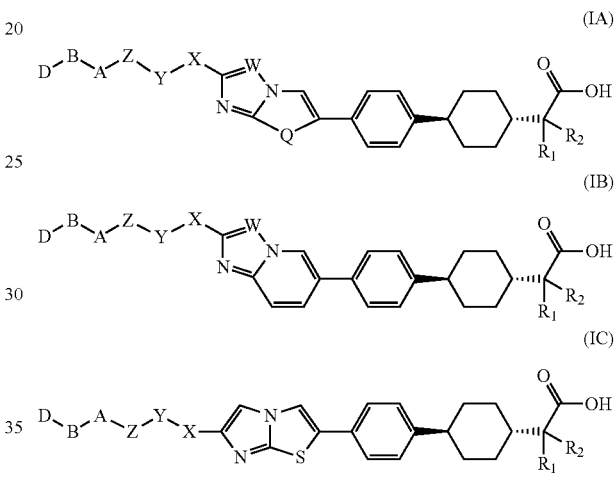

wherein,

Q is absent, S or —CH═CH—;
$R_1$ is H or $(C_1-C_3)$alkyl;
$R_2$ is H or $(C_1-C_3)$alkyl;
W is CH or N;
X is absent, O, $NR_3$, or $CR_4R_5$;
Y is C(O), C(S), S(O), $S(O)_2$, or $CR_4R_5$;
Z is absent, $NR_3$, O, or $CR_4R_5$;
A is absent, $(CR_4R_5)_m$, wherein m is an integer ranging from 1 to 4, —C(CH$_2$CH$_2$)—, C(O), S(O), or $S(O)_2$;
B is absent, $(CR_4R_5)_n$, wherein n is an integer ranging from 1 to 3, C(O), S(O), $S(O)_2$, O, or $NR_3$;
D is H, $(C_1-C_7)$alkyl, $(C_1-C_7)$alkoxy, $(C_1-C_7)$perfluoroalkoxy, $(C_1-C_7)$perfluoroalkyl, $NR_3R_6$, a $(C_6-C_{10})$aryl group (including but not limited to a phenyl group), a $(C_3-C_{10})$cycloalkyl, or a 3- to 11-membered heterocycle with 1 or 2 rings comprising 1 to 4 endocyclic hetero atoms selected from the group consisting of O, S, and N, wherein the aryl groups and the said heterocycle present in D are optionally substituted with one or more substituents chosen from a radical G; in which: G, when present, is selected from the group consisting of a halogen atom, hydroxyl group, nitro, cyano, amino, $(C_1-C_7)$alkyl, $(C_1-C_7)$perfluoroalkyl, $(C_1-C_7)$acyl, $(C_1-C_7)$perfluoroacyl, $(C_1-C_7)$perfluoroalkoxy, $CF_3CH_2O$—, $CF_3CH_2$—, $(C_1-C_7)$alkoxy, $(C_1-C_7)$alkylthio, $(C_1-C_7)$alkylsulfonyl, $(C_1-C_7)$alkylsulfinyl, phenyl, phenoxy, $(\{CH_2\}_p)C(O)OR_3$, $(\{CH_2\}_p)OC(O)R_7$, $(\{CH_2\}_p)NR_3R_6$, $(\{CH_2\}_pR_8)$, $(\{CH_2\}_p)C(O)NR_3R_6$, $(\{CH_2\}_p)C(O)R_8)$, $(\{CH_2\}_p)OC(O)NR_3R_6$, $(\{CH_2\}_p)OC$ (O)R$_8$), ({CH$_2$}$_p$)NR$_3$C(O)NR$_3$R$_6$, ({CH$_2$}$_p$)NR$_3$C(O)R$_8$, ({CH$_2$}$_p$)NR$_3$C(S)NR$_3$R$_6$, ({CH$_2$}$_p$)NR$_3$C(S)R$_8$, ({CH$_2$}$_p$)NR$_3$C(O)R$_3$, ({CH$_2$}$_p$)NR$_3$C(O)OR$_3$, ({CH$_2$}$_q$)OS(O)$_2$R$_7$, ({CH$_2$}$_q$)S(O)R$_7$, ({CH$_2$}$_p$)NR$_3$S(O)$_2$R$_7$, ({CH$_2$}$_p$)S(O)$_2$NR$_3$R$_6$, ({CH$_2$}$_p$)S(O)$_2$R$_8$, ({CH$_2$}$_p$)NR$_3$S(O)$_2$NR$_3$R$_6$, ({CH$_2$}$_p$)NR$_3$S(O)$_2$R$_8$, ({CH$_2$}$_p$)NR$_3$C(NR$_3$)NR$_3$R$_6$, ({CH$_2$}$_p$)R$_8$, and a combination thereof (with the proviso that when W is a phenyl or phenoxy, it may optionally be substituted with one or more substituents chosen from the radical G); in which:

R$_3$ is H, (C$_1$-C$_5$)alkyl or (C$_3$-C$_{10}$)cycloalkyl;

R$_4$ and R$_5$ being each independently hydrogen, or (C$_1$-C$_5$)alkyl;

R$_6$ is H, (C$_1$-C$_5$)alkyl or (C$_3$-C$_{10}$)cycloalkyl;

R$_7$ is (C$_1$-C$_5$)alkyl or (C$_3$-C$_{10}$)cycloalkyl;

R$_8$ is a 3- to 10-membered heterocycle with 1 or 2 rings comprising 1 to 4 endocyclic hetero atoms selected from the group consisting of O, S and N;

p is an integer ranging from 0 to 5; and q is an integer ranging from 1 to 5.

In accordance with another aspect of the present invention, there is provided a pharmaceutical composition for preventing or treating disease, disorder or condition modulated by DGAT1 inhibition, which comprises the compound of formula (IA), (IB) or (IC), or a pharmaceutically acceptable salt, solvate, ester or prodrug thereof.

In accordance with a further aspect of the present invention, there is provided a method for preventing or treating disease, disorder or condition modulated by DGAT1 inhibition in an individual comprising the step of administering the compound of formula (IA), (IB) or (IC), or its pharmaceutically acceptable salt, solvate, ester or prodrug to the individual in need thereof.

In accordance with a still further aspect of the present invention, there is provided a use of the compound of formula (IA), (IB) or (IC), or its pharmaceutically acceptable salt, solvate, ester or prodrug for the manufacture of a medicament for preventing or treating disease, disorder or condition modulated by DGAT1 inhibition.

DETAILED DESCRIPTION OF THE INVENTION

In another aspect, the present invention provides a compound of formula (ID), (IE) or (IF), or a pharmaceutically acceptable salt, solvate, ester or prodrug thereof:

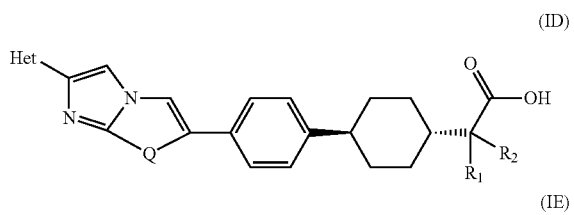

(ID)

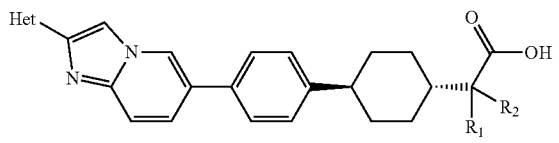

(IE)

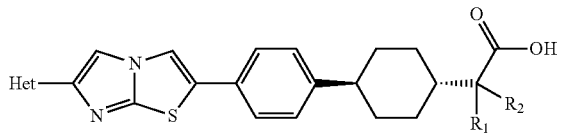

(IF)

wherein,

Q is S or CH=CH—;

R$_1$ is H or (C$_1$-C$_3$)alkyl;

R$_2$ is H or (C$_1$-C$_3$)alkyl; and

Het is a 3- to 11-membered heterocycle with 1 or 2 rings comprising 1 to 4 endocyclic hetero atoms selected from the group consisting of O, S and N, wherein said heterocycle is optionally substituted with one or more substituents chosen from a radical G defined in above.

Heterocycles that may be particularly suited for a compound of the invention having a formula selected from the group consisting of Formula (ID), Formula (IE), or Formula (IF), include but are not limited to pyrrole, imidazole, pyridine, triazole, tiazole, indole, benzimidazole, 3H-Imidazo[4,5-b]pyridine, 1H-Imidazo[4,5-b]pyrazine, 4(3H)-quinazolinone, 1,2,4-benzothiadiazine-1,1-dioxide, imidazo[1,2-a]pyridine, [1,2,4]triazolo[1,5-a]pyridine, imidazo[2,1-b]thiazole, preferably, imidazo[1,2-a]pyridine, [1,2,4]triazolo[1,5-a]pyridine, imidazo[2,1-b]thiazole.

Preferably, the present invention provides a compound of formula (IA), (IB) or (IC), wherein:

R$_1$ and R$_2$ being each independently hydrogen;

W is CH or N;

X is absent;

Y is C(O);

Z is absent or NH;

A is absent, (C$_1$-C$_3$)alkyl, —C(CH$_2$CH$_2$)—, CH(CH$_3$)— or C(CH$_3$)$_2$—;

B is absent, (C$_1$-C$_3$)alkyl, —C(CH$_2$CH$_2$)—, CH(CH$_3$)— or C(CH$_3$)$_2$—; and D is phenyl; phenyl substituted with one or more substituents chosen from a radical G selected from the group consisting of halogen, hydroxy, (C$_1$-C$_7$)alkyl, (C$_1$-C$_7$)alkoxy, CF$_3$CH$_2$O—, CF$_3$CH$_2$— and phenoxy substituted with halogen; benzo[d][1,3]dioxole; or 3,4-dihydro-2H-benzo[b][1,4]dioxepin.

Examples of more preferred compounds of formula (IA), (IB), (IC), (ID), (IE) or (IF) according to the present invention are:

1) 2-((1r,4r)-4-(4-(2-((4-(Trifluoromethoxy)benzyl)carbamoyl)imidazo[1,2-a]pyridin-6-yl)phenyl)cyclohexyl)acetic acid;
2) 2-((1r,4r)-4-(4-(2-((4-(Trifluoromethyl)phenyl)carbamoyl)imidazo[1,2-a]pyridin-6-yl)phenyl)-cyclohexyl)acetic acid;
3) 2-((1 r,4r)-4-(4-(2-((4-(Trifluoromethoxy)phenyl)carbamoyl)imidazo[1,2-a]pyridin-6-yl)-phenyl)cyclohexyl)acetic acid;
4) 2-((1r,4r)-4-(4-(2-((4-(Trifluoromethyl)benzyl)carbamoyl)imidazo[1,2-a]pyridin-6-yl)-phenyl)cyclohexyl)acetic acid;
5) 2-((1r,4r)-4-(4-(2-((3-(Trifluoromethoxy)phenyl)carbamoyl)imidazo[1,2-c]pyridin-6-yl)-phenyl)cyclohexyl)acetic acid;
6) 2-((1r,4r)-4-(4-(2-((3-(Trifluoromethyl)phenyl)carbamoyl)imidazo[1,2-a]pyridin-6-yl)-phenyl)cyclohexyl)acetic acid;

7) 2-((1r,4r)-4-(4-(2-((3-(Trifluoromethoxy)benzyl)carbamoyl)imidazo[1,2-a]pyridin-6-yl)-phenyl)cyclohexyl)acetic acid;
8) 2-((1r,4r)-4-(4-(2-((4-(tert-Butyl)benzyl)carbamoyl)imidazo[1,2-a]pyridin-6-yl)phenyl)-cyclohexyl)acetic acid;
9) 2-((1r,4r)-4-(4-(2-((2-Fluoro-5-(trifluoromethoxy)benzyl)carbamoyl)imidazo[1,2-a]pyridin-6-yl)phenyl)cyclohexyl)acetic acid;
10) 2-((1r,4r)-4-(4-(2-((4-Fluoro-3-(trifluoromethoxy)benzyl)carbamoyl)imidazo[1,2-a]pyridin-6-yl)phenyl)cyclohexyl)acetic acid;
11) 2-((1r,4r)-4-(4-(2-((3-Fluoro-4-(trifluoromethyl)benzyl)carbamoyl)imidazo[1,2-a]pyridin-6-yl)phenyl)cyclohexyl)acetic acid;
12) 2-((1r,4r)-4-(4-(2-((4-Methoxybenzyl)carbamoyl)imidazo[1,2-a]pyridin-6-yl)phenyl)cyclo-hexyl)acetic acid;
13) 2-((1r,4r)-4-(4-(2-((3-Chloro-4-fluorophenyl)carbamoyl)imidazo[1,2-a]pyridin-6-yl)-phenyl)cyclohexyl)acetic acid;
14) 2-((1r,4r)-4-(4-(2-((Benzo[d][1,3]dioxol-5-ylmethyl)carbamoyl)imidazo[1,2-a]pyridin-6-yl)phenyl)cyclohexyl)acetic acid;
15) 2-((1r,4r)-4-(4-(2-((3,4-Dichlorophenyl)carbamoyl)imidazo[1,2-a]pyridin-6-yl)phenyl)-cyclohexyl)acetic acid;
16) 2-((1r,4r)-4-(4-(2-((3-Chlorophenyl)carbamoyl)imidazo[1,2-a]pyridin-6-yl)phenyl)cyclo-hexyl)acetic acid;
17) 2-((1r,4r)-4-(4-(2-((3-Chloro-4-fluorobenzyl)carbamoyl)imidazo[1,2-a]pyridin-6-yl)-phenyl)cyclohexyl)acetic acid;
18) 2-((1r,4r)-4-(4-(2-((2-Methoxy-5-(trifluoromethoxy)benzyl)carbamoyl)imidazo[1,2-a]-pyridin-6-yl)phenyl)cyclohexyl)acetic acid;
19) 2-((1r,4r)-4-(4-(2-((4-Isopropylbenzyl)carbamoyl)imidazo[1,2-a]pyridin-6-yl)phenyl)cyclo-hexyl)acetic acid;
20) 2-((1r,4r)-4-(4-(2-((2-(4-Fluorophenyl)propan-2-yl)carbamoyl)imidazo[1,2-a]pyridin-6-yl)phenyl)cyclohexyl)acetic acid;
21) 2-((1r,4r)-4-(4-(2-((1-(2,5-Difluorophenyl)cyclopropyl)carbamoyl)imidazo[1,2-a]pyridin-6-yl)phenyl)cyclohexyl)acetic acid;
22) 2-((1r,4r)-4-(4-(2-((2-Chloro-6-methylbenzyl)carbamoyl)imidazo[1,2-a]pyridin-6-yl)-phenyl)cyclohexyl)acetic acid;
23) 2-((1r,4r)-4-(4-(2-((3,4-Dimethoxybenzyl)carbamoyl)imidazo[1,2-a]pyridin-6-yl)phenyl)-cyclohexyl)acetic acid;
24) (R,S)-2-((1r,4r)-4-(4-(2-((l-Phenylethyl)carbamoyl)imidazo[1,2-a]pyridin-6-yl)phenyl)cyclo-hexyl)acetic acid;
25) 2-((1r,4r)-4-(4-(2-((4-(4-Fluorophenoxy)benzyl)carbamoyl)imidazo[1,2-a]pyridin-6-yl)-phenyl)cyclohexyl)acetic acid;
26) 2-((1r,4r)-4-(4-(2-(((3,4-Dihydro-2H-benzo[b][1,4]dioxepin-7-yl)methyl)carbamoyl)-imidazo[1,2-a]pyridin-6-yl)phenyl)cyclohexyl)acetic acid;
27) 2-((1r,4r)-4-(4-(2-((2-Chloro-6-fluorobenzyl)carbamoyl)imidazo[1,2-a]pyridin-6-yl)-phenyl)cyclohexyl)acetic acid;
28) 2-((1r,4r)-4-(4-(2-((2,6-Dichlorobenzyl)carbamoyl)imidazo[1,2-a]pyridin-6-yl)phenyl)-cyclohexyl)acetic acid;
29) 2-((1r,4r)-4-(4-(2-((2,6-Difluorobenzyl)carbamoyl)imidazo[1,2-a]pyridin-6-yl)phenyl)cyclohexyl)acetic acid;
30) 2-((1r,4r)-4-(4-(2-((2-Chloro-6-(trifluoromethyl)benzyl)carbamoyl)imidazo[1,2-a]pyridin-6-yl)phenyl)cyclohexyl)acetic acid;
31) 2-((1r,4r)-4-(4-(2-(Benzylcarbamoyl)imidazo[1,2-a]pyridin-6-yl)phenyl)cyclohexyl)acetic acid;
32) 2-((1r,4r)-4-(4-(2-(o-Tolylcarbamoyl)imidazo[1,2-a]pyridin-6-yl)phenyl)cyclohexyl)acetic acid;
33) 2-((1r,4r)-4-(4-(2-((4-Fluoro-2-(trifluoromethyl)phenyl)carbamoyl)imidazo[1,2-a]pyridin-6-yl)phenyl)cyclohexyl)acetic acid;
34) 2-((1r,4r)-4-(4-(2-((2-(Trifluoromethyl)phenyl)carbamoyl)imidazo[1,2-a]pyridin-6-yl)phenyl)cyclohexyl)acetic acid;
35) 2-((1r,4r)-4-(4-(2-(2-Fluorophenyl)carbamoyl)imidazo[1,2-a]pyridin-6-yl)phenyl)cyclohexyl)acetic acid;
36) 2-((1r,4r)-4-(4-(2-((2-Methoxyphenyl)carbamoyl)imidazo[1,2-a]pyridin-6-yl)phenyl)cyclohexyl)acetic acid;
37) 2-((1r,4r)-4-(4-(2-((2-Methylbenzyl)carbamoyl)imidazo[1,2-a]pyridin-6-yl)phenyl)cyclohexyl)acetic acid;
38) 2-((1r,4r)-4-(4-(2-((2,6-Dimethylphenyl)carbamoyl)imidazo[1,2-a]pyridin-6-yl)phenyl)cyclohexyl)acetic acid;
39) 2-((1r,4r)-4-(4-(2-((2,5-Difluorophenyl)carbamoyl)imidazo[1,2-a]pyridin-6-yl)phenyl)cyclohexyl)acetic acid;
40) 2-((1r,4r)-4-(4-(2-((3,4,5-Trifluorophenyl)carbamoyl)imidazo[1,2-a]pyridin-6-yl)phenyl)cyclohexyl)acetic acid;
41) 2-((1r,4r)-4-(4-(2-((2-Methoxybenzyl)carbamoyl)imidazo[1,2-a]pyridin-6-yl)phenyl)cyclohexyl)acetic acid;
42) 2-((1s,4s)-4-(4-(2-(4-chloro-2,6-difluorobenzyl)carbamoyl)imidazo[1,2-a]pyridin-6-yl)phenyl)cyclohexyl)acetic acid;
43) 2-((1 s,4s)-4-(4-(2-((2,4-Dichloro-6-methylbenzyl)carbamoyl)imidazo[1,2-a]pyridin-6-yl)phenyl)cyclohexyl)acetic acid;
44) 2-((1s,4s)-4-(4-(2-((2,4,6-Trimethylbenzyl)carbamoyl)imidazo[1,2-a]pyridin-6-yl)phenyl)cyclohexyl)acetic acid;
45) 2-((1s,4s)-4-(4-(2-(4-Methylbenzyl)carbamoyl)-[1,2,4]triazolo[1,5-a]pyridin-6-yl)phenyl)cyclohexyl)acetic acid;
46) 2-((1r,4r)-4-(4-(6-((4-(tert-Butyl)benzyl)carbamoyl)imidazo[2,1-b]thiazol-2-yl)phenyl)-cyclohexyl)acetic acid;
47) 2-((1r,4r)-4-(4-(6-((3-Chlorophenyl)carbamoyl)imidazo[2,1-b]thiazol-2-yl)phenyl)cyclo-hexyl)acetic acid;
48) 2-((1r,4r)-4-(4-(6-((3-Chloro-4-(trifluoromethoxy)benzyl)carbamoyl)imidazo[2,1-b]thiazol-2-yl)phenyl)cyclohexyl)acetic acid;
49) 2-((1r,4r)-4-(4-(6-((3-Chloro-4-fluorobenzyl)carbamoyl)imidazo[2,1-b]thiazol-2-yl)phenyl)-cyclohexyl)acetic acid;
50) 2-((1r,4r)-4-(4-(6-((3-(Trifluoromethoxy)benzyl)carbamoyl)imidazo[2,1-b]thiazol-2-yl)-phenyl)cyclohexyl)acetic acid;
51) 2-((1r,4r)-4-(4-(6-((2-Fluoro-5-(trifluoromethoxy)benzyl)carbamoyl)imidazo[2,1-b]thiazol-2-yl)phenyl)cyclohexyl)acetic acid;
52) 2-((1r,4r)-4-(4-(6-((3-(Trifluoromethoxy)phenyl)carbamoyl)imidazo[2,1-b]thiazol-2-yl)-phenyl)cyclohexyl)acetic acid;
53) 2-((1r,4r)-4-(4-(6-((4-Isopropylbenzyl)carbamoyl)imidazo[2,1-b]thiazol-2-yl)phenyl)cyclohexyl)acetic acid;
54) 2-((1r,4r)-4-(4-(6-((1-(2,5-Difluorophenyl)cyclopropyl)carbamoyl)imidazo[2,1-b]thiazol-2-yl)phenyl)cyclohexyl)acetic acid;
55) 2-((1r,4r)-4-(4-(6-((2-Methoxy-5-(trifluoromethoxy)benzyl)carbamoyl)imidazo[2,1-b]-thiazol-2-yl)phenyl)cyclohexyl)acetic acid;
56) 2-((1r,4r)-4-(4-(6-((4-(Trifluoromethoxy)benzyl)carbamoyl)imidazo[2,1-b]thiazol-2-yl)-phenyl)cyclohexyl)acetic acid;
57) 2-((1r,4r)-4-(4-(6-((4-Methoxybenzyl)carbamoyl)imidazo[2,1-b]thiazol-2-yl)phenyl)cyclo-hexyl)acetic acid;

58) 2-((1r,4r)-4-(4-(6-((Benzo[d][1,3]dioxol-5-ylmethyl) carbamoyl)imidazo[2,1-b]thiazol-2-yl)-phenyl)cyclohexyl)acetic acid;
59) 2-((1r,4r)-4-(4-(6-((4-Fluoro-3-(trifluoromethoxy)benzyl)carbamoyl)imidazo[2,1-b]thiazol-2-yl)phenyl)cyclohexyl)acetic acid;
60) 2-((1r,4r)-4-(4-(6-((3-Chloro-4-fluorophenyl)carbamoyl)imidazo[2,1-b]thiazol-2-yl)-phenyl)cyclohexyl)acetic acid;
61) 2-((1r,4r)-4-(4-(6-((2,6-dichlorobenzyl)carbamoyl)imidazo[2,1-b]thiazol-2-yl)phenyl)cyclohexyl)acetic acid;
62) 2-((1r,4r)-4-(4-(6-((2-chloro-6-fluorobenzyl)carbamoyl) imidazo[2,1-b]thiazol-2-yl)phenyl)cyclohexyl)acetic acid;
63) 2-((1-(4-(6-((2,6-difluorobenzyl)carbamoyl)imidazo[2,1-b]thiazol-2-yl)phenyl)cyclohexyl)acetic acid;
64) 2-((1r,4r)-4-(4-(6-((4-chloro-2,6-difluorobenzyl)carbamoyl)imidazo[2,1-b]thiazol-2-yl)phenyl)cyclohexyl) acetic acid;
65) 2-((1r,4r)-4-(4-(2-(Benzylcarbamoyl)imidazo[1,2-a]pyridin-6-yl)phenyl)cyclohexyl)-2-methylpropanoic acid;
66) 2-Methyl-2-((1r,4r)-4-(4-(2-((4-(trifluoromethoxy)benzyl)carbamoyl)imidazo[1,2-a]pyridin-6-yl)phenyl)cyclohexyl)propanoic acid; and
67) 2-((1s,4s)-4-(4-(2-((2-Chloro-6-methylbenzyl)carbamoyl)imidazo[1,2-a]pyridin-6-yl)phenyl)cyclohexyl)-2-methylpropanoic acid.

Also, the present invention provides a pharmaceutical composition for preventing or treating disease, disorder or condition modulated by DGAT1 inhibition, which comprises the compound of any one of formulas (IA) to (IF), or a pharmaceutically acceptable salt, solvate, ester or prodrug thereof as an active ingredient.

The pharmaceutical composition of the present invention can ameliorate, prevent, treat or inhibit the disease, disorder, or condition that needs modulation of DGAT1, such as obesity; obesity-related disorders such as type 2 diabetes, heart disease associated with increased triglyceride levels, hypertension, metabolic syndrome (also known as "Syndrome X"), polycystic ovary syndrome and dyslipidemia; complications associated with type 2 diabetes such as angina, atherosclerosis, high blood pressure, neuropathy, nephropathy, diabetic retinopathy, skin ulcers, osteoporosis, vascular dementia and hearing impairment; and non-alcoholic fatty liver disease.

The pharmaceutical composition of the present invention may comprise the compound of the present invention in a medically effective amount (e.g., therapeutically effective amount, or prophylactically effective amount), and a pharmaceutically acceptable carrier.

The pharmaceutical composition of the present invention provides enhanced DGAT1 activity-inhibiting effects when combined with another pharmaceutical agent selected from the group consisting of an anti-obesity agent, an anti-diabetic agent, an anti-dyslipidemia agent, and an anti-hypertensive agent in a medically effective amount.

Also, the present invention further provides a method for preventing or treating a disease, disorder or condition modulated by DGAT1 inhibition in an individual comprising the step of administering the compound of any one of formulas (IA) to (IF), or its pharmaceutically acceptable salt, solvate, ester or prodrug to the individual in need thereof.

Furthermore, the present invention provides a method for inhibiting DGAT1 activity by administering to an individual in need of modulation by DGAT1 inhibition.

In the inventive methods, said individual may be a mammal such as a human.

In the inventive method, one or more compounds of the present invention may be administered in a medically effective amount as the sole pharmaceutical agent, or may be administered in combination therapy with a medically effective amount of at least one additional pharmaceutical agent.

Such combination therapy may comprise the step of administering (a) a single pharmaceutical composition comprised of the compound of the present invention, at least one additional pharmaceutical agent, and a pharmaceutically acceptable carrier; or (b) two separate pharmaceutical compositions, which can be administered simultaneously or sequentially, comprising a first composition comprising a compound of the present invention and a pharmaceutically acceptable carrier; and a second composition comprising at least one additional pharmaceutical agent and a pharmaceutically acceptable carrier.

Preferably, the combination therapy may comprise the step of administering a medically effective amount of two pharmaceutical compositions comprising (i) a first composition comprising the compound of the present invention and a pharmaceutically acceptable carrier; and (ii) a second composition comprising at least one additional pharmaceutical agent selected from the group consisting of an anti-obesity agent, an anti-diabetic agent, an anti-dyslipidemia agent, and anti-hypertensive agent to the individual in need thereof.

In this method, the first composition and second composition may be administered simultaneously; or may be administered sequentially and in any order.

The present invention further provides a use of a compound of any one of formulas (IA) to (IF), or a pharmaceutically acceptable salt, solvate, ester or prodrug thereof, for the manufacture of a medicament for preventing or treating a disease, disorder or condition modulated by DGAT1 inhibition.

Other aspects, objects and features of the invention will be apparent from the following description.

While the terms used in the description of the invention are believed to be well understood by one of ordinary skill in the pharmaceutical arts, definitions, where provided herein, are set forth to facilitate description of the invention, and to provide illustrative examples for use of the terms.

The terms "a," "an," and "the" may mean one or more, and may be used to reference both the singular and the plural.

The terms "first" and "second" are used herein for purposes of distinguishing between two compounds, or between two compositions, as will be clearer from the description.

The phrase "medically effective amount" as used herein, refers to an amount of a composition or compound to treat the particular disease, condition or disorder; to ameliorate, relieve, or decrease one or more symptoms associated with the particular disease, condition or disorder; and/or to delay or prevent the onset of symptoms or a pathological process associated with the particular disease, condition or disorder described herein.

The term "pharmaceutically acceptable carrier" as used herein, refers to any compound, composition or carrier medium useful in any one or more of administration, delivery, storage, stability of a compound or composition described herein. These carriers known in the art may include, but are not limited to, a diluent, water, a saline, a suitable vehicle (e.g., liposome, microparticle, nanoparticle, emulsion and capsule), a buffer, a medical parenteral vehicle, an excipient, an aqueous solution, a suspension, a solvent, an emulsions, a detergent, a chelating agent, a solubilizing agent, a salt, a colorant, a polymer, a hydrogel, a surfactant, an emulsifier, an adjuvant, a filler, a preservative, a stabilizer, an oil, a binder, a disintegrant, an absorbant, a flavor agent, and the like as broadly known in the pharmaceutical art.

Prodrugs of the compounds according to the present invention are included within the scope of the invention. The term "prodrug" as used herein, refers to a compound that is transformed in vivo (e.g., by a metabolic, physiological, or chemical process) to yield a compounds of any one of formulas (IA) to (IF), or a pharmaceutically acceptable salt, hydrate or solvate thereof. Various forms of prodrugs are known in the art. Examples of prodrugs of the compounds according to the present invention may include an in vivo cleavable ester of a carboxy group (e.g., lower alkyl esters, cycloalkyl esters, lower alkenyl esters, benzyl esters, mono- or di-substituted lower alkyl esters, and the like); or S-acyl and O-acyl derivatives of thiols, alcohols or phenols.

The term "purified" or "isolated" for a compound refers to the physical state of the compound following isolation from a synthetic process or purification step described herein or well known to those in the art, and in sufficient purity to be characterizable by standard analytical methods described herein or well known in the art.

The terms "treat," "treats" or "treating," as used herein, refers to embrace one or more of preventative (prophylactically) or therapeutically (palliatively).

The compounds of any one of formulas (IA) to (IF) in the present invention can form salts, and therefore the pharmaceutically acceptable salt of the compounds may be included within the scope of the invention.

The terms "salt" or "pharmaceutically acceptable salt", as used herein, refers to inorganic or organic salts of a compound. These salts can be prepared, for example, by reacting a compound of any one of formulas (IA) to (IF) with an amount of acid or base, such as an equivalent amount, and in a medium such as one in which the salt formed then precipitates, or in an aqueous medium followed by lyophilization. Representative salts may include bisulfate, sulfate, benzene sulfonate, camphorsulfonate, laurylsulphonate, methanesulfonate, naphthalenesulformate, toluenesulfonate, acetate, trifluoracetate, benzoate, borate, butyrate, citrate, formate, fumarate, hydorbromide, hydrochloride, hydroiodide, lactate, laurate, maleate, malonate, mesylate, nitrate, oxalate, phosphate, hexafluorophosphate, propionate, salicylate, stearate, succinate, tartrate, thiocyanate, and the like. Also, the salts may include base salts based on the alkali and alkaline earth metals, such as calcium, sodium, lithium, magnesium, and potassium; or with organic bases such as with organic amines (e.g., dicyclohexylamine, t-butyl amine, methylamine, dimethylamine, triethylamine, ethylamine, procaine, morpholine, N-methylpiperidine, dibenzylamine, and the like); or as an ammonium salt.

The inventive compounds may exist in a solvated form or unsolvated form. Solvates of the inventive compounds may be formed in the synthetic process in which the compound becomes physically associated with one or more solvent molecules (e.g., such as by ionic and/or covalent bonding) or, optionally, may be converted to a solvate such as by dissolving the compound in desired amounts of a solvent of choice (e.g., organic solvent, water, or mixtures thereof) in forming a solution, heating the solution to a temperature higher that ambient temperature, and cooling the solution at a rate sufficient to form crystals of the solvate, which may then be further isolated using methods known the art. Examples of suitable solvents include methanolates, ethanolates, hydrates (where the solvent molecule is water), and the like.

The inventive compounds may contain asymmetric or chiral centers, and thus exist in different stereoisomeric forms. All stereoisomers (e.g., geometric isomers, optical isomers, and the like), enantiomeric forms, diastereomeric forms, tautomeric forms, positional isomers of the inventive compounds are embraced within the scope of the invention. A first conformational form of a compound can be separated from a second and different conformational form of the compound using methods well known in the chemical arts such as by chromatography, crystallization and synthetic methods which selectively result in a particular desired conformational form.

The pharmaceutical composition according to the present invention may be administered once, or multiple times, as needed, to deliver a medically effective amount of the composition, e.g., an amount effective to mediate modulation of a disease, disorder or condition by inhibiting DGAT1 in the individual receiving the pharmaceutical composition.

For example, a medically effective amount of the pharmaceutical composition comprising the inventive compound may be an amount that enters into cells which are contacted with the compound, and which results in inhibition of DGAT1 activity within the cells. Such a medically effective amount of the pharmaceutical composition will depend on such factors as the mode of administration, the formulation for administration, disease to be modulated, the size and health of the individual to receive such a pharmaceutical composition, and other factors which can be taken into consideration by a medical practitioner whom is skilled in the art of determining appropriate dosages for treatment. The amount of the inventive compounds in a composition to be administered may vary from about 0.01 mg to about 500 mg, and more typically from about 1 mg to about 200 mg per day. One skilled in the art can apply known principles and models of drug delivery and pharmacokinetics to ascertain a likely range of dosages to be tested in preclinical and clinical studies for determining a medically effective amount of the compound of the present invention.

In the present invention, the pharmaceutically acceptable carrier may facilitate one or more of storage, stability, administration and delivery of the pharmaceutical composition. The carrier may be particulate, so that the composition may be in, for example, powder or solid form. The carrier may be in a semi-solid, gel, or liquid formula, so that the composition may be ingested, injected, applied, or otherwise administered. The carrier may be gaseous, so that the composition may be inhaled.

For oral administration of the inventive pharmaceutical composition, suitable oral formulations may be presented in the form of tablets, caplets, capsules, and the like, in which typically the compound of the present invention may be present in a predetermined amount as a powder, granules, solution, or suspension as the sole active agent, or in combination with an additional one or more pharmaceutical agents.

As known in the art, such oral formulations typically include the pharmaceutically acceptable carrier selected from the group consisting of a binder (e.g., syrup, sorbitol, gum, corn starch, gelatin, acacia and the like), a filler (e.g., lactose, sugar, starch, calcium phosphate and the like), an excipient (e.g., dicalcium phosphate and the like), a disintegrating agent (e.g., vegetable starch, alginic acid and the like), a lubricant (e.g., magnesium stearate and the like), a flavoring agent (e.g., sweetening agent, natural or artificial flavors and the like) and a mixture thereof.

Such oral formulations may be coated or uncoated to modify their disintegration and/or absorption. Coating process may be performed using conventional coating agents and methods known in the art.

The mode of administration of a compound or composition of the present invention to an individual (such as a human) in need of such compound or composition may be any mode known in the art to be suitable for delivering a pharmaceutical composition, and particularly suitable for treating a disease, disorder or condition which can be modulated by DGAT1 inhibition. The mode may include, but is not limited to, intravenously, intraperitoneally, orally, subcutaneously, intramuscularly, intranasally, transdermally, by perfusion, and by peristaltic techniques.

The compositions for inhibiting DGAT1 activity according to the present invention may also be combined with other therapies to treat a disease, disorder or condition modulated by DGAT1 inhibition. Such combination therapy may be administered in concurrently, sequentially, or in regimen alternating between the composition of the present invention and the other therapy.

Such combination therapies may include the following treatments (or pharmaceutical agents, therapeutic agents):

(a) anti-obesity agents [e.g., orlistat, sibutramine, lorcaserin, a combination of bupropion and naltrexone, a combination of phentermine and topiramate, adipotide, rimonabant and the like];

(b) anti-diabetic agents [e.g., insulin; insulin derivatives; insulin mimetics; insulin sensitizing agents (including peroxisome proliferating-activator receptor (PPAR) gamma agonists, such as pioglitazone, rosiglitazone and the like); insulin secretagogues (including sulfonylureas, such as glipizide, glibenclamide, glyburide and amaryl); metformin; dipeptidyl peptidase W inhibitors (e.g., sitagliptin and vildagliptin); glucagon like peptide-1 and analogs and mimetics thereof; alphaglucosidase inhibitors (e.g., acarbose); sodium glucose co-transporter 2 (SGLT-2) inhibitors (e.g., dapagliflozen); and the like];

(c) anti-dyslipidemia agents [e.g., 3-hydroxy-3-methyl-glutaryl coenzyme A reductase inhibitors such as statins; cholestyramine; nicotinic acid; niacin; exetimibe; aspirin; and plant stanols]; and (d) anti-hypertensive agents [e.g., β-blockers (e.g., Inderal and atenolol); angiotensin converting enzyme inhibitors (e.g., benazepril, captopril, fosinopril and the like); diuretics (e.g., furosemide, torsemide, and ethacrynic acid); Na-K-ATP membrane pump inhibitors (e.g., digoxin); calcium antagonists or channel blockers (e.g., nifedipine, nicardipine, amlodipine, verapamil and the like); angiotensin II antagonists (e.g., candesartan, eprosartan, irbesartan, valsartan); renin inhibitors (e.g., zankiren, aliskiren); and β-adrenergic receptor blockers (e.g., nadolol, propanolol, atenolol, bisprolol and the like)].

The structure of therapeutic agents identified herein by code numbers and pharmaceutical company's initials, and their generic or trademark names, are readily available to those skilled in the art, such as from the standard compendium of drugs (e.g., The Merck Index) or from the applicable pharmaceutical company's web site, as well as dosages applicable for treatment (see also The Physician's Desk Reference). Alternatively, the doses and dosage regimen of a pharmaceutical agent, used in conjunction with a compound of the invention in combination therapy, can be determined by a physician, taking into account the medical literature, the health, age and sex of the patient, the disease or condition or disorder to be treated, the mode of administration and dosing schedule of the pharmaceutical agent, and other relevant considerations. Generally, dosages of such agents can range from about 0.1 mg to 1000 mg per day, with more specific dosages dependent on the aforementioned factors.

Accordingly, provided herein is a pharmaceutical composition comprising a medically effective amount of the inventive compound in combination with a medically effective amount of one or more therapeutic agent selected from the group consisting of an anti-obesity agent, an anti-diabetic agent, an anti-dyslipidemia agent and an anti-hypertensive agent; and optionally further comprising a pharmaceutically acceptable carrier.

General Methods of Synthesis

The general methods for preparing the compounds according to the present invention are illustrated in the following Schemes 1 to 5.

As shown in Scheme 1, the compound of formula A can be prepared from substituted heterocyclic intermediates such as the compound of formula B and pinacol boronate intermediates such as the compound of formula C using a standard palladium coupling reactions followed by hydrolysis.

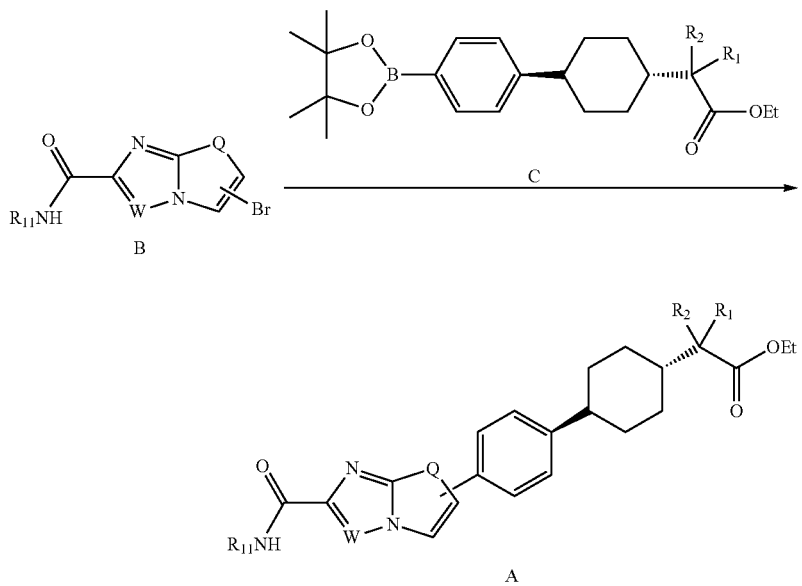

wherein, $R_{11}$ is H, ($C_1$-$C_7$)alkyl, ($C_1$-$C_7$)alkoxy, ($C_1$-$C_7$)perfluoroalkoxy, ($C_1$-$C_7$)perfluoroalkyl, $NR_3R_6$, a ($C_6$-$C_{10}$)aryl group (including but not limited to a phenyl group), a ($C_3$-$C_{10}$) cycloalkyl, or a 3- to 11-membered heterocycle with 1 or 2 rings comprising 1 to 4 endocyclic hetero atoms selected from the group consisting of O, S, and N, wherein the aryl groups and the said heterocycle present in $R_{11}$ are optionally substituted with one or more substituents chosen from a radical G; in which: G, when present, is selected from the group consisting of a halogen atom, hydroxyl group, nitro, cyano, amino, ($C_1$-$C_7$)alkyl, ($C_1$-$C_7$) perfluoroalkyl, ($C_1$-$C_7$)acyl, ($C_1$-$C_7$)perfluoroacyl, ($C_1$-$C_7$) perfluoroalkoxy, $CF_3CH_2O$—, $CF_3CH_2$—, ($C_1$-$C_7$)alkoxy, ($C_1$-$C_7$)alkylthio, ($C_1$-$C_7$)alkylsulfonyl, ($C_1$-$C_7$)alkylsulfinyl, phenyl, phenoxy, $(\{CH_2\}_p)C(O)OR_3$, $(\{CH_2\}_p)OC(O)R_7$, $(\{CH_2\}_p)NR_3R_6$, $(\{CH_2\}_p R_8)$, $(\{CH_2\}_p)C(O)NR_3R_6$, $(\{CH_2\}_p)C(O)R_8)$, $(\{CH_2\}_p)OC(O)NR_3R_6$, $(\{CH_2\}_p)OC(O)R_8)$, $(\{CH_2\}_p)NR_3C(O)NR_3R_6$, $(\{CH_2\}_p)NR_3C(O)R_8$, $(\{CH_2\}_p)NR_3C(S)NR_3R_6$, $(\{CH_2\}_p)NR_3C(S)R_8$, $(\{CH_2\}_p)NR_3C(O)R_3$, $(\{CH_2\}_p)NR_3C(O)OR_3$, $(\{CH_2\}_p)S(O)_2R_7$, $(\{CH_2\}_q)S(O)R_7$, $(\{CH_2\}_p)NR_3S(O)_2R_7$, $(\{CH_2\}_p)S(O)_2NR_3R_6$, $(\{CH_2\}_p)S(O)_2R_8$, $(\{CH_2\}_p)NR_3S(O)_2NR_3R_6$, $(\{CH_2\}_p)NR_3S(O)_2R_8$, $(\{CH_2\}_p)NR_3C(NR_3)NR_3R_6$, $(\{CH_2\}_p)R_8$, and a combination thereof (with the proviso that when G is a phenyl or phenoxy, it may optionally be substituted with one or more substituents chosen from the radical G); and $R_1$, $R_2$, W and Q have the same meanings as defined in formula (IA).

The preparation of the compounds of formulas B and C is described in the following schemes.

The compound of formula B is commercially available or may be conveniently prepared by a variety of methods familiar to those skilled in the art. One common route is shown in Scheme 2.

The compound of formula D as a starting material in a solvent such as dichloromethane may be treated with $Me_3Al$ solution in a solvent such as toluene at 0° C. The mixture thus obtained may be treated with amino derivative of formula E in a solvent such as dichloromethane followed by acid such as 1N HCl, to prepare an intermediate of formula F.

Scheme 2

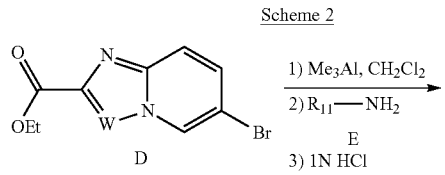

wherein, $R_{11}$ and W have same meanings as defined in above.

The compound of formula H is commercially available or may be conveniently prepared by a variety of methods familiar to those skilled in the art. One common route is shown in Scheme 3.

A compound of formula G may be subjected to a coupling reaction with a compound of formula E under a standard peptide coupling conditions.

For example, the peptide coupling reaction may be conducted using 1-ethyl-3-(3-dimethylaminopropyl)carbodiimide (EDC), 1-hydroxybenzotriazole (HOBT), in the presence of a base such as diisopropylethylamine (DIPEA), in a solvent such as N,N-dimethylformamide (DMF) or dichloromethane, for 8 to 16 hours at ambient temperature to prepare a compound of formula H.

Scheme 3

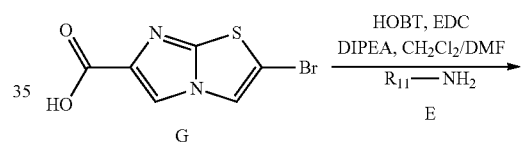

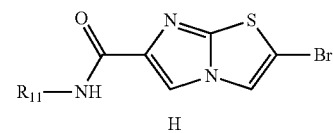

wherein, $R_{11}$ has same meanings as defined in above.

The compound of formula C is commercially available or may be conveniently prepared by a variety of methods familiar to those skilled in the art. One common route is shown in Scheme 4.

Scheme 4

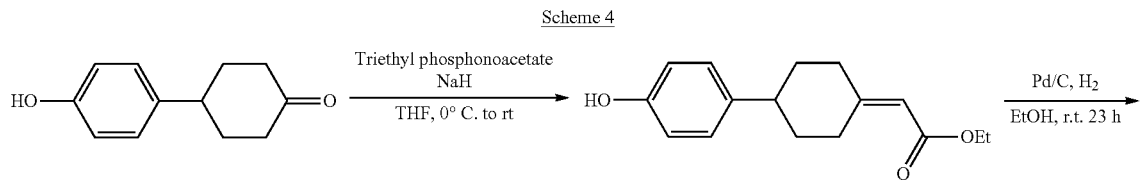

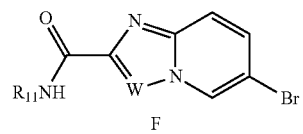

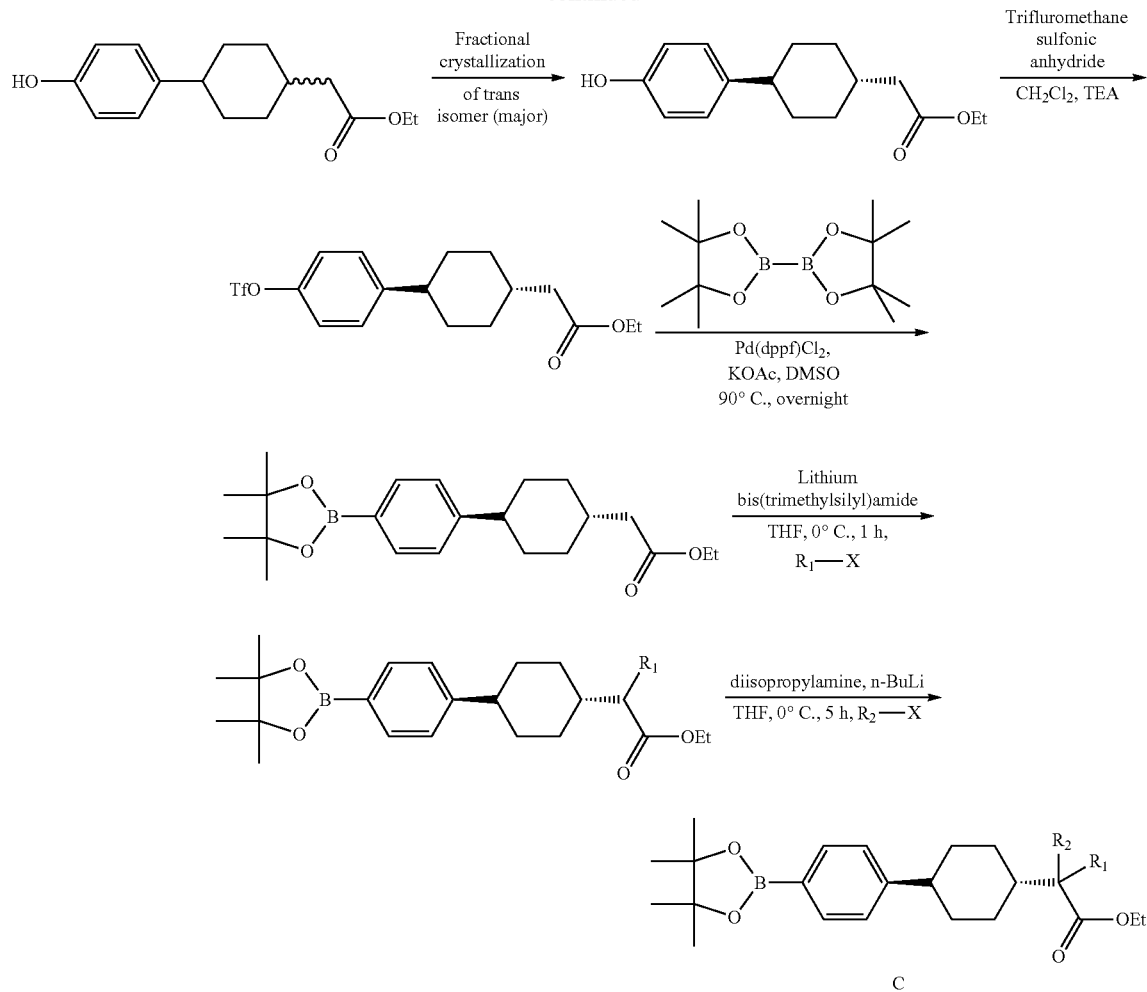

wherein,

R$_1$ and R$_2$ have the same meanings as defined in above.

Finally, the compound of formula A may be prepared by procedures shown in Scheme 5.

The compound of formula B may be subjected to a coupling reaction with the compound of formula C under a palladium coupling conditions. In this reaction, the palladium coupling reaction may be conducted using [1,1'-bis(diphenylphosphino)ferrocene]dichloropalladium(II) (Pd(dppf) Cl$_2$), potassium phosphate tribasic (K$_3$PO$_4$), in a mixed solvent of 1,4-dioxane and H$_2$O for 16 to 24 hours at elevated temperature to prepare a compound of formula J.

The ester compound of formula J may be then hydrolyzed using aqueous sodium hydroxide (NaOH) or lithium hydroxide (LiOH), in a mixed solvent of tetrahydrofuran (THF), methanol (MeOH) and H$_2$O. A mixture thus obtained may be treated with an acid solution such as an aqueous 1N hydrochloric acid, to prepare the desired compound of formula A.

Scheme 5

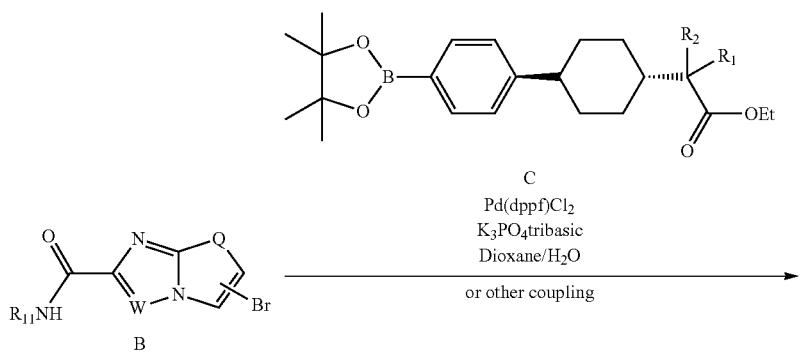

-continued

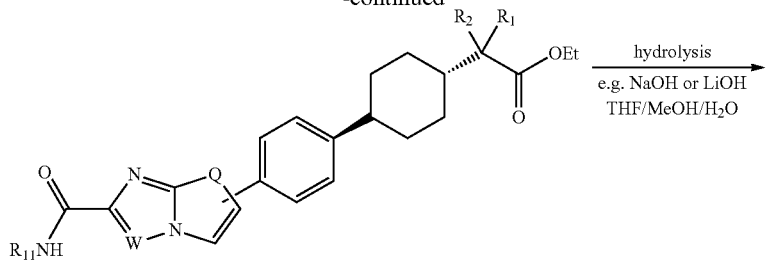

D

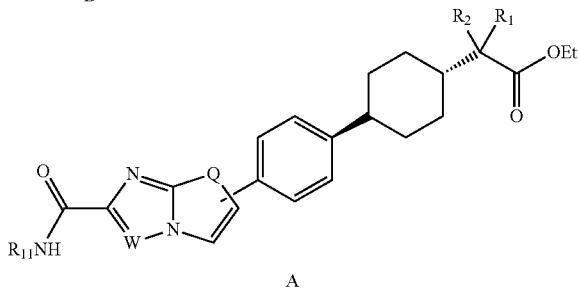

A wherein, $R_1$, $R_2$, $R_{11}$, W and Q have the same meanings as defined in above.

The order of carrying out the foregoing reaction schemes may be varied to facilitate the reaction or to avoid unwanted reaction products.

The following examples are provided so that the invention might be more fully understood. These examples are illustrative only and should not be construed as limiting the invention in any way.

EXAMPLES

The following examples are for illustrative purposes. Each exemplified compound represents a particular aspect of the compound according to the present invention. The compounds of formulas (IA) to (IF), and intermediate compounds used in their formation, may be synthesized by synthetic processes analogous to those well known in the chemical arts, particularly in light of the descriptions contained herein.

The starting materials are generally available from commercial sources, or are readily prepared using methods well known in the chemical arts.

Preparation of Intermediates

Illustrated are intermediate compounds, and their synthesis, useful for synthesizing the compounds of formulas (IA) to (IF).

Intermediate I

6-Bromo-N-(4-(trifluoromethoxy)benzyl)imidazo[1,2-a]pyridine-2-carboxamide

Me$_3$Al (2.0M solution in toluene) (2.78 ml, 5.57 mmol) was added to a solution of ethyl 6-bromoimidazo[1,2-a]pyridine-2-carboxylate (500 mg, 1.85 mmol) in methylene chloride (10 ml) at 0° C. The reaction mixture was stirred at room temperature for 2 hours. (4-(trifluoromethoxy)phenyl)methanamine (0.42 ml, 2.78 mmol) was added to the above mixture at room temperature. The reaction mixture was stirred at 50° C. for 20 hours. After cooling to room temperature, the reaction was quenched by 1N HCl solution (2-3 mL). The reaction mixture was partitioned between methylene chloride and water. The aqueous layer was extracted with methylene chloride. The combined organic layer was washed with brine, then dried over anhydrous magnesium sulfate. After concentration, the residue was purified by flash chromatography (ethyl acetate:hexane=1:1) to give the title compound, 6-bromo-N-(4-(trifluoromethoxy)-benzyl)imidazo[1,2-a]pyridine-2-carboxamide, as a solid (440 mg, 57% yield).

$^1$H NMR (400 MHz, CDCl$_3$) δ 8.30 (s, 1H), 8.13 (s, 1H), 7.70 (t, 1H), 7.43 (dd, 1H), 7.39 (d, 2H), 7.30 (dd, 1H), 7.18 (d, 2H), 4.16 (d, 2H). MS 413.9, 415.9, (M+1)$^+$.

Intermediate II

6-Bromo-N-(4-(trifluoromethy)phenyl)imidazo[1,2-a]pyridine-2-carboxamide

The title compound was prepared by essentially following the same procedures described for Intermediate I, using 4-(trifluoromethyl)aniline and ethyl 6-bromoimidazo[1,2-a]pyridine-2-carboxylate as starting materials.

$^1$H NMR (400 MHz, CDCl$_3$) δ 8.31 (s, 1H), 8.12 (d, 1H), 7.68 (brs, 1H), 7.39 (dd, 2H), 7.25 (d, 1H), 7.17 (d, 2H), 5.29 (d, 2H). MS 383.6, 385.7 (M+1)$^+$.

Intermediate III

6-Bromo-N-(4-(trifluoromethoxy)phenyl)imidazo[1,2-a]pyridine-2-carboxamide

The title compound was prepared by essentially following the same procedures described for Intermediate I, using 4-(trifluoromethoxy)aniline and ethyl 6-bromoimidazo[1,2-a]pyridine-2-carboxylate as starting materials.

$^1$H NMR (400 MHz, CDCl$_3$) δ 9.21 (s, 1H), 8.34 (s, 1H), 8.17 (s, 1H), 7.77 (d, 2H), 7.50 (d, 1H), 7.35 (d, 1H), 7.22 (dd, 2H). MS 399.6, 401.6 (M+1)$^+$.

Intermediate IV

6-Bromo-N-(4-(trifluoromethyl)benzyl)imidazo[1,2-a]pyridine-2-carboxamide

The title compound was prepared by essentially following the same procedures described for Intermediate I, using (4-(trifluoromethyl)phenyl)methanamine and ethyl 6-bromoimidazo[1,2-a]pyridine-2-carboxylate as starting materials.

$^1$H NMR (400 MHz, CDCl$_3$) δ 8.31 (q, 1H), 8.13 (s, 1H), 7.78 (t, 1H), 7.57 (d, 2H), 7.47 (d, 2H), 7.42 (d, 1H), 7.29 (dd, 1H), 4.71 (d, 2H). MS 398.0, 400.0 (M+1)$^+$.

Intermediate V

6-Bromo-N-(3-(trifluoromethoxy)phenyl)imidazo[1,2-a]pyridine-2-carboxamide

The title compound was prepared by essentially following the same procedures described for Intermediate I, using 3-(trifluoromethoxy)aniline and ethyl 6-bromoimidazo[1,2-a]pyridine-2-carboxylate as starting materials.

$^1$H NMR (400 MHz, CDCl$_3$) δ 9.57 (br s, 1H), 8.38 (s, 1H), 8.21 (s, 1H), 7.83 (s, 1H), 7.61 (d, 1H), 7.57 (d, 1H), 7.43 (d, 1H), 7.36 (d, 1H), 6.98 (d, 1H). MS 399.6, 401.6 (M+1)$^+$.

Intermediate VI

6-Bromo-N-(3-(trifluoromethyl)phenyl)imidazo[1,2-a]pyridine-2-carboxamide

The title compound was prepared by essentially following the same procedures described for Intermediate I, using 3-(trifluoromethyl)aniline and ethyl 6-bromoimidazo[1,2-a]pyridine-2-carboxylate as starting materials.

$^1$H NMR (400 MHz, CDCl$_3$) δ 9.30 (br s, 1H), 8.33-8.32 (m, 1H), 8.17 (s, 1H), 8.05 (s, 1H), 7.92 (d, 1H), 7.49 (d, 1H), 7.46 (d, 1H), 7.37 (d, 1H), 7.34 (dd, 1H). MS 383.6, 385.6 (M+1)$^+$.

Intermediate VII

6-Bromo-N-(3-(trifluoromethoxy)benzyl)imidazo[1,2-a]pyridine-2-carboxamide

The title compound was prepared by essentially following the same procedures described for Intermediate I, using (3-(trifluoromethoxy)phenyl)methanamine and ethyl 6-bromoimidazo[1,2-a]pyridine-2-carboxylate as starting materials.

$^1$H NMR (400 MHz, CDCl$_3$) δ 10.23 (s, 1H), 8.80 (s, 1H), 8.76 (s, 1H), 7.99 (d, 1H), 7.85 (d, 1H), 7.33 (d, 1H), 7.29 (d, 1H), 7.20 (s, 1H), 7.05 (d, 1H), 4.61 (d, 2H). MS 413.8, 415.7 (M+1)$^+$.

Intermediate VIII

6-Bromo-N-(4-(tert-butyl)benzyl)imidazo[1,2-a]pyridine-2-carboxamide

The title compound was prepared by essentially following the same procedures described for Intermediate I, using (4-(tert-butyl)phenyl)methanamine and ethyl 6-bromoimidazo[1,2-a]pyridine-2-carboxylate as starting materials. $^1$H NMR (400 MHz, CDCl$_3$) δ 9.53 (s, 1H), 8.60 (s, 1H), 8.41 (s, 1H), 7.88 (d, 1H), 7.79 (d, 1H), 7.36 (d, 2H), 7.32 (d, 2H), 4.60 (d, 2H), 1.38 (s, 9H). MS 385.9, 387.9 (M+1)$^+$.

Intermediate IX

6-Bromo-N-(2-fluoro-5-(trifluoromethoxy)benzyl)imidazo[1,2-a]pyridine-2-carboxamide The title compound was prepared by essentially following the same procedures described for Intermediate I, using (2-fluoro-5-(trifluoromethoxy)phenyl)methanamine and ethyl 6-bromoimidazo[1,2-a]pyridine-2-carboxylate as starting materials.

$^1$H NMR (400 MHz, CDCl$_3$) δ 8.32 (s, 1H), 8.13 (s, 1H), 7.72 (s, 1H), 7.46 (d, 1H), 7.32 (dd, 2H), 7.28 (t, 1H), 7.12 (d, 1H), 7.08 (d, 1H), 4.70 (d, 2H). MS 431.7, 433.7 (M+1)$^+$.

Intermediate X

6-Bromo-N-(4-fluoro-3-(trifluoromethoxy)benzyl)imidazo[1,2-a]pyridine-2-carboxamide The title compound was prepared by essentially following the same procedures described for Intermediate I, using (4-fluoro-3-(trifluoromethoxy)phenyl)methanamine and ethyl 6-bromoimidazo[1,2-a]pyridine-2-carboxylate as starting materials.

$^1$H NMR (400 MHz, CDCl$_3$) δ 9.64 (s, 1H), 8.82 (d, 2H), 7.93 (d, 1H), 7.72 (d, 1H), 7.32 (d, 2H), 7.10 (t, 1H), 4.57 (d, 2H). MS 431.7, 433.7 (M+1)$^+$.

Intermediate XI

6-Bromo-N-(3-fluoro-4-(trifluoromethyl)benzyl)imidazo[1,2-a]pyridine-2-carboxamide The title compound was prepared by essentially following the same procedures described for Intermediate I, using (3-fluoro-4-(trifluoromethyl)phenyl)methanamine and ethyl 6-bromoimidazo[1,2-a]pyridine-2-carboxylate as starting materials.

$^1$H NMR (400 MHz, CDCl$_3$) δ 8.37 (s, 1H), 8.19 (s, 1H), 8.12 (s, 1H), 7.52 (t, 1H), 7.44 (d, 1H), 7.34 (dd, 1H), 7.20 (t, 2H), 4.66 (d, 2H). MS 415.8, 417.8 (M+1)$^+$.

Intermediate XII

6-Bromo-N-(4-methoxybenzyl)imidazo[1,2-a]pyridine-2-carboxamide

The title compound was prepared by essentially following the same procedures described for Intermediate I, using (4-methoxyphenyl)methanamine and ethyl 6-bromoimidazo[1,2-a]pyridine-2-carboxylate as starting materials.

$^1$H NMR (400 MHz, CDCl$_3$) δ 8.32 (s, 1H), 8.15 (s, 1H), 7.74 (s, 1H), 7.44 (d, 1H), 7.32 (d, 1H), 7.28 (d, 2H), 6.85 (d, 2H), 4.58 (d, 2H), 3.78 (s, 3H). MS 359.8, 361.9 (M+1)$^+$.

Intermediate XIII

6-Bromo-N-(3-chloro-4-fluorophenyl)imidazo[1,2-a]pyridine-2-carboxamide

The title compound was prepared by essentially following the same procedures described for Intermediate I, using 3-chloro-4-fluoroaniline and ethyl 6-bromoimidazo[1,2-a]pyridine-2-carboxylate as starting materials.

¹H NMR (400 MHz, CDCl₃) δ 9.31 (s, 1H), 8.36 (s, 1H), 8.19 (s, 1H), 7.97 (d, 1H), 7.80 (m, 1H), 7.54 (d, 2H), 7.40 (dd, 1H), 7.14 (t, 1H). MS 367.8, 369.7 (M+1)⁺.

Intermediate XIV

N-(Benzo[d][1,3]dioxol-5-ylmethyl)-6-bromoimidazo[1,2-a]pyridine-2-carboxamide

The title compound was prepared by essentially following the same procedures described for Intermediate I, using benzo[d][1,3]dioxol-5-ylmethanamine and ethyl 6-bromoimidazo[1,2-a]pyridine-2-carboxylate as starting materials.
¹H NMR (400 MHz, CDCl₃) δ 8.31 (s, 1H), 8.14 (s, 1H), 7.70 (s, 1H), 7.33 (d, 1H), 7.30 (dd, 1H), 6.85 (s, 1H), 6.81 (dd, 1H), 6.74 (d, 1H), 5.92 (s, 2H), 4.47 (d, 2H). MS 373.8, 375.8 (M+1)⁺.

Intermediate XV

6-Bromo-N-(3,4-dichlorophenyl)imidazo[1,2-a]pyridine-2-carboxamide

The title compound was prepared by essentially following the same procedures described for Intermediate I, using 3,4-dichloroaniline and ethyl 6-bromoimidazo[1,2-a]pyridine-2-carboxylate as starting materials.
¹H NMR (400 MHz, CDCl₃) δ 9.21 (s, 1H), 8.34 (t, 1H), 8.18 (s, 1H), 8.01 (d, 1H), 7.56 (dd, 1H), 7.51 (d, 1H), 7.42 (d, 1H), 7.36 (dd, 1H). MS 383.8, 385.7 (M+1)⁺.

Intermediate XVI

6-Bromo-N-(3-chlorophenyl)imidazo[1,2-a]pyridine-2-carboxamide

The title compound was prepared by essentially following the same procedures described for Intermediate I, using 3-chloroaniline and ethyl 6-bromoimidazo[1,2-a]pyridine-2-carboxylate as starting materials.
¹H NMR (400 MHz, CDCl₃) δ 9.23 (s, 1H), 8.34 (t, 1H), 8.18 (s, 1H), 7.88 (t, 1H), 7.58 (dq, 1H), 7.52 (d, 1H), 7.36 (dd, 1H), 7.28 (t, 1H), 7.11 (dq, 1H). MS 349.9, 351.8 (M+1)⁺.

Intermediate XVII

6-Bromo-N-(3-chloro-4-fluorobenzyl)imidazo[1,2-a]pyridine-2-carboxamide

The title compound was prepared by essentially following the same procedures described for Intermediate I, using (3-chloro-4-fluorophenyl)methanamine and ethyl 6-bromoimidazo[1,2-a]pyridine-2-carboxylate as starting materials.
¹H NMR (400 MHz, CDCl₃) δ 8.31 (s, 1H), 8.14 (s, 1H), 7.77 (s, 1H), 7.43 (d, 1H), 7.39 (dd, 1H), 7.29 (dd, 1H), 7.23-7.20 (m, 1H), 7.07 (t, 1H), 4.59 (d, 2H). MS 381.6, 383. (M+1)⁺.

Intermediate XVIII

6-Bromo-N-(2-methoxy-5-(trifluoromethoxy)benzyl)imidazo[1,2-a]pyridine-2-carboxamide The title compound was prepared by essentially following the same procedures described for Intermediate I, using (2-methoxy-5-(trifluoromethoxy)phenyl)methanamine and ethyl 6-bromoimidazo[1,2-a]pyridine-2-carboxylate as starting materials.
¹H NMR (400 MHz, CDCl₃) δ 8.36 (s, 1H), 8.15 (s, 1H), 7.58 (s, 1H), 7.46 (s, 1H), 7.21 (s, 1H), 7.09 (d, 1H), 6.82 (d, 1H), 4.62 (d, 2H), 3.88 (s, 3H). MS 443.6, 445.6 (M+1)⁺.

Intermediate XIX

6-Bromo-N-(4-isopropylbenzyl)imidazo[1,2-a]pyridine-2-carboxamide

The title compound was prepared by essentially following the same procedures described for Intermediate I, using (4-isopropylphenyl)methanamine and ethyl 6-bromoimidazo[1,2-a]pyridine-2-carboxylate as starting materials.
¹H NMR (400 MHz, CDCl₃) δ 8.40 (s, 1H), 8.24 (s, 1H), 7.57 (s, 1H), 7.47 (s, 1H), 7.35 (s, 1H), 7.30 (d, 2H), 7.17 (d, 2H), 4.59 (d, 2H), 2.85 (m, 1H), 1.20 (d, 6H). MS 371.8, 373.7 (M+1)⁺.

Intermediate XX

6-Bromo-N-(2-(4-fluorophenyl)propan-2-yl)imidazo[1,2-a]pyridine-2-carboxamide

The title compound was prepared by essentially following the same procedures described for Intermediate I, using 2-(4-fluorophenyl)propan-2-amine and ethyl 6-bromoimidazo[1,2-a]pyridine-2-carboxylate as starting materials.
¹H NMR (400 MHz, CDCl₃) δ 9.46 (s, 1H), 8.53 (s, 1H), 8.19 (s, 1H), 7.95 (d, 1H), 7.86 (d, 1H), 7.47-7.44 (m, 2H), 7.17-7.15 (m, 1H), 6.98 (t, 2H), 1.86 (s, 6H). MS 376.1, 378.1 (M+1)⁺.

Intermediate XXI

6-Bromo-N-(1-(2,5-difluorophenyl)cyclopropyl)imidazo[1,2-a]pyridine-2-carboxamide The title compound was prepared by essentially following the same procedures described for Intermediate I, using 1-(2,5-difluorophenyl)cyclopropanamine and ethyl 6-bromoimidazo[1,2-a]pyridine-2-carboxylate as starting materials.
¹H NMR (400 MHz, CDCl₃) δ 8.25 (t, 1H), 8.01 (s, 1H), 7.42 (dd, 1H), 7.36 (m, 1H), 7.26 (dd, 1H), 6.94-6.82 (m, 2H), 1.32 (d, 2H), 1.28 (d, 2H). MS 391.7, 393.6 (M+1)⁺.

Intermediate XXII

6-Bromo-N-(2-chloro-6-methylbenzyl)imidazo[1,2-a]pyridine-2-carboxamide

The title compound was prepared by essentially following the same procedures described for Intermediate I, using (2-chloro-6-methylphenyl)methanamine and ethyl 6-bromoimidazo[1,2-a]pyridine-2-carboxylate as starting materials.
¹H NMR (400 MHz, CDCl₃) δ 8.30 (s, 1H), 8.11 (s, 1H), 7.57 (s, 1H), 7.44 (d, 1H), 7.30 (d, 1H), 7.25 (d, 1H), 7.13 (t, 1H), 7.10 (d, 1H), 4.82 (d, 2H), 2.5 (s, 3H). MS 378.0, 380.0 (M+1)⁺.

Intermediate XXIII

6-Bromo-N-(3,4-dimethoxybenzyl)imidazo[1,2-a]pyridine-2-carboxamide

The title compound was prepared by essentially following the same procedures described for Intermediate I, using (3,4- dimethoxyphenyl)methanamine and ethyl 6-bromoimidazo[1,2-a]pyridine-2-carboxylate as starting materials.

$^1$H NMR (400 MHz, CDCl$_3$) δ 8.32 (s, 1H), 8.14 (s, 1H), 7.70 (s, 1H), 7.45 (d, 1H), 7.31 (d, 1H), 6.91 (d, 1H), 6.90 (s, 1H), 6.82 (d, 1H), 4.59 (d, 2H), 3.86 (s, 6H). MS 390.0, 392.0 (M+1)$^+$.

Intermediate XXIV (R,S)-6-Bromo-N-(1-phenylethyl)imidazo[1,2-a]pyridine-2-carboxamide The title compound was prepared by essentially following the same procedures described for Intermediate I, using racemic 1-phenylethanamine and ethyl 6-bromoimidazo[1,2-a]pyridine-2-carboxylate as starting materials.

$^1$H NMR (400 MHz, CDCl$_3$) δ 8.30 (s, 1H), 8.09 (s, 1H), 7.60-7.58 (m, 1H), 7.46 (d, 1H), 7.41 (d, 1H), 7.34 (t, 2H), 7.30 (d, 1H), 5.34 (m, 1H), 1.63 (d, 3H). MS 344.0, 346.0 (M+1)$^+$.

Intermediate XXV

6-Bromo-N-(4-(4-fluorophenoxy)benzyl)imidazo[1,2-a]pyridine-2-carboxamide

The title compound was prepared by essentially following the same procedures described for Intermediate I, using (4-(4-fluorophenoxy)phenyl)methanamine and ethyl 6-bromoimidazo[1,2-a]pyridine-2-carboxylate as starting materials.

$^1$H NMR (400 MHz, CDCl$_3$) δ 8.35 (s, 1H), 8.15 (s, 1H), 7.87 (s, 1H), 7.49 (d, 1H), 7.37 (d, 1H), 7.33 (d, 2H), 7.03-6.92 (m, 6H), 4.46 (d, 2H). MS 440.1, 442.1 (M+1)$^+$.

Intermediate XXVI

6-Bromo-N-((3,4-dihydro-2H-benzo[b][1,4]dioxepin-7-yl)methyl)imidazo[1,2-a]pyridine-2-carboxamide The title compound was prepared by essentially following the same procedures described for Intermediate I, using (3,4-dihydro-2H-benzo[b][1,4]dioxepin-7-yl)methanamine and ethyl 6-bromoimidazo[1,2-a]pyridine-2-carboxylate as starting materials.

$^1$H NMR (400 MHz, CDCl$_3$) δ 8.31 (s, 1H), 8.13 (s, 1H), 7.80 (s, 1H), 7.46 (d, 1H), 7.30 (dd, 1H), 7.03 (dd, 1H), 6.91 (dd, 1H), 6.87 (d, 1H), 4.64 (d, 2H), 4.26 (t, 2H), 4.19 (t, 2H), 2.22-2.17 (m, 2H). MS 402.1, 404.1 (M+1)$^+$.

Intermediate XXVII

6-Bromo-N-(2-chloro-6-fluorobenzyl)imidazo[1,2-a]pyridine-2-carboxamide

The title compound was prepared by essentially following the same procedures described for Intermediate I, using (2-chloro-6-fluorophenyl)methanamine and ethyl 6-bromoimidazo[1,2-a]pyridine-2-carboxylate as starting materials.

$^1$H NMR (400 MHz, CDCl$_3$) δ 8.33 (s, 1H), 8.11 (s, 1H), 7.55 (d, 1H), 7.42 (d, 1H), 7.20-7.16 (m, 1H), 7.01-6.97 (m, 1H), 4.81 (d, 2H). MS 381.7, 383.8 (M+1)$^+$.

Intermediate XXVIII

6-Bromo-N-(2,6-dichlorobenzyl)imidazo[1,2-a]pyridine-2-carboxamide

The title compound was prepared by essentially following the same procedures described for Intermediate I, using (2,6-dichlorophenyl)methanamine and ethyl 6-bromoimidazo[1,2-a]pyridine-2-carboxylate as starting materials.

$^1$H NMR (400 MHz, CDCl$_3$) δ 8.26 (s, 1H), 8.07 (s, 1H), 7.50-7.48 (m, 1H), 7.40 (d, 1H), 7.29 (d, 2H), 7.25 (dd, 1H), 7.16 (d, 1H), 4.94 (d, 2H). MS 397.7, 399.7 (M+1)$^+$.

Intermediate XXIX

6-Bromo-N-(2,6-difluorobenzyl)imidazo[1,2-a]pyridine-2-carboxamide

The title compound was prepared by essentially following the same procedures described for Intermediate I, using (2,6-difluorophenyl)methanamine and ethyl 6-bromoimidazo[1,2-a]pyridine-2-carboxylate as starting materials.

$^1$H NMR (400 MHz, CDCl$_3$) δ 8.27-8.26 (m, 1H), 8.08 (s, 1H), 7.56 (br s, 1H), 7.40 (d, 1H), 7.26-7.17 (m, 2H), 6.86 (d, 2H), 4.72 (d, 2H). MS 366.0, 368.0 (M+1)$^+$.

Intermediate XXX

6-Bromo-N-(2-chloro-6-(trifluoromethyl)benzyl)imidazo[1,2-a]pyridine-2-carboxamide The title compound was prepared by essentially following the same procedures described for Intermediate I, using (2-chloro-6-(trifluoromethyl)phenyl)methanamine and ethyl 6-bromoimidazo[1,2-a]pyridine-2-carboxylate as starting materials.

$^1$H NMR (400 MHz, CDCl$_3$) δ 8.26 (s, 1H), 8.10 (s, 1H), 7.59 (d, 2H), 7.37 (d, 2H), 7.30 (s, 1H), 7.23 (d, 1H), 4.92 (d, 2H). MS 431.7, 433.7 (M+1)$^+$.

Intermediate XXXI

N-Benzyl-6-bromoimidazo[1,2-a]pyridine-2-carboxamide

The title compound was prepared by essentially following the same procedures described for Intermediate I, using benzylamine and ethyl 6-bromoimidazo[1,2-a]pyridine-2-carboxylate as starting materials.

$^1$H NMR (400 MHz CDCl$_3$) δ 8.32 (s, 1H), 8.14 (s, 1H), 7.65 (br, 1H), 7.43 (d, 1H), 7.39-7.28 (m, 6H), 4.67 (d, 2H). MS 330.1, 332.1 (M+1)$^+$.

Intermediate XXXII

6-Bromo-N-(o-tolyl)imidazo[1,2-a]pyridine-2-carboxamide

The title compound was prepared by using procedures analogous to those described for the synthesis of Intermediate I, using o-toluidine and ethyl 6-bromoimidazo[1,2-a]pyridine-2-carboxylate as starting materials.

¹H NMR (400 MHz CDCl₃) δ 9.24 (s, 1H), 8.35 (s, 1H), 8.20-8.18 (m, 2H), 7.54 (d, 1H), 7.36 (d, 1H), 7.29-7.23 (m, 2H), 7.10 (t, 1H), 2.44 (s, 3H). MS 330.1, 332.1 (M+1)⁺.

Intermediate XXXIII

6-Bromo-N-(4-fluoro-2-(trifluoromethyl)phenyl)imidazo[1,2-a]pyridine-2-carboxamide The title compound was prepared by using procedures analogous to those described for the synthesis of Intermediate I, using 4-fluoro-2-(trifluoromethyl)aniline and ethyl 6-bromoimidazo[1,2-a]pyridine-2-carboxylate as starting materials.
¹H NMR (400 MHz CDCl₃) δ 9.66 (s, 1H), 8.47-8.43 (m, 1H), 8.34 (s, 1H), 8.19 (s, 1H), 7.56 (d, 1H), 7.39-7.29 (m, 3H). MS 402.0, 404.0 (M+1)⁺.

Intermediate XXXIV

6-Bromo-N-(2-(trifluoromethyl)phenyl)imidazo[1,2-a]pyridine-2-carboxamide

The title compound was prepared by using procedures analogous to those described for the synthesis of Intermediate I, using 2-(trifluoromethyl)aniline and ethyl 6-bromoimidazo[1,2-a]pyridine-2-carboxylate as starting materials.
¹H NMR (400 MHz CDCl₃) δ 9.77 (s, 1H), 8.52 (d, 1H), 8.34 (s, 1H), 8.19 (s, 1H), 7.66 (d, 1H), 7.63-7.56 (m, 2H), 7.35 (dd, 1H), 7.24 (d, 1H). MS 384.0, 386.0 (M+1)⁺.

Intermediate XXXV

6-Bromo-N-(2-fluorophenyl)imidazo[1,2-a]pyridine-2-carboxamide

The title compound was prepared by using procedures analogous to those described for the synthesis of Intermediate I, using 2-fluoroaniline and ethyl 6-bromoimidazo[1,2-a]pyridine-2-carboxylate as starting materials.
¹H NMR (400 MHz CDCl₃) δ 9.48 (s, 1H), 8.54 (t, 1H), 8.34 (s, 1H), 8.19 (s, 1H), 7.55 (d, 1H), 7.35 (dd, 1H), 7.21-7.08 (m, 3H). MS 334.0, 336.0 (M+1)⁺.

Intermediate XXXVI

6-Bromo-N-(2-methoxyphenyl)imidazo[1,2-a]pyridine-2-carboxamide

The title compound was prepared by using procedures analogous to those described for the synthesis of Intermediate I, using 2-methoxyaniline and ethyl 6-bromoimidazo[1,2-a]pyridine-2-carboxylate as starting materials.
¹H NMR (400 MHz CDCl₃) δ 9.80 (s, 1H), 8.57 (dd, 1H), 8.33 (s, 1H), 8.18 (s, 1H), 7.55 (d, 1H), 7.33 (dd, 1H), 7.09 (dt, 1H), 7.02 (dt, 1H), 6.93 (dd, 1H), 3.98 (s, 3H). MS 346.0, 348.0 (M+1)⁺.

Intermediate XXXVII

6-Bromo-N-(2-methylbenzyl)imidazo[1,2-a]pyridine-2-carboxamide

The title compound was prepared by using procedures analogous to those described for the synthesis of Intermediate I, using o-tolylmethanamine and ethyl 6-bromoimidazo[1,2-a]pyridine-2-carboxylate as starting materials.
¹H NMR (400 MHz CDCl₃) δ 8.32-8.31 (m, 1H), 8.13 (s, 1H), 7.50-7.45 (m, 1H), 4.43 (d, 1H), 7.34-7.26 (m, 2H), 7.21-7.17 (m, 3H), 4.66 (d, 2H), 2.38 (s, 3H). MS 344.1, 346.1 (M+1)⁺.

Intermediate XXXVIII

6-Bromo-N-(2,6-dimethylphenyl)imidazo[1,2-a]pyridine-2-carboxamide

The title compound was prepared by using procedures analogous to those described for the synthesis of Intermediate I, using 2,6-dimethylaniline and ethyl 6-bromoimidazo[1,2-a]pyridine-2-carboxylate as starting materials.
¹H NMR (400 MHz CDCl₃) δ 8.69 (s, 1H), 8.35 (s, 1H), 8.20 (s, 1H), 7.53 (d, 1H), 7.35 (d, 1H), 7.15-7.14 (m, 3H), 2.32 (s, 6H). MS 344.1, 346.1 (M+1)⁺.

Intermediate XXXIX

6-Bromo-N-(2,5-difluorophenyl)imidazo[1,2-a]pyridine-2-carboxamide

The title compound was prepared by using procedures analogous to those described for the synthesis of Intermediate I, using 2,5-difluoroaniline and ethyl 6-bromoimidazo[1,2-a]pyridine-2-carboxylate as starting materials.
¹H NMR (400 MHz CDCl₃+CD₃OD) δ 8.45 (s, 1H), 8.33-8.31 (m, 1H), 8.27 (s, 1H), 7.55 (d, 1H), 7.39 (d, 1H), 7.15-7.11 (m, 1H), 6.81-6.77 (m, 1H). MS 352.0, 3534.0 (M+1)⁺.

Intermediate XL

6-Bromo-N-(3,4,5-trifluorophenyl)imidazo[1,2-a]pyridine-2-carboxamide

The title compound was prepared by using procedures analogous to those described for the synthesis of Intermediate I, using 3,4,5-trifluoroaniline and ethyl 6-bromoimidazo[1,2-a]pyridine-2-carboxylate as starting materials.
¹H NMR (400 MHz CDCl₃+CD₃OD) δ 8.48 (s, 1H), 8.27 (s, 1H), 7.55-7.51 (m, 3H), 7.42 (d, 1H). MS 370.0, 372.0 (M+1)⁺.

Intermediate XLI

6-Bromo-N-(2-methoxybenzyl)imidazo[1,2-a]pyridine-2-carboxamide

The title compound was prepared by using procedures analogous to those described for the synthesis of Intermediate I, using (2-methoxyphenyl)methanamine and ethyl 6-bromoimidazo[1,2-a]pyridine-2-carboxylate as starting materials.
¹H NMR (400 MHz CDCl₃) δ 8.30 (s, 1H), 8.12 (s, 1H), 7.78 (br s, 1H), 7.46 (d, 1H), 7.35 (d, 1H), 7.29 (dd, 1H), 7.25 (d, 1H), 6.94-6.87 (m, 2H), 4.66 (d, 2H), 3.89 (s, 3H). MS 360.1, 362.1 (M+1)⁺.

Intermediate XLII

6-Bromo-N-(4-chloro-2,6-difluorobenzyl)imidazo[1,2-a]pyridine-2-carboxamide

The title compound was prepared by using procedures analogous to those described for the synthesis of Intermediate I, using (4-chloro-2,6-difluorophenyl)methanamine and ethyl 6-bromoimidazo[1,2-a]pyridine-2-carboxylate as starting materials.

$^{1}$H NMR (400 MHz CDCl$_{3}$) δ 8.33 (s, 1H), 8.12 (s, 1H), 7.84 (br s, 1H), 7.50 (d, 1H), 7.37 (d, 1H), 6.90-6.20 (m, 2H), 4.71 (d, 2H).

Intermediate XLIII

6-Bromo-N-(2,4-dichloro-6-methylbenzyl)imidazo[1,2-a]pyridine-2-carboxamide

The title compound was prepared by using procedures analogous to those described for the synthesis of Intermediate I, using (2,4-dichloro-6-methylphenyl)methanamine and ethyl 6-bromoimidazo[1,2-a]pyridine-2-carboxylate as starting materials.

$^{1}$H NMR (400 MHz CDCl$_{3}$) δ 8.34 (s, 1H), 8.12 (s, 1H), 7.80 (br s, 1H), 7.52 (d, 1H), 7.38 (d, 1H), 7.29-7.26 (m, 1H), 7.13-7.10 (m, 1H), 4.77 (d, 2H), 2.51 (s, 3H).

Intermediate XLIV

6-Bromo-N-(2,4,6-trimethylbenzyl)imidazo[1,2-a]pyridine-2-carboxamide

The title compound was prepared by using procedures analogous to those described for the synthesis of Intermediate I, using mesitylmethanamine and ethyl 6-bromoimidazo[1,2-a]pyridine-2-carboxylate as starting materials.

$^{1}$H NMR (400 MHz CDCl$_{3}$) δ 8.31 (s, 1H), 8.12 (s, 1H), 7.41 (d, 1H), 7.29 (dd, 1H), 7.20 (br s, 1H), 6.88 (s, 2H), 4.65 (d, 2H), 2.38 (s, 6H), 2.27 (s, 3H).

Intermediate XLV

6-Bromo-N-(4-methylbenzyl)-[1,2,4]triazolo[1,5-a]pyridine-2-carboxamide

The title compound was prepared by using procedures analogous to those described for the synthesis of Intermediate I, using p-tolylmethanamine and ethyl 6-bromo-[1,2,4]triazolo[1,5-a]pyridine-2-carboxylate as starting materials.

$^{1}$H NMR (400 MHz CDCl$_{3}$) δ 8.78 (s, 1H), 7.71-7.63 (m, 2H), 7.58 (br s, 1H), 7.27 (d, 2H), 7.16 (d, 2H), 4.68 (d, 2H), 2.35 (s, 3H).

Intermediate XLVI

2-Bromo-N-(4-(tert-butyl)benzyl)imidazo[2,1-b]thiazole-6-carboxamide

Hydroxybenzotriazole (109 mg, 0.81 mmol), N,N-diisopropylethylamine (0.23 ml, 1.34 mmol), and 1-ethyl-3-(3-dimethylaminopropyl)carbodiimide (155 mg, 0.81 mmol) were sequentially added to a the solution of 2-bromoimidazo[2,1-b]thiazole-6-carboxylic acid (supplied by Chemizon, 200 mg, 0.81 mmol) in a solvent mixture of methylene chloride (5 ml) and N,N-dimethyl formamide (2 ml) at room temperature. The reaction mixture was stirred at room temperature for 2 hours. After the addition of (4-(tert-butyl)phenyl)methanamine (0.42 ml, 2.78 mmol) at room temperature, the reaction mixture was stirred at room temperature for 24 hours, then diluted with methylene chloride. The reaction mixture was partitioned between methylene chloride and water. The aqueous layer was extracted with methylene chloride. The combined organic layer was washed with brine, then dried over anhydrous magnesium sulfate. After concentration, water was added to the residue. Filtration, followed by drying in vacuo, gave the title compound, 2-bromo-N-(4-(tert-butyl)benzyl)imidazo[2,1-b]thiazole-6-carboxamide, as a solid (148 mg, 87% yield).

$^{1}$H NMR (400 MHz, CDCl$_{3}$) δ 8.01 (s, 1H), 7.55 (s, 1H), 7.48 (m, 1H), 7.27 (d, 1H), 7.11 (d, 1H), 7.08 (d, 1H), 4.66 (d, 2H), 1.62 (s, 9H). MS 392.0, 394.0 (M+1)$^{+}$.

Intermediate XLVII

2-Bromo-N-(3-chlorophenyl)imidazo[2,1-b]thiazole-6-carboxamide

The title compound was prepared by essentially following the same procedures described for Intermediate XLVI, using 3-chloroaniline and 2-bromoimidazo[2,1-b]thiazole-6-carboxylic acid as starting materials.

$^{1}$H NMR (400 MHz, CDCl$_{3}$) δ 8.95 (s, 1H), 8.08 (s, 1H), 7.84 (t, 1H), 7.58 (s, 1H), 7.51 (dq, 1H), 7.27 (t, 2H), 7.09 (dq, 1H). MS 355.6, 357.6 (M+1)$^{+}$.

Intermediate XLVIII

2-Bromo-N-(3-chloro-4-(trifluoromethoxy)benzyl)imidazo[2,1-b]thiazole-6-carboxamide The title compound was prepared by essentially following the same procedures described for Intermediate XLVI, using (3-chloro-4-(trifluoromethoxy)phenyl)methanamine and 2-bromoimidazo[2,1-b]thiazole-6-carboxylic acid as starting materials.

$^{1}$H NMR (400 MHz, CDCl$_{3}$) δ 8.03 (s, 1H), 7.55 (s, 1H), 7.54-7.52 (m, 1H), 7.45 (s, 1H), 7.26 (d, 2H), 4.59 (d, 2H). MS 453.8, 455.8 (M+1)$^{+}$.

Intermediate XLIX

2-Bromo-N-(3-chloro-4-fluorobenzyl)imidazo[2,1-b]thiazole-6-carboxamide

The title compound was prepared by essentially following the same procedures described for Intermediate XLIV, using (3-chloro-4-fluorophenyl)methanamine and 2-bromoimidazo[2,1-b]thiazole-6-carboxylic acid as starting materials.

$^{1}$H NMR (400 MHz, CDCl$_{3}$) δ 8.02 (s, 1H), 7.55 (s, 1H), 7.48-7.46 (m, 1H), 7.38 (dd, 1H), 7.23-7.19 (m, 1H), 7.08 (t, 1H), 4.56 (d, 2H). MS 387.9, 389.8 (M+1)$^{+}$.

Intermediate L

2-Bromo-N-(3-(trifluoromethoxy)benzyl)imidazo[2,1-b]thiazole-6-carboxamide

The title compound was prepared by essentially following the same procedures described for Intermediate XLIV, using (3-(trifluoromethoxy)phenyl)methanamine and 2-bromoimidazo[2,1-b]thiazole-6-carboxylic acid as starting materials.

$^{1}$H NMR (400 MHz, CDCl$_{3}$) δ 8.03 (s, 1H), 7.52 (s, 1H), 7.56 (t, 2H), 7.26 (t, 2H), 4.67 (d, 2H). MS 419.9, 421.9 (M+1)$^{+}$.

Intermediate LI

2-Bromo-N-(2-fluoro-5-(trifluoromethoxy)benzyl)imidazo[2,1-b]thiazole-6-carboxamide The title compound was prepared by essentially following the same procedures described for Intermediate XLIV, using (2-fluoro-5-(trifluoromethoxy)phenyl)methanamine and 2-bromoimidazo[2,1-b]thiazole-6-carboxylic acid as starting materials.
$^1$H NMR (400 MHz, CDCl$_3$) δ 8.03 (s, 1H), 7.56 (s, 1H), 7.36 (t, 1H), 7.29 (d, 1H), 7.19 (s, 1H), 7.13 (d, 1H), 4.65 (d, 2H). MS 437.8, 439.9 (M+1)$^+$.

Intermediate LII

2-Bromo-N-(3-(trifluoromethoxy)phenyl)imidazo[2,1-b]thiazole-6-carboxamide

The title compound was prepared by essentially following the same procedures described for Intermediate XLIV, using 3-(trifluoromethoxy)aniline and 2-bromoimidazo[2,1-b]thiazole-6-carboxylic acid as starting materials.
$^1$H NMR (400 MHz, CDCl$_3$) δ 9.03 (s, 1H), 8.08 (s, 1H), 7.78 (s, 1H), 7.57 (s, 1H), 7.51 (d, 1H), 7.34 (t, 1H), 6.97 (d, 1H). MS 405.8, 407.8 (M+1)$^+$.

Intermediate LIII

2-Bromo-N-(4-isopropylbenzyl)imidazo[2,1-b]thiazole-6-carboxamide

The title compound was prepared by essentially following the same procedures described for Intermediate XLIV, using (4-isopropylphenyl)methanamine and 2-bromoimidazo[2,1-b]thiazole-6-carboxylic acid as starting materials.
$^1$H NMR (400 MHz, CDCl$_3$) δ 8.01 (s, 1H), 7.54 (s, 1H), 7.34 (s, 1H), 7.27 (d, 2H), 7.19 (d, 2H), 4.58 (d, 2H), 2.95-2.84 (m, 1H), 1.23 (d, 6H). MS 378.0, 380.0 (M+1)$^+$.

Intermediate LIV

2-Bromo-N-(1-(2,5-difluorophenyl)cyclopropyl)imidazo[2,1-b]thiazole-6-carboxamide The title compound was prepared by essentially following the same procedures described for Intermediate XLIV, using 1-(2,5-difluorophenyl)cyclopropanamine and 2-bromoimidazo[2,1-b]thiazole-6-carboxylic acid as starting materials.
$^1$H NMR (400 MHz, CDCl$_3$) δ 7.91 (s, 1H), 7.79 (s, 1H), 7.50 (s, 1H), 7.37-7.34 (m, 1H), 6.96-6.84 (m, 2H), 1.30 (t, 2H), 1.28 (t, 2H). MS 397.9, 399.9 (M+1)$^+$.

Intermediate LV

2-Bromo-N-(2-methoxy-5-(trifluoromethoxy)benzyl)imidazo[2,1-b]thiazole-6-carboxamide The title compound was prepared by essentially following the same procedures described for Intermediate XLIV, using (2-methoxy-5-(trifluoromethoxy)phenyl)-methanamine and 2-bromoimidazo[2,1-b]thiazole-6-carboxylic acid as starting materials.
$^1$H NMR (400 MHz, CDCl$_3$) δ 7.99 (s, 1H), 7.53 (s, 1H), 7.52 (s, 1H), 7.20 (d, 1H), 7.10 (dd, 1H), 6.84 (d, 1H), 4.68 (d, 2H), 3.88 (s, 3H). MS 449.9, 451.9 (M+1)$^+$.

Intermediate LVI

2-Bromo-N-(4-(trifluoromethoxy)benzyl)imidazo[2,1-b]thiazole-6-carboxamide

The title compound was prepared by essentially following the same procedures described for Intermediate XLIV, using (4-(trifluoromethoxy)phenyl)methanamine and 2-bromoimidazo[2,1-b]thiazole-6-carboxylic acid as starting materials.
$^1$H NMR (400 MHz, CDCl$_3$) δ 7.53 (s, 1H), 7.43 (td, 1H), 7.36 (d, 2H), 7.16 (dd, 2H), 4.60 (d, 2H). MS 419.9, 421.9 (M+1)$^+$.

Intermediate LVII

2-Bromo-N-(4-methoxybenzyl)imidazo[2,1-b]thiazole-6-carboxamide

The title compound was prepared by essentially following the same procedures described for Intermediate XLIV, using (4-methoxyphenyl)methanamine and 2-bromoimidazo[2,1-b]thiazole-6-carboxylic acid as starting materials.
$^1$H NMR (400 MHz, CDCl$_3$) δ 7.98 (s, 1H), 7.52 (s, 1H), 7.31 (s, 1H), 7.25 (dd, 2H), 6.84 (dd, 2H), 4.53 (d, 2H), 3.77 (s, 3H). MS 365.8, 367.9 (M+1)$^+$.

Intermediate LVIII

N-(Benzo[d][1,3]dioxol-5-ylmethyl)-2-bromoimidazo[2,1-b]thiazole-6-carboxamide

The title compound was prepared by essentially following the same procedures described for Intermediate XLIV, using benzo[d][1,3]dioxol-5-ylmethanamine and 2-bromoimidazo[2,1-b]thiazole-6-carboxylic acid as starting materials.
$^1$H NMR (400 MHz, CDCl$_3$) δ 8.01 (s, 1H), 7.54 (s, 1H), 7.35 (s, 1H), 6.84 (s, 1H), 6.81 (d, 1H), 6.75 (d, 1H), 5.93 (s, 2H), 4.51 (d, 2H). MS 379.9, 381.9 (M+1)$^+$.

Intermediate LIX

2-Bromo-N-(4-fluoro-3-(trifluoromethoxy)benzyl)imidazo[2,1-b]thiazole-6-carboxamide The title compound was prepared by essentially following the same procedures described for Intermediate XLIV, using (4-fluoro-3-(trifluoromethoxy)phenyl)methanamine and 2-bromoimidazo[2,1-b]thiazole-6-carboxylic acid as starting materials.
$^1$H NMR (400 MHz, CDCl$_3$) δ 8.00 (s, 1H), 7.54 (s, 1H), 7.46 (s, 1H), 7.27 (d, 1H), 7.25 (d, 1H), 7.13 (t, 1H), 4.57 (d, 2H). MS 437.9, 439.9 (M+1)$^+$.

Intermediate LX

2-Bromo-N-(3-chloro-4-fluorophenyl)imidazo[2,1-b]thiazole-6-carboxamide

The title compound was prepared by essentially following the same procedures described for Intermediate XLIV, using 3-chloro-4-fluoroaniline and 2-bromoimidazo[2,1-b]thiazole-6-carboxylic acid as starting materials.
$^1$H NMR (400 MHz, CDCl$_3$) δ 8.90 (s, 1H), 8.06 (s, 1H), 7.89 (dd, 1H), 7.56 (s, 1H), 7.49-7.45 (m, 1H), 7.10 (t, 1H). MS 373.8, 375.9 (M+1)$^+$.

Intermediate LXI 2-bromo-N-(2,6-dichlorobenzyl)imidazo[2,1-b]thiazole-6-carboxamide The title compound was prepared by essentially following the same procedures described for Intermediate XLIV, using (2,6-dichlorophenyl)methanamine and 2-bromoimidazo[2,1-b]thiazole-6-carboxylic acid as starting materials.

$^{1}$H NMR (400 MHz, CDCl$_{3}$) δ 7.98 (s, 1H), 7.51 (s, 1H), 7.30 (d, 2H), 7.17 (d, 1H), 4.91 (d, 2H). MS 405.5, 407.4 (M+1)$^{+}$.

Intermediate LXII 2-bromo-N-(2-chloro-6-fluorobenzyl)imidazo[2,1-b]thiazole-6-carboxamide The title compound was prepared by essentially following the same procedures described for Intermediate XLIV, using (2-chloro-6-fluorophenyl)methanamine and 2-bromoimidazo[2,1-b]thiazole-6-carboxylic acid as starting materials.

$^{1}$H NMR (400 MHz, CDCl$_{3}$) δ 7.98 (s, 1H), 7.51 (s, 1H), 7.18 (d, 2H), 7.01-7.96 (m, 1H), 4.78 (d, 2H). MS 388.6, 390.5 (M+1)$^{+}$.

Intermediate LXIII 2-bromo-N-(2,6-difluorobenzyl)imidazo[2,1-b]thiazole-6-carboxamide The title compound was prepared by essentially following the same procedures described for Intermediate XLIV, using (2,6-difluorophenyl)methanamine and 2-bromoimidazo[2,1-b]thiazole-6-carboxylic acid as starting materials.

$^{1}$H NMR (400 MHz, CDCl$_{3}$) δ 7.98 (s, 1H), 7.52 (s, 1H), 7.23 (s, 1H), 6.88 (d, 2H), 4.69 (d, 2H). MS 371.6, 373.7 (M+1)$^{+}$.

Intermediate LXIV 2-bromo-N-(4-chloro-2,6-difluorobenzyl)imidazo[2,1-]thiazole-6-carboxamide The title compound was prepared by essentially following the same procedures described for Intermediate XLIV, using (4-chloro-2,6-difluorophenyl)methanamine and 2-bromoimidazo[2,1-b]thiazole-6-carboxylic acid as starting materials.

$^{1}$H NMR (400 MHz, CDCl$_{3}$) δ 7.92 (s, 1H), 7.53 (m, 2H), 6.92 (d, 1H), 4.65 (d, 2H). MS 405.5, 407.5 (M+1)$^{+}$.

Intermediate LXV

Ethyl 2-((1s,4s)-4-(4-(4,4,5,5-tetramethyl-1,3,2-dioxaborolan-2-yl)phenyl)cyclohexyl)acetate Step A: Ethyl 2-(4-(4-hydroxyphenyl)cyclohexylidene)acetate Triethylphosphonoacetate (12.60 g, 63.08 mmol) was added to a solution of 4-(4-hydroxyphenyl)cyclohexanone (10.00 mg, 52.57 mmol) in tetrahydrofuran (THF, 400 mL) at 0° C. NaH (60% in mineral oil, 4.84 g, 121. mmol) was added portionwise to the above mixture so that the internal temperature was maintained below 10° C. The reaction mixture was stirred at 0° C. for 20 minutes and slowly warmed to room temperature and stirred for an additional 2.5 hours, the reaction mixture was quenched with water (30 mL), then concentrated under reduced pressure and diluted with water (150 mL). The aqueous layer was extracted with ethyl acetate (3×150 mL). The combined organic layer was dried over anhydrous sodium sulfate, filtered, and concentrated to dryness under reduced pressure to give ethyl 2-(4-(4-hydroxyphenyl)cyclohexylidene)acetate as a white solid (12.91 g, yield 94%).

$^{1}$H NMR (400 MHz CDCl$_{3}$) δ 7.01 (d, 2H), 6.77 (d, 2H), 5.68 (s, 1H), 4.67 (s, 1H), 4.16 (q, 2H), 3.97-2.76 (m, 1H), 2.76-2.69 (m, 1H), 2.41-2.30 (m, 2H), 2.05-1.98 (m, 3H), 1.64-1.54 (m, 2H), 1.29 (t, 3H).

Step B: Ethyl 2-((1s,4s)-4-(4-hydroxyphenyl)cyclohexyl)acetate

Ethyl 2-(4-(4-hydroxyphenyl)cyclohexylidene)acetate (12.91 g, 49.60 mmol) from Step A of intermediate LXV was hydrogenated under atmospheric hydrogen with 10% Pd/C (1.29 g) as a catalyst in ethanol (250 mL) at ambient temperature for 12 hours. Filtration through celite followed by concentration gave the cis, trans mixture as a white solid. The mixture compound was dissolved in hot ethyl acetate (12 mL). The solution was maintained at room temperature for 12 hours. A white precipitate was filtered and washed with 50 mL of ice-cold solvent (hexanes:ethyl acetate=85:15 (v/v)) to give the trans isomer (2.66 g). The filtrate was concentrated in vacuo and the residual solid was dissolved in a 15 mL of hot mixture solvent (hexane:ethyl acetate=1:1). The solution was allowed to cool slowly to room temperature for 12 hours. A white precipitate was filtered and washed with an ice-cold mixture solvent (hexanes: ethyl acetate=85:15 (v/v)) to give the trans isomer (2.12 g). The two solids were combined to give the title compound as a white solid (4.78 g, yield 37%).

$^{1}$H NMR (400 MHz CDCl$_{3}$) δ 7.06 (d, 2H), 6.75 (d, 2H), 4.80 (s, 1H), 4.14 (q, 2H), 2.43-2.36 (m, 1H), 2.23 (d, 2H), 1.88-1.79 (m, 5H), 1.45 (q, 2H), 1.27 (t, 3H), 1.14 (d, 2H).

Step C: Ethyl 2-((1s,4s)-4-(4-(((trifluoromethyl)sulfonyl)oxy)phenyl)cyclohexyl)acetate Triethylamine (3.21 mL, 23.0 mmol) and trifluoromethanesulfonic anhydride (6.06 g, 21.5 mmol) were added dropwise to a solution of ethyl 2-((1r,4r)-4-(4-hydroxyphenyl)cyclohexyl)acetate (4.03 g, 15.4 mmol) from Step B of intermediate LXV in 40 mL of methylene chloride at 0° C. The reaction mixture was stirred under N$_{2}$ atmosphere for 5 hours, then poured into a saturated aqueous solution of sodium bicarbonate (100 mL) and extracted with methylene chloride (100 mL). The combined extracts were washed with brine, dried over anhydrous magnesium sulfate and concentrated. The crude compound was filtered through a short path column (silica gel, hexanes: ethyl acetate=1:1 (v/v)) to give the title compound as a white solid (5.10 g, yield 84%).

$^{1}$H NMR (400 MHz CDCl$_{3}$) δ 7.27 (d, 2H), 7.18 (d, 2H), 4.13 (q, 2H), 2.51-2.47 (m, 1H), 2.23 (d, 2H), 1.91-1.83 (m, 3H), 1.47 (q, 2H), 1.27 (t, 5H), 1.16 (d, 2H).

Step D: Ethyl 2-((1s,4s)-4-(4-(4,4,5,5-tetramethyl-1,3,2-dioxaborolan-2-yl)phenyl)cyclohexyl)acetate Potassium acetate (5.19 g, 52.9 mmol) and Pd(dppf)Cl$_{2}$ (1.44 g, 1.76 mmol) were added to a solution of ethyl 2-((1s,4s)-4-(4-(((trifluoromethyl)sulfonyl)oxy)phenyl)cyclohexyl)acetate (6.95 g, 17.6 mmol) from Step C of intermediate LXV and bis(pinacolato)diboron (4.92 g, 19.4 mmol) in 1,4-dioxane (150 mL) at room temperature. The reaction mixture was degassed under reduced pressure three times, placed under N$_{2}$ atmosphere and stirred at 90° C. for 12 hours. The reaction mixture was cooled, filtered through a celite and eluted with ethyl acetate (150 mL). The solvent was removed under reduced pressure and the crude brown oil was purified by flash chromatography (silica gel, hexanes: ethyl acetate=3:1 (v/v)) to give the title compound as a white solid (5.9 g, yield 91%).

$^1$H NMR (400 MHz CDCl$_3$) δ 7.74 (d, 2H), 7.21 (d, 2H), 4.13 (q, 2H), 2.51-2.43 (m, 1H), 2.23 (d, 2H), 1.90-1.81 (m, 5H), 1.57-1.47 (m, 2H), 1.31-1.35 (m, 6H), 1.29-1.23 (m, 9H), 1.19-1.09 (m, 2H). MS 395.2 (M+Na)$^+$.

Intermediate LXVI

Ethyl 2-methyl-((1s,4s)-4-(4-(4,4,5,5-tetramethyl-1,3,2-dioxaborolan-2-yl)phenyl)-cyclohexyl)propanoate Step A: (R,S)-Ethyl 2-((1s,4s)-4-(4-(4,4,5,5-tetramethyl-1,3,2-dioxaborolan-2-yl)phenyl)cyclohexyl) propanoate Lithium bis(trimethylsilyl)amide (2.70 g, 16.1 mmol) was added to ethyl 2-((1r,4r)-4-(4-(4,4,5,5-tetramethyl-1,3,2-dioxaborolan-2-yl)phenyl)cyclohexyl)acetate (5.0 g, 13. mmol) (Intermediate LXV) in 60 mL of THF at 0° C. under N$_2$ atmosphere. The resulting mixture was stirred at 0° C. for 30 minutes and then methyl iodide (1.26 mL, 20.1 mmol) was added thereto. After being stirred for an additional 30 minutes, the reaction mixture was quenched with saturated ammonium chloride (50 mL). The aqueous layer was extracted with ethyl acetate (100 mL) and the combined organic layer was washed with water (50 mL), dried over anhydrous magnesium sulfate, filtered, and concentrated. The crude compound was purified by flash chromatography (silicagel, hexanes:ethyl acetate=9:1 (v/v)) to give the title compound as a white solid (3.7 g, yield 71%).

$^1$H NMR (400 MHz CDCl$_3$) δ 7.74 (d, 2H), 7.21 (d, 2H), 4.11 (q, 2H), 2.50-2.44 (m, 1H), 2.30-2.22 (m, 1H), 1.95-1.85 (m, 3H), 1.81-1.73 (m, 1H), 1.68-1.60 (m, 1H), 1.55-1.42 (m, 2H), 1.32 (s, 12H), 1.27 (m, 5H), 1.19-1.10 (m, 3H).

Step B: Ethyl 2-methyl-2-((1r,4r)-4-(4-(4,4,5,5-tetramethyl-1,3,2-dioxaborolan-2-yl)phenyl)cyclohexyl)propanoate Butyllithium (10.40 mL, 20.71 mmol) was added dropwise to a solution of diisopropylamine (2.92 mL, 20.7 mmol) in 30 mL of tetrahydrofuran under N$_2$ atmosphere, while maintaining the temperature between −70° C. and −60° C. After 30 minutes, (R,S)-ethyl 2-((1s,4s)-4-(4-(4,4,5,5-tetramethyl-1,3,2-dioxaborolan-2-yl)phenyl)cyclohexyl)propanoate (2.00 g, 5.18 mmol) from Step A of intermediate LXVI in 10 mL of tetrahydrofuran was added thereto and the reaction mixture was allowed to warm to 20° C. over 1.5 hours. After the solution was cooled to −65° C., methyl iodide (1.30 mL, 20.7 mmol) was added thereto and the reaction mixture was stirred for 1 hour and then allowed to warm to −30° C. The reaction was quenched with saturated ammonium chloride (100 mL) and extracted with ethyl acetate (200 mL). The organic phase was separated and washed with water (100 mL) and brine (100 mL). The organic phase was dried over anhydrous magnesium sulfate, filtered, and concentrated. The crude compound was purified by flash chromatography (silica gel, hexanes: ethyl acetate=9:1 (v/v)) to give the title compound as a white solid (1.40 g, yield 68%).

$^1$H NMR (400 MHz CDCl$_3$) δ 7.74 (2H, d, J=7.6 Hz), 7.21 (2H, d, J=7.6 Hz), 4.13 (2H, q, J=7.0 Hz), 2.51-2.42 (1H, m), 1.97-1.90 (2H, m), 1.76-1.65 (3H, m), 1.55-1.43 (2H, q, J=12.4 Hz), 1.33 (12H, s), 1.29-1.18 (5H, m), 1.14 (6H, s). MS 401.3 (M+1)$^+$.

Example 1

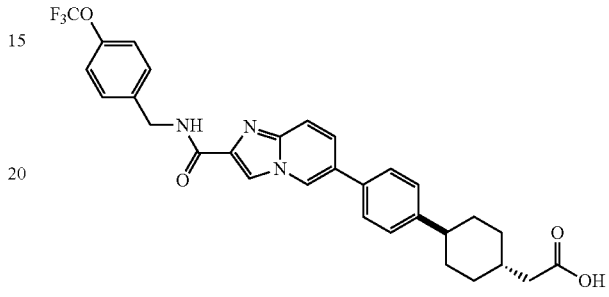

2-((1r,4r)-4-(4-(2-((4-(Trifluoromethoxy)benzyl) carbamoyl)imidazo[1,2-a]pyridin-6-1 acetic acid— Compound 1

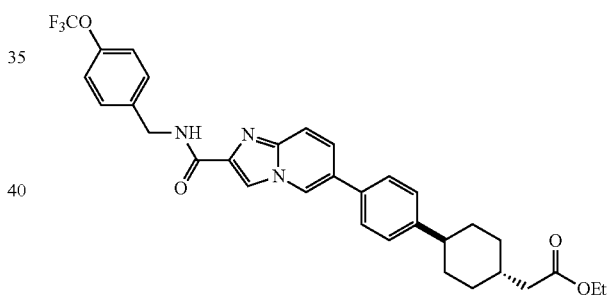

Step A: Ethyl 2-((1r,4r)-4-(4-(2-((4-trifluoromethoxybenzyl)carbamoyl)imidazo[1,2-a]pyridin-6-yl)phenyl)cyclohexyl)acetate Intermediate LXV, ethyl 2-((1 r,4r)-4-(4-(4,4,5,5-tetramethyl-1,3,2-dioxaborolan-2-yl)phenyl)cyclohexyl)acetate (452 mg, 1.21 mmol), [1,1'-Bis(diphenylphosphino)ferrocene]dichloro-palladium(II) complex with dichloromethane (82.7 mg, 0.10 mmol), and potassium phosphate tribasic (430 mg, 20.2 mmol) were sequentially added to a the solution of Intermediate I, 6-bromo-N-(4-(trifluoromethoxy) benzyl)imidazo[1,2-a]pyridine-2-carboxamide (420 mg, 1.01 mmol), in a solvent mixture (15 ml) of 1,4-dioxane and water (10:1 (v/v)) at room temperature. The reaction mixture was stirred at 90° C. for 20 hours. After cooling to room temperature, the reaction mixture was diluted with ethyl acetate (30 mL). The reaction mixture was partitioned between ethyl acetate and water, and the aqueous layer was extracted with ethyl acetate (30 mL×3). The combined organic layer was washed with brine and then dried over anhydrous magnesium sulfate. After concentration, the resulting residue was purified by flash chromatography (ethyl acetate: hexane=1:1 (v/v)) to give the title compound, ethyl 2-((1r,4r)-4-(4-(2-((4-(trifluoromethoxy)benzyl)carbamoyl) imidazo[1,2-a]pyridin-6-yl)phenyl)cyclo-hexyl)acetate as a solid (400 mg, 65% yield).

$^1$H NMR (400 MHz, CDCl$_3$) δ 8.27 (s, 1H), 8.18 (s, 1H), 7.71 (t, 1H), 7.57 (d, 1H), 7.47 (d, 2H), 7.39 (d, 2H), 7.31 (d, 2H), 7.17 (d, 2H), 4.66 (d, 2H), 4.13 (t, 2H), 2.52 (t, 1H), 2.24 (d, 2H), 2.24 (d, 2H), 1.91 (m, 6H), 1.53 (m, 2H), 1.26 (t, 3H), 1.17 (d, 1H). MS 580.1 (M+1)$^+$.

Step B: 2-((1r,4r)-4-(4-(2-((4-(Trifluoromethoxy) benzyl)carbamoyl)imidazo[1,2-a]pyridin-6-yl)phenyl)cyclohexyl)acetic acid Lithium hydroxide monohydrate (18 mg, 0.43 mmol) in water (2 ml) was added to a the solution of ethyl 2-((1r,4r)-4-(4-(2-((4-(trifluoromethoxy)benzyl)-carbamoyl)imidazo [1,2-a]pyridin-6-yl)phenyl)cyclohexyl)acetate (50 mg, 8.6× 10$^{-2}$ mmol) in tetrahydrofuran (4 ml) at room temperature. The reaction mixture was stirred at 50° C. for 20 hours. After cooling to room temperature, the reaction mixture was concentrated. To the above residue was added 1N HCl solution (2-3 ml). The resultant solid was filtered, washed with water, then dried to give Compound 1, 2-((1r,4r)-4-(4-(2-((4-(trifluoromethoxy)benzyl)-carbamoyl)imidazo[1,2-a]pyridin-6-yl)phenyl)cyclohexyl)acetic acid, as a solid (20 mg, 42% yield).

$^1$H NMR (400 MHz, DMSO-d$_6$) δ 9.26 (s, 1H), 9.01 (s, 1H), 7.45 (s, 1H), 7.38 (d, 1H), 7.70 (d, 1H), 7.63 (d, 2H), 7.44 (d, 2H), 7.37 (d, 2H), 7.31 (d, 2H), 4.49 (d, 2H), 2.13 (d, 2H), 1.81 (d, 4H), 1.73 (m, 1H), 1.49 (d, 2H), 1.11 (d, 2H). MS 552.3 (M+1)$^+$.

Example 2

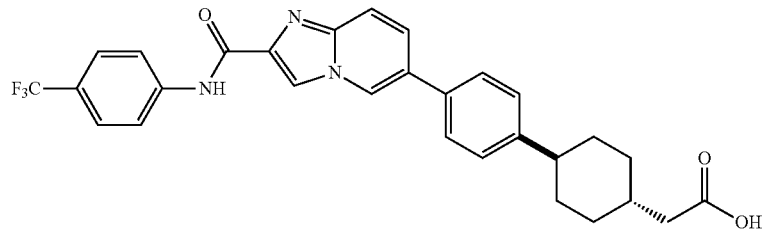

2-((1r,4r)-4-(4-(2-((4-(Trifluoromethyl)phenyl)carbamoyl)imidazo[1,2-a]pyridin-6-yl)phenyl)-cyclohexyl)acetic acid—Compound 2

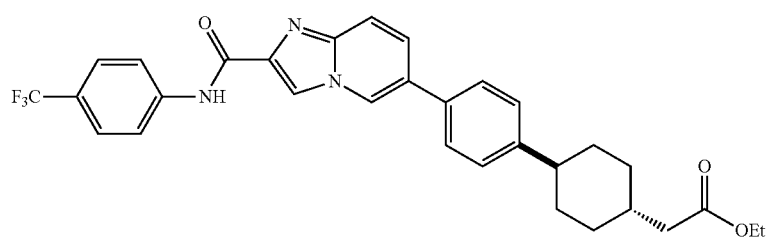

Step A: Ethyl 2-((1r,4r)-4-(4-(2-((4-(trifluoromethyl) phenyl)carbamoyl)imidazo[1,2-a]-pyridin-6-yl)phenyl)cyclohexyl)acetate The title compound was prepared from Intermediate II and Intermediate LXV by essentially following the same procedures described for step A of Example 1.

$^1$H NMR (400 MHz, CDCl$_3$) δ 9.41 (s, 1H), 8.32 (s, 1H), 8.27 (s, 1H), 7.90 (d, 2H), 7.64 (t, 3H), 7.50 (d, 2H), 7.33 (d, 2H), 4.11 (q, 2H), 2.54 (t, 2H), 2.22 (d, 2H), 1.94-1.82 (m, 6H), 1.73 (q, 2H), 1.21 (t, 3H), 1.12 (q, 2H). MS 550.1 (M+1)$^+$.

Step B: 2-((1r,4r)-4-(4-(2-((4-(Trifluoromethyl)phenyl)carbamoyl)imidazo[1,2-a]pyridin-6-yl)phenyl) cyclohexyl)acetic acid Compound 2 was prepared by essentially following the same procedures described for the step B of Example 1.

$^1$H NMR (400 MHz, DMSO-d$_6$) δ 10.76 (s, 1H), 8.96 (s, 1H), 8.56 (s, 1H), 8.14 (d, J=8.4 Hz, 2H), 7.74-7.69 (m, 3H), 7.64-7.61 (m, 2H), 7.37 (d, J=8.4 Hz, 2H), 2.48 (m, 1H, overlap with DMSO peak), 2.14 (d, J=7.2 Hz, 2H), 1.85-1.73 (m, 6H), 1.49 (q, J=12.0 Hz, 2H), 1.13 (q, J=10.8 Hz, 2H). MS 522.4 (M+1)$^+$.

Example 3

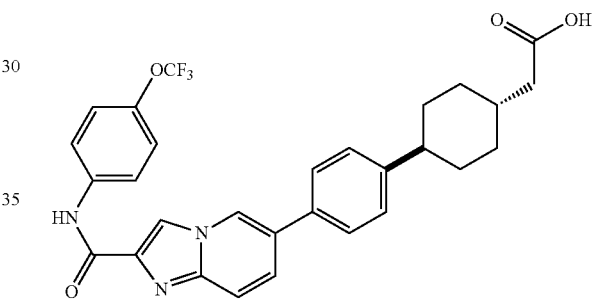

2-((1r,4r)-4-(4-(2-((4-(Trifluoromethoxy)phenyl)carbamoyl)imidazo[1,2-a]pyridin-6-yl)-phenyl)cyclohexyl)acetic acid—Compound 3

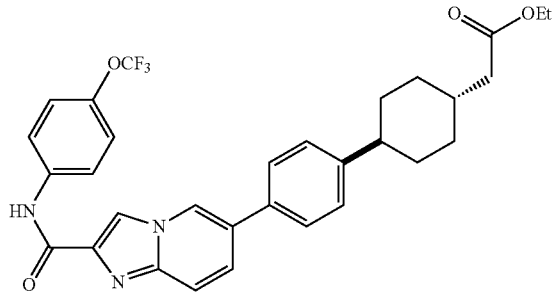

Step A: Ethyl 2-((1r,4r)-4-(4-(2-((4-(trifluoromethoxy)phenyl)carbamoyl)imidazo[1,2-a]pyridin-6-yl)phenyl)cyclohexyl)acetate The title compound was prepared from Intermediate III and Intermediate LXV by essentially following the same procedures described for step A of Example 1.

$^1$H NMR (400 MHz, CDCl$_3$) δ 9.29 (s, 1H), 8.28 (s, 1H), 7.82 (d, 1H), 7.76 (d, 2H), 7.49 (d, 2H), 7.35 (d, 2H), 7.22 (d, 2H), 4.14 (q, 2H), 2.58-2.45 (m, 1H), 2.23 (d, 2H), 1.96-1.87 (m, 6H), 1.52 (q, 2H), 1.27 (t, 3H), 1.15 (q, 2H). MS 565.9 (M+1)$^+$.

Step B: 2-((1r,4r)-4-(4-(2-((4-(Trifluoromethoxy)phenyl)carbamoyl)imidazo[1,2-a]pyridin-6-yl)phenyl)cyclohexyl)acetic acid Compound 3 was prepared by essentially following the same procedures described for the step B of Example 1.

$^1$H NMR (400 MHz, DMSO-d$_6$) δ 10.70 (s, 1H), 9.03 (s, 1H), 8.60 (s, 1H), 8.00 (d, 2H), 7.64 (d, 2H), 7.31 (t, 3H), 6.97 (d, 2H), 6.62 (d, 2H), 2.25 (m, 1H, overlap with DMSO peak), 2.13 (d, 2H), 1.83-1.77 (m, 6H), 1.49 (q, 2H), 1.12 (q, 2H). MS 538.4 (M+1)$^+$.

Example 4

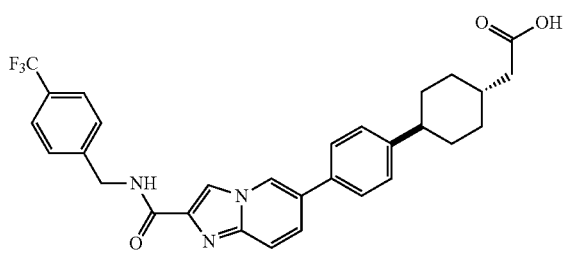

2-((1r,4r)-4-(4-(2-((4-(Trifluoromethyl)benzyl)carbamoyl)imidazo[1,2-a]pyridin-6-yl)-phenyl)cyclohexyl)acetic acid—Compound 4

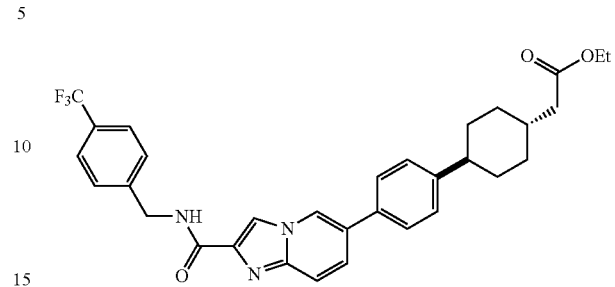

Step A: Ethyl 2-((1r,4r)-4-(4-(2-((4-(trifluoromethyl)benzyl)carbamoyl)imidazo[1,2-a]pyridin-6-yl)phenyl)cyclohexyl)acetate The title compound was prepared from Intermediate IV and Intermediate LXV by essentially following the same procedures described for step A of Example 1.

$^1$H NMR (400 MHz, CDCl$_3$) δ 8.18 (dd, 1H), 8.16 (d, 1H), 7.83 (t, 1H), 7.71 (s, 1H), 7.58 (t, 3H), 7.50 (d, 2H), 7.33 (d, 2H), 7.15 (dd, 1H), 4.73 (d, 2H), 4.13 (q, 2H), 2.53 (t, 1H), 2.25 (d, 2H), 1.91 (m, 5H), 1.56 (qd, 2H), 1.26 (t, 3H), 1.19 (m, 2H). MS 564.4 (M+1)$^+$.

Step B: 2-((1r,4r)-4-(4-(2-((4-(Trifluoromethyl)benzyl)carbamoyl)imidazo[1,2-a]pyridin-6-yl)phenyl)cyclohexyl)acetic acid Compound 4 was prepared by essentially following the same procedures described for the step B of Example 1.

$^1$H NMR (400 MHz, DMSO-d$_6$) δ 9.21 (s, 1H), 8.92 (s, 1H), 8.36 (s, 1H), 7.72-7.65 (m, 4H), 7.61 (d, 2H), 7.52 (d, 2H), 7.35 (d, 2H), 4.53 (d, 2H), 2.48 (m, 1H, overlap with DMSO peak), 2.13 (d, 2H), 1.82-1.74 (m, 6H), 1.49 (q, 2H), 1.12 (q, 2H). MS 536.0 (M+1)$^+$.

Example 5

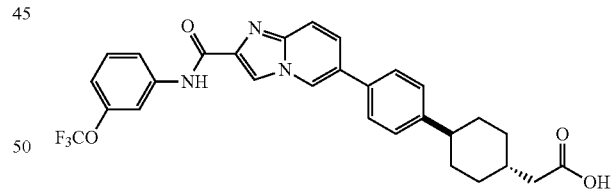

2-((1r,4r)-4-(4-(2-((3-(Trifluoromethoxy)phenyl)carbamoyl)imidazo[1,2-a]pyridin-6-yl)-phenyl)cyclohexyl)acetic acid—Compound 5

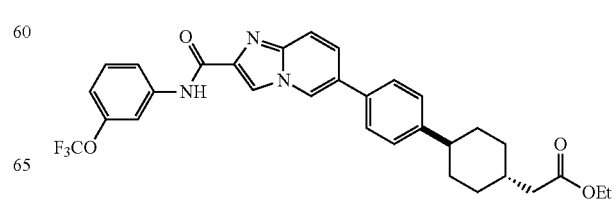

Step A: Ethyl 2-((1r,4r)-4-(4-(2-((3-(trifluoromethoxy)phenyl)carbamoyl)imidazo[1,2-a]pyridin-6-yl)phenyl)cyclohexyl)acetate The title compound was prepared from Intermediate V and Intermediate LXV by essentially following the same procedures described for step A of Example 1.

$^1$H NMR (400 MHz, CDCl$_3$) δ 9.38 (s, 1H), 8.29 (s, 1H), 8.25 (s, 1H), 7.83 (s, 1H), 7.72 (d, 2H), 7.42 (d, 3H), 7.31 (d, 2H), 7.19 (d, 2H), 4.12 (q, 2H), 2.48-2.40 (m, 1H), 2.25 (d, 2H), 1.94-1.83 (m, 6H), 1.52 (q, 2H), 1.25 (t, 3H), 1.15 (q, 2H). MS 566.5 (M+1)$^+$.

Step B: 2-((1r,4r)-4-(4-(2-((3-(Trifluoromethoxy)phenyl)carbamoyl)imidazo[1,2-a]pyridin-6-yl)phenyl)cyclohexyl)acetic acid Compound 5 was prepared by essentially following the same procedures described for the step B of Example 1.

$^1$H NMR (400 MHz, DMSO-d$_6$) δ 7.95 (s, 1H), 7.63 (d, 2H), 7.48 (d, 3H), 7.38 (d, 2H), 7.25 (d, 3H), 7.00 (d, 1H), 6.62 (d, 1H), 2.54-2.47 (m, 1H), 2.21 (d, 2H), 1.93-1.83 (m, 6H), 1.59 (q, 2H), 1.18 (q, 2H). MS 538.0 (M+1)$^+$.

Example 6

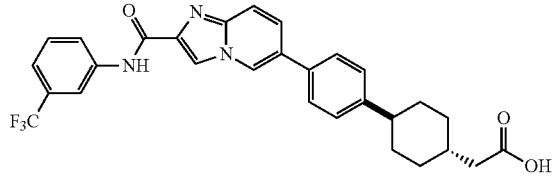

2-((1r,4r)-4-(4-(2-((3-(Trifluoromethyl)phenyl)carbamoyl)imidazo[1,2-a]pyridin-6-yl)-phenyl)cyclohexyl)acetic acid—Compound 6

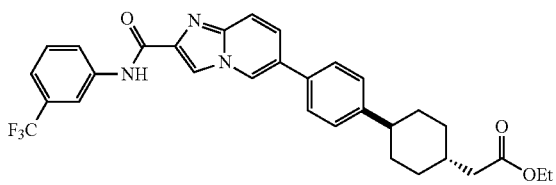

Step A: Ethyl 2-((1r,4r)-4-(4-(2-((3-(trifluoromethyl)phenyl)carbamoyl)imidazo[1,2-a]pyridin-6-yl)phenyl)cyclohexyl)acetate The title compound was prepared from Intermediate VI and Intermediate LXV by essentially following the same procedures described for step A of Example 1.

$^1$H NMR (400 MHz, CDCl$_3$) δ 9.37 (s, 1H), 8.29 (s, 1H), 8.25 (s, 1H), 8.09 (s, 1H), 7.94 (d, 1H), 7.72 (d, 2H), 7.48 (d, 3H), 7.31 (d, 1H), 7.20 (d, 2H), 4.12 (q, 2H), 2.55-2.42 (m, 1H), 2.21 (d, 2H), 1.94-1.85 (m, 6H), 1.51 (t, 2H), 1.25 (t, 3H), 1.15 (t, 2H). MS 550.2 (M+1)$^+$.

Step B: 2-((1r,4r)-4-(4-(2-((3-(Trifluoromethyl)phenyl)carbamoyl)imidazo[1,2-a]pyridin-6-yl)phenyl)cyclohexyl)acetic acid Compound 6 was prepared by essentially following the same procedures described for the step B of Example 1.

$^1$H NMR (400 MHz, DMSO-d$_6$) δ 9.15 (s, 1H), 8.92 (s, 1H), 8.29 (s, 1H), 8.27 (s, 1H), 8.02 (d, 1H), 7.96 (s, 1H), 7.69 (d, 2H), 7.61 (t, 2H), 7.49 (dd, 2H), 7.43 (d, 2H), 2.50-2.41 (m, 1H), 2.21 (d, 2H), 1.95-1.81 (m, 6H), 1.56 (q, 2H), 1.17 (q, 2H). MS 522.1 (M+1)$^+$.

Example 7

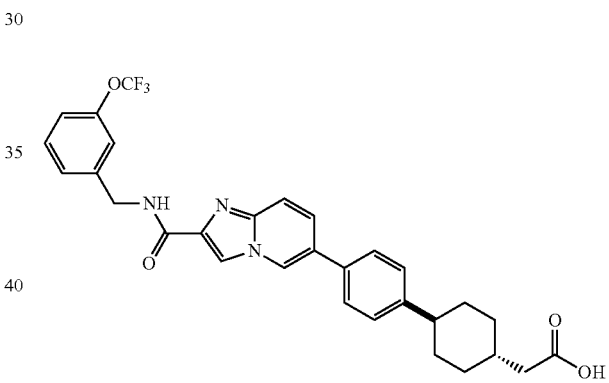

2-((1r,4r)-4-(4-(2-((3-(Trifluoromethoxy)benzyl)carbamoyl)imidazo[1,2-a]pyridin-6-yl)-phenyl)cyclohexyl)acetic acid—Compound 7

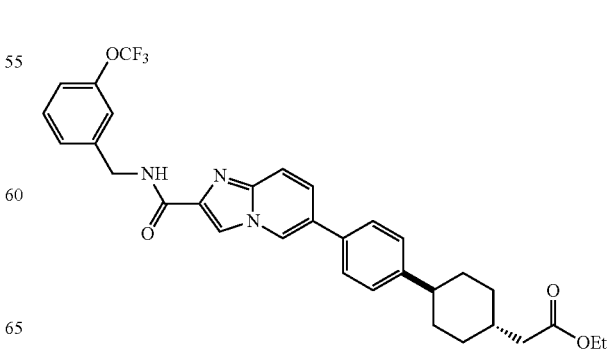

Step A: Ethyl 2-((1r,4r)-4-(4-(2-((3-(Trifluoromethoxy)benzyl)carbamoyl)imidazo[1,2-a]pyridin-6-yl)phenyl)cyclohexyl)acetate The title compound was prepared from Intermediate VII and Intermediate LXV by essentially following the same procedures described for step A of Example 1.

$^1$H NMR (400 MHz, CDCl$_3$) δ 8.29 (s, 1H), 8.21 (s, 1H), 7.77 (t, 1H), 7.59 (d, 1H), 7.48 (d, 2H), 7.35 (d, 1H), 7.32 (d, 3H), 7.22 (s, 1H), 7.13 (d, 1H), 4.69 (d, 2H), 4.15 (q, 2H), 2.53 (tt, 1H), 2.25 (d, 2H), 1.95-1.84 (m, 6H), 1.54 (qd, 2H), 1.27 (t, 3H), 1.15 (qd, 2H). MS 580.3 (M+1)$^+$.

Step B: 2-((1r,4r)-4-(4-(2-((3-(Trifluoromethoxy)benzyl)carbamoyl)imidazo[1,2-a]pyridin-6-yl)phenyl)cyclohexyl)acetic acid Compound 7 was prepared by essentially following the same procedures described for the step B of Example 1.

$^1$H NMR (400 MHz, DMSO-d$_6$) δ 9.05 (s, 1H), 8.63 (s, 1H), 8.28 (d, 1H), 7.93 (d, 1H), 7.61 (d, 2H), 7.46 (t, 2H), 7.42 (d, 2H), 7.32 (s, 1H), 7.21 (d, 1H), 4.68 (d, 2H), 2.58 (t, 1H), 2.24 (d, 2H), 1.94-1.85 (m, 6H), 1.58 (q, 2H), 1.23 (q, 2H). MS 552.4 (M+1)$^+$.

Example 8

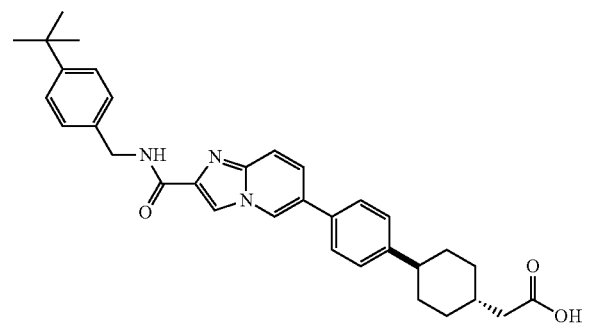

2-((1r,4r)-4-(4-(2-((4-(tert-Butyl)benzyl)carbamoyl)imidazo[1,2-a]pyridin-6-yl)phenyl)-cyclohexyl)acetic acid—Compound 8

Step A: Ethyl 2-((1r,4r)-4-(4-(2-((4-(tert-butyl)benzyl)carbamoyl)imidazo[1,2-a]pyridin-6-yl)phenyl)cyclohexyl)acetate The title compound was prepared from Intermediate VIII and Intermediate LXV by essentially following the same procedures described for step A of Example 1.

$^1$H NMR (400 MHz, CDCl$_3$) δ 8.28 (s, 1H), 8.19 (s, 1H), 7.65 (t, 1H), 7.56 (d, 1H), 7.48 (d, 2H), 7.35 (s, 2H), 7.33-7.29 (m, 5H), 4.64 (d, 2H), 4.15 (q, 2H), 2.53 (t, 1H), 2.25 (d, 2H), 1.95-1.85 (m, 5H), 1.77-1.69 (m, 1H), 1.54 (qd, 2H), 1.31 (s, 9H), 1.27 (t, 3H), 1.20-1.13 (m, 2H). MS 552.2 (M+1)$^+$.

Step B: 2-((1r,4r)-4-(4-(2-((4-(tert-Butyl)benzyl)carbamoyl)imidazo[1,2-a]pyridin-6-yl)phenyl)cyclohexyl)acetic acid Compound 8 was prepared by essentially following the same procedures described for the step B of Example 1.

$^1$H NMR (400 MHz, DMSO-d$_6$) δ 8.90 (s, 1H), 8.61 (t, 1H), 8.34 (s, 1H), 7.66 (d, 2H), 7.61 (d, 2H), 7.34 (t, 3H), 7.31 (t, 2H), 7.24 (d, 2H), 4.42 (d, 2H), 2.51 (t, 1H, overlap with DMSO peak), 2.14 (d, 2H), 1.83-1.74 (m, 6H), 1.49 (q, 2H), 1.24 (s, 9H), 1.12 (q, 2H). MS 524.1 (M+1)$^+$.

Example 9

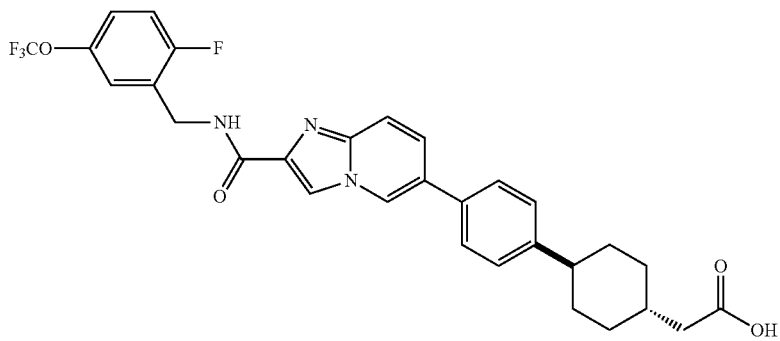

2-((1r,4r)-4-(4-(2-((2-Fluoro-5-(trifluoromethoxy)benzyl)carbamoyl)imidazo[1,2-a]pyridin-6-yl)phenyl)cyclohexyl)acetic acid—Compound 9

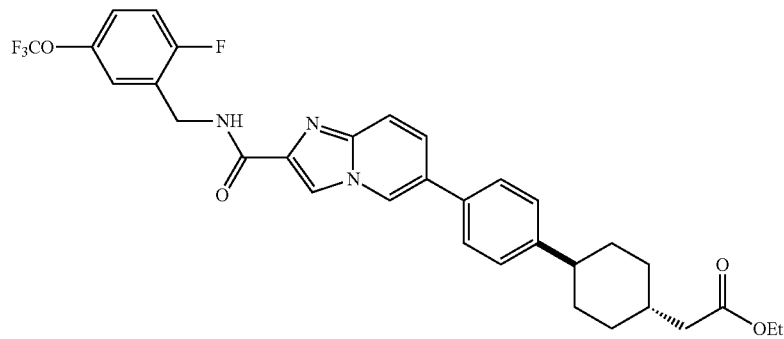

Step A: Ethyl 2-((1r,4r)-4-(4-(2-((2-fluoro-5-(trifluoromethoxy)benzyl)carbamoyl)imidazo-[1,2-a]pyridin-6-yl)phenyl)cyclohexyl)acetate The title compound was prepared from Intermediate IX and Intermediate LXV by essentially following the same procedures described for step A of Example 1.

$^1$H NMR (400 MHz, CDCl$_3$) δ 8.36 (s, 1H), 8.25 (s, 1H), 7.61 (t, 1H), 7.68 (d, 1H), 7.46 (d, 2H), 7.33-7.29 (m, 2H), 7.15-7.12 (m, 1H), 7.10 (d, 2H), 4.73 (d, 2H), 4.14 (q, 2H), 2.53 (t, 1H), 2.25 (d, 2H), 1.92-1.85 (m, 6H), 1.57-1.53 (m, 2H, overlap with water peak), 1.27 (t, 3H), 1.20-1.17 (m, 2H). MS 597.9 (M+1)$^+$.

Step B: 2-((1r,4r)-4-(4-(2-((2-Fluoro-5-(trifluoromethoxy)benzyl)carbamoyl)imidazo[1,2-a]pyridin-6-yl)phenyl)cyclohexyl)acetic acid Compound 9 was prepared by essentially following the same procedures described for the step B of Example 1.

$^1$H NMR (400 MHz, DMSO-d$_6$) δ 9.16 (t, 2H), 9.05 (s, 1H), 8.43 (s, 1H), 7.76 (s, 2H), 7.62 (d, 1H), 7.36 (d, 1H), 7.33 (d, 5H), 4.53 (d, 2H), 2.51 (m, 1H, overlap with DMSO peak), 2.13 (d, 2H), 1.83-1.80 (m, 4H), 1.73-1.71 (m, 1H), 1.63-1.61 (m, 1H), 1.49 (q, 2H), 1.12 (q, 2H). MS 569.9 (M+1)$^+$.

Example 10

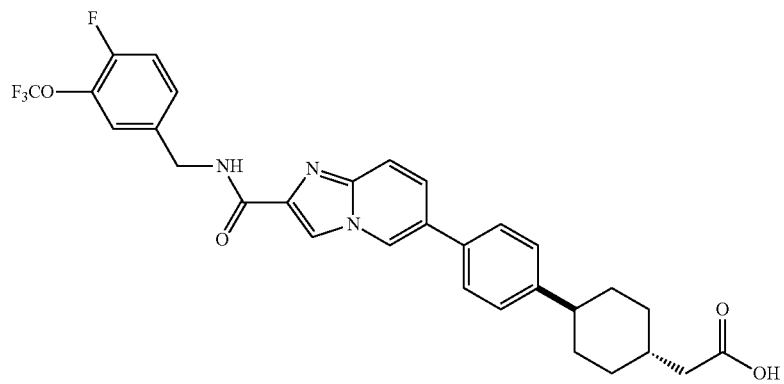

2-((1r,4r)-4-(4-(2-((4-Fluoro-3-(trifluoromethoxy)
benzyl)carbamoyl)imidazo[1,2-a]pyridin-6-yl)phe-
nyl)cyclohexyl)acetic acid—Compound 10

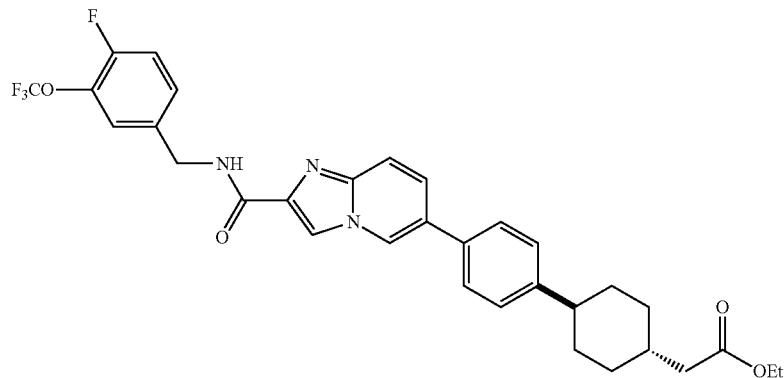

Step A: Ethyl 2-((1r,4r)-4-(4-(2-((4-fluoro-3-(trifluo-
romethoxy)benzyl)carbamoyl)imidazo[1,2-a]pyridin-
6-yl)phenyl)cyclohexyl)acetate The title compound was prepared from Intermediate X and Intermediate LXV by essentially following the same procedures described for step A of Example 1.

$^1$H NMR (400 MHz, CDCl$_3$) δ 8.29 (s, 1H), 8.20 (s, 1H), 7.75 (t, 1H), 7.59 (d, 2H), 7.32 (d, 4H), 7.16 (t, 1H), 4.64 (d, 2H), 4.15 (q, 2H), 2.53 (t, 1H), 2.23 (d, 2H), 1.92-1.87 (m, 6H), 1.53 (q, 2H), 1.27 (t, 3H), 1.18 (q, 2H). MS 598.3 (M+1)$^+$.

Step B: 2-((1r,4r)-4-(4-(2-((4-Fluoro-3-(trifluo-
romethoxy)benzyl)carbamoyl)imidazo[1,2-a]pyridin-
6-yl)phenyl)cyclohexyl)acetic acid Compound 10 was prepared by essentially following the same procedures described for the step B of Example 1.

$^1$H NMR (400 MHz, DMSO-d$_6$) δ 9.42 (s, 1H), 9.04 (s, 1H), 8.51 (s, 1H), 7.84 (s, 1H), 7.70 (d, 1H), 7.63 (d, 2H), 7.51 (d, 1H), 7.42 (d, 2H), 7.36 (d, 2H), 4.47 (d, 2H), 2.50 (m, 1H, overlap with DMSO peak), 2.13 (d, 2H), 1.88-1.79 (m, 5H), 1.73-1.66 (m, 1H), 1.48 (q, 2H), 1.16-1.03 (m, 2H). MS 570.0 (M+1)$^+$.

Example 11

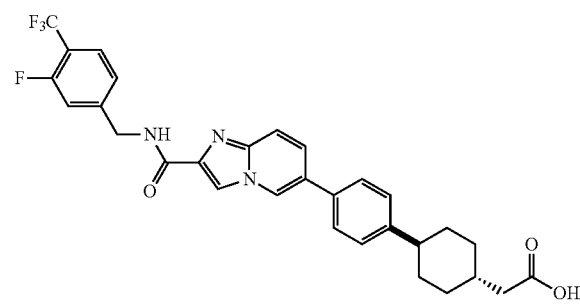

2-((1r,4r)-4-(4-(2-((3-Fluoro-4-(trifluoromethyl)ben-
zyl)carbamoyl)imidazo[1,2-a]pyridin-6-yl)phenyl)
cyclohexyl)acetic acid—Compound 11

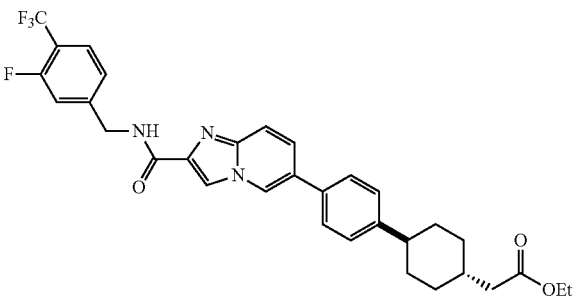

Step A: Ethyl 2-((1r,4r)-4-(4-(2-((3-fluoro-4-(trifluo-
romethyl)benzyl)carbamoyl)imidazo[1,2-a]pyridin-
6-yl)phenyl)cyclohexyl)acetate The title compound was prepared from Intermediate XI and Intermediate LXV by essentially following the same procedures described for step A of Example 1.

$^1$H NMR (400 MHz, CDCl$_3$) δ 8.28 (s, 1H), 8.21 (s, 1H), 7.99 (t, 1H), 7.58 (t, 1H), 7.53 (d, 1H), 7.47 (d, 2H), 7.31 (d, 2H), 7.23 (t, 2H), 4.69 (d, 2H), 4.14 (q, 2H), 2.53 (t, 1H), 2.24 (d, 2H), 1.92-1.85 (m, 5H), 1.73-1.69 (m, 1H), 1.53 (q, 2H), 1.25 (t, 3H), 1.17-1.13 (m, 2H). MS 582.2 (M+1)$^+$.

Step B: 2-((1r,4r)-4-(4-(2-((3-Fluoro-4-(trifluorom-
ethyl)benzyl)carbamoyl)imidazo[1,2-a]pyridin-6-yl)
phenyl)cyclohexyl)acetic acid Compound 11 was prepared by essentially following the same procedures described for the step B of Example 1.

$^1$H NMR (400 MHz, DMSO-d$_6$) δ 9.50 (s, 1H), 9.05 (s, 1H), 8.54 (s, 1H), 7.84 (d, 1H), 7.73 (t, 2H), 7.63 (d, 2H), 7.43 (d, 1H), 7.36 (d, 3H), 4.55 (d, 2H), 2.53 (m, 1H, overlap with DMSO peak), 2.13 (d, 2H), 1.82-1.79 (m, 5H), 1.73-1.72 (m, 1H), 1.48 (q, 2H), 1.11 (q, 2H). MS 554.0 (M+1)$^+$.

Example 12

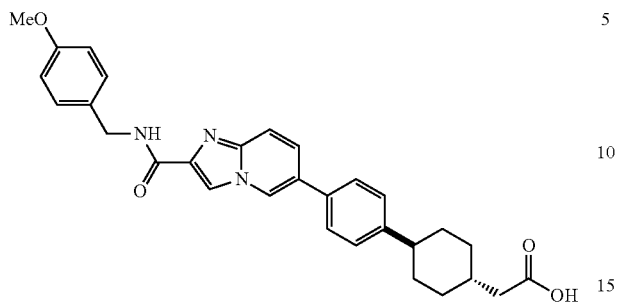

2-((1r,4r)-4-(4-(2-(4-Methoxybenzyl)carbamoyl)imidazo[1,2-a]pyridin-6-1 acetic acid—Compound 12

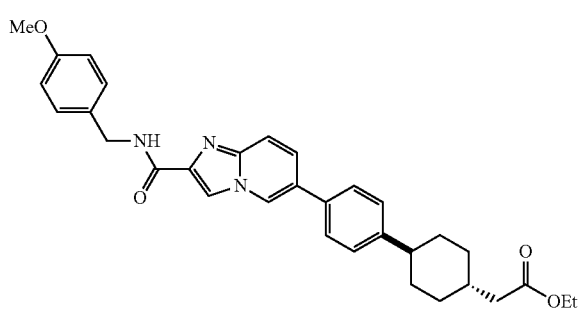

Step A: Ethyl 2-((1r,4r)-4-(4-(2-((4-methoxybenzyl)carbamoyl)imidazo[1,2-a]pyridin-6-yl)phenyl)cyclohexyl)acetate The title compound was prepared from Intermediate XII and Intermediate LXV by essentially following the same procedures described for step A of Example 1.

$^1$H NMR (400 MHz, CDCl$_3$) δ 8.35 (s, 1H), 8.24 (s, 1H), 7.65 (d, 2H), 7.48 (d, 2H), 7.31 (d, 3H), 6.88 (d, 3H), 4.61 (d, 2H), 4.15 (q, 2H), 3.80 (s, 3H), 2.53 (t, 1H), 2.25 (d, 2H), 1.93-1.86 (m, 6H), 1.53 (m, 2H, overlap with water peak), 1.26 (t, 3H), 1.17 (q, 2H). MS 526.5 (M+1)$^+$.

Step B: 2-((1r,4r)-4-(4-(2-((4-Methoxybenzyl)carbamoyl)imidazo[1,2-a]pyridin-6-yl)-phenyl)cyclohexyl)acetic acid Compound 12 was prepared by essentially following the same procedures described for the step B of Example 1.

$^1$H NMR (400 MHz, DMSO-d$_6$) δ 9.40 (s, 1H), 9.15 (s, 1H), 8.64 (s, 1H), 7.64 (d, 2H), 7.36 (d, 2H), 7.26 (d, 3H), 6.85 (d, 3H), 4.39 (d, 2H), 2.53 (m, 1H, overlap with DMSO peak), 2.13 (d, 2H), 1.81-1.78 (m, 4H), 1.72-1.71 (m, 1H), 1.61-1.58 (m, 1H), 1.47 (q, 2H), 1.10 (q, 2H). MS 498.4 (M+1)$^+$.

Example 13

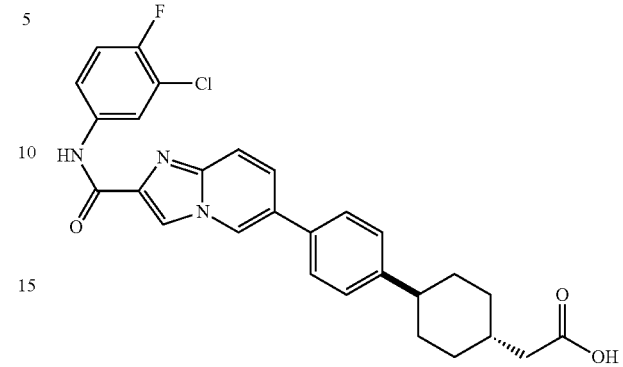

2-((1r,4r)-4-(4-(2-((3-Chloro-4-fluorophenyl)carbamoyl)imidazo[1,2-a]pyridin-6-yl)-phenyl)cyclohexyl)acetic acid—Compound 13

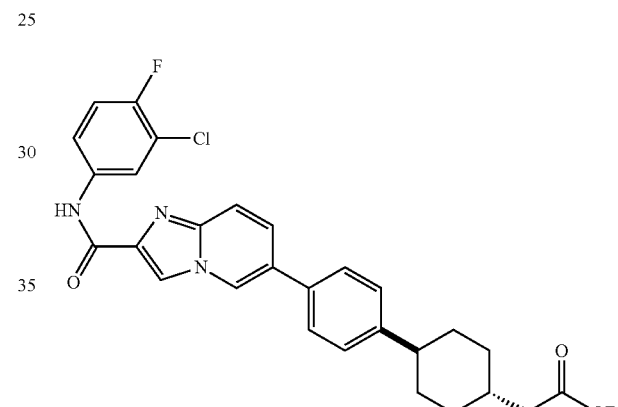

Step A: Ethyl 2-((1 r,4r)-4-(4-(2-((3-chloro-4-fluorophenyl)carbamoyl)imidazo[1,2-a]pyridin-6-yl)phenyl)cyclohexyl)acetate The title compound was prepared from Intermediate XIII and Intermediate LXV by essentially following the same procedures described for step A of Example 1.

$^1$H NMR (400 MHz, CDCl$_3$) δ 9.21 (s, 1H), 8.29 (s, 1H), 8.23 (s, 1H), 7.97 (dd, 1H), 7.63 (d, 1H), 7.54 (dd, 2H), 7.48 (d, 2H), 7.31 (d, 2H), 7.12 (t, 2H), 4.14 (d, 2H), 2.53 (t, 1H), 2.24 (d, 2H), 1.95-1.89 (m, 6H), 1.53 (m, 2H, overlap with water peak), 1.26 (t, 3H), 1.18 (q, 2H). MS 535.4 (M+1)$^+$.

Step B: 2-((1r,4r)-4-(4-(2-((3-Chloro-4-fluorophenyl)carbamoyl)imidazo[1,2-a]pyridin-6-yl)phenyl)cyclohexyl)acetic acid Compound 13 was prepared by essentially following the same procedures described for the step B of Example 1.

$^1$H NMR (400 MHz, DMSO-d$_6$) b 10.66 (s, 1H), 8.95 (s, 1H), 8.68 (s, 1H), 8.19 (dd, 1H), 7.85 (m, 1H), 7.72 (q, 2H), 7.61 (d, 2H), 7.39 (d, 1H), 7.35 (d, 2H), 2.53 (m, 1H, overlap with DMSO peak), 2.12 (d, 2H), 1.81-1.78 (m, 4H), 1.72-1.69 (m, 1H), 1.62-1.59 (m, 1H), 1.48 (q, 2H), 1.07 (q, 2H). MS 507.2 (M+1)$^+$.

Example 14

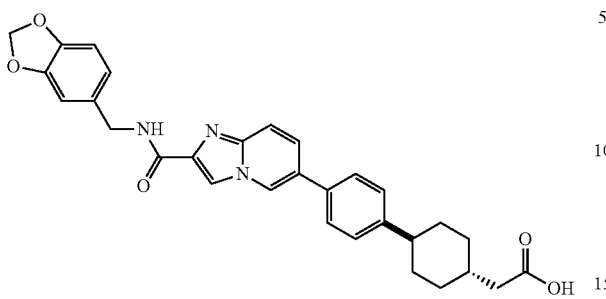

2-((1r,4r)-4-(4-(2-((Benzo[d][1,3]dioxol-5-ylmethyl)carbamoyl)imidazo[1,2-a]pyridin-6-yl)phenyl)cyclohexyl)acetic acid—Compound 14

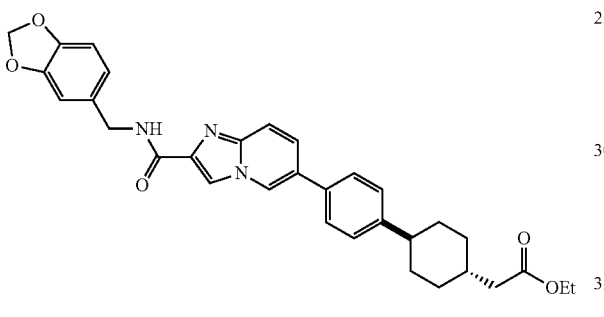

Step A: Ethyl 2-((1r,4r)-4-(4-(2-((benzo[d][1,3]dioxol-5-ylmethyl)carbamoyl)imidazo[1,2-a]pyridin-6-yl)phenyl)cyclohexyl)acetate The title compound was prepared from Intermediate XIV and Intermediate LXV by essentially following the same procedures described for step A of Example 1.

$^1$H NMR (400 MHz, CDCl$_3$) δ 8.26 (s, 1H), 8.17 (s, 1H), 7.61 (t, 1H), 7.56 (d, 1H), 7.50-7.46 (m, 3H), 7.30 (d, 2H), 6.86 (d, 1H), 6.83 (d, 1H), 6.75 (d, 1H), 5.92 (s, 2H), 4.56 (d, 2H), 4.13 (q, 2H), 2.52 (t, 1H), 2.24 (d, 2H), 1.91-1.84 (m, 6H), 1.53 (m, 2H, overlap with water peak), 1.26 (t, 3H), 1.17 (q, 2H). MS 540.2 (M+1)$^+$.

Step B: 2-((1r,4r)-4-(4-(2-((Benzo[d][1,3]dioxol-5-ylmethyl)carbamoyl)imidazo[1,2-a]pyridin-6-yl)phenyl)cyclohexyl)acetic acid Compound 14 was prepared by essentially following the same procedures described for the step B of Example 1.

$^1$H NMR (400 MHz, DMSO-d$_6$) δ 9.04 (s, 1H), 8.97 (s, 1H), 8.40 (s, 1H), 7.77 (s, 1H), 7.66 (d, 1H), 7.60 (d, 2H), 7.35 (d, 2H), 6.88 (s, 1H), 6.80 (q, 2H), 5.93 (s, 2H), 4.35 (d, 2H), 2.53 (m, 1H, overlap with DMSO peak), 2.12 (d, 2H), 1.81-1.78 (m, 4H), 1.72-1.69 (m, 1H), 1.63-1.59 (m, 1H), 1.47 (q, 2H), 1.10 (q, 2H). MS 512.6 (M+1)$^+$.

Example 15

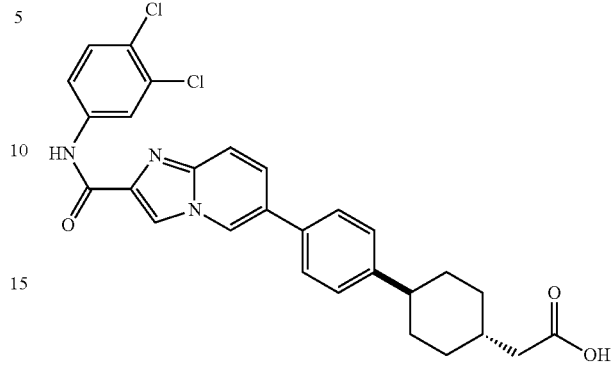

2-((1r,4r)-4-(4-(2-((3,4-Dichlorophenyl)carbamoyl)imidazo[1,2-a]pyridin-6-yl)phenyl)-cyclohexyl)acetic acid—Compound 15

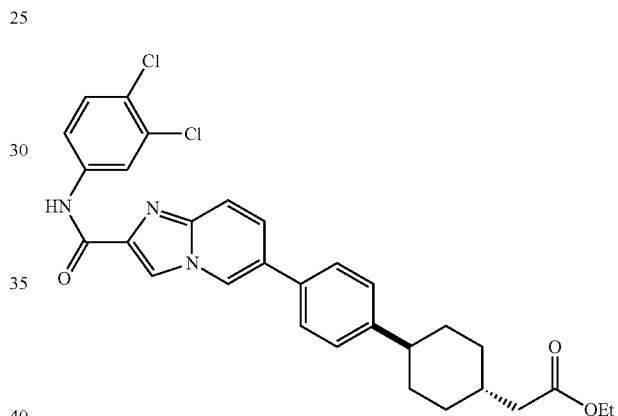

Step A: Ethyl 2-((1r,4r)-4-(4-(2-((3,4-dichlorophenyl)carbamoyl)imidazo[1,2-a]pyridin-6-yl)phenyl)cyclohexyl)acetate The title compound was prepared from Intermediate XV and Intermediate LXV by essentially following the same procedures described for step A of Example 1.

$^1$H NMR (400 MHz, CDCl$_3$) δ 9.26 (s, 1H), 8.29 (s, 1H), 8.23 (s, 1H), 8.02 (s, 1H), 7.63 (d, 1H), 7.55 (t, 2H), 7.48 (dd, 2H), 7.41 (d, 1H), 7.31 (d, 1H), 4.13 (q, 2H), 2.52 (m, 1H), 2.24 (d, 2H), 1.92-1.73 (m, 6H), 1.53 (m, 2H, overlap with water peak), 1.26 (t, 3H), 1.17 (q, 2H). MS 552.2 (M+1)$^+$.

Step B: 2-(11r,4r)-4-(4-(2-((3,4-Dichlorophenyl)carbamoyl)imidazo[1,2-a]pyridin-6-yl)phenyl)cyclohexyl)acetic acid Compound 15 was prepared by essentially following the same procedures described for the step B of Example 1.

$^1$H NMR (400 MHz, DMSO-d$_6$) δ 10.71 (s, 1H), 8.93 (s, 1H), 8.51 (s, 1H), 8.28 (d, 1H), 7.90 (d, 1H), 7.71 (s, 2H), 7.60 (d, 2H), 7.57 (d, 2H), 7.35 (d, 2H), 2.53 (m, 1H, overlap with DMSO peak), 2.12 (d, 2H), 1.81-1.78 (m, 4H), 1.72-1.69 (m, 1H), 1.62-1.59 (m, 1H), 1.48 (q, 2H), 1.11 (m, 2H). MS 523.3 (M+1)$^+$.

Example 16

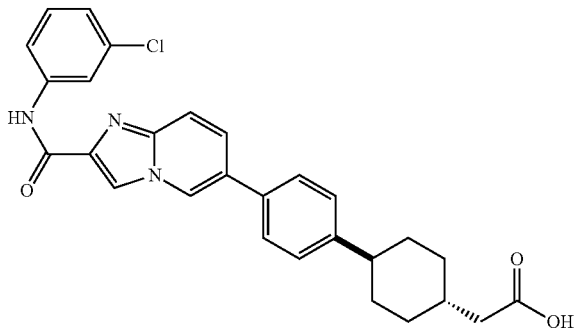

2-((1r,4r)-4-(4-(2-((3-Chlorophenyl)carbamoyl)imidazo[1,2-a]pyridin-6-yl)phenyl)cyclo-hexyl)acetic acid—Compound 16

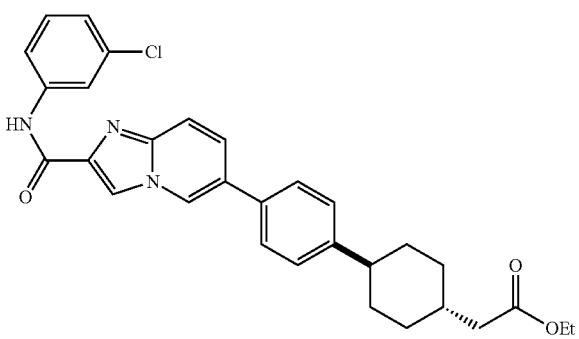

Step A: Ethyl 2-((1r,4r)-4-(4-(2-((3-chlorophenyl)carbamoyl)imidazo[1,2-a]pyridin-6-yl)phenyl)cyclohexyl)acetate The title compound was prepared from Intermediate XVI and Intermediate LXV by essentially following the same procedures described for step A of Example 1.

$^1$H NMR (400 MHz, CDCl$_3$) δ 9.27 (s, 1H), 8.28 (d, 2H), 7.91 (s, 1H), 7.64 (d, 1H), 7.57 (q, 2H), 7.49 (d, 2H), 7.32 (d, 2H), 7.25 (s, 1H), 7.10 (d, 1H), 4.14 (q, 2H), 2.53 (m, 1H), 2.25 (d, 2H), 1.95-1.82 (m, 6H), 1.55 (q, 2H), 1.25 (t, 3H), 1.17 (q, 2H). MS 517.2 (M+1)$^+$.

Step B: 2-((1r,4r)-4-(4-(2-((3-Chlorophenyl)carbamoyl)imidazo[1,2-a]pyridin-6-yl)phenyl)cyclohexyl)acetic acid Compound 16 was prepared by essentially following the same procedures described for the step B of Example 1.

$^1$H NMR (400 MHz, DMSO-d$_6$) δ 10.57 (s, 1H), 8.94 (s, 1H), 8.51 (s, 1H), 8.11 (s, 1H), 7.85 (d, 1H), 7.12 (s, 2H), 7.62 (d, 2H), 7.36 (d, 3H), 7.13 (d, 1H), 2.48 (m, 1H, overlap with DMSO peak), 2.14 (d, 2H), 1.83-1.73 (m, 6H), 1.49 (q, 2H), 1.14-1.11 (m, 2H). MS 489.2 (M+1)$^+$.

Example 17

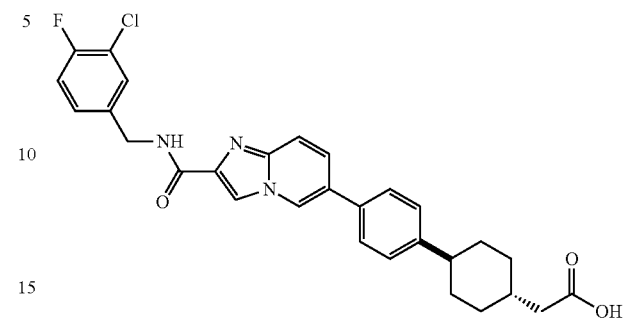

2-((1r,4r)-4-(4-(2-((3-Chloro-4-fluorobenzyl)carbamoyl)imidazo[1,2-a]pyridin-6-yl)-phenyl)cyclohexyl)acetic acid—Compound 17

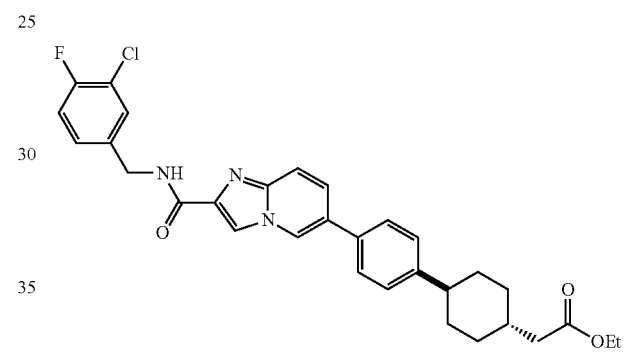

Step A: Ethyl 2-((1r,4r)-4-(4-(2-((3-chloro-4-fluorobenzyl)carbamoyl)imidazo[1,2-a]pyridin-6-yl)phenyl)cyclohexyl)acetate The title compound was prepared from Intermediate XVII and Intermediate LXV by essentially following the same procedures described for step A of Example 1.

$^1$H NMR (400 MHz, CDCl$_3$) δ 9.28 (s, 1H), 8.20 (s, 1H), 7.79 (t, 1H), 7.73 (d, 1H), 7.58 (d, 1H), 7.48 (d, 1H), 7.41 (d, 1H), 7.31 (d, 1H), 7.22 (t, 1H), 7.08 (t, 1H), 7.04 (d, 1H), 6.77 (d, 1H), 4.61 (d, 2H), 4.13 (q, 2H), 2.51 (q, 1H), 2.25 (d, 2H), 1.92-1.84 (m, 5H), 1.74-1.63 (m, 1H), 1.54 (q, 2H), 1.25 (t, 3H), 1.30-1.20 (in, 2H). MS 549.3 (M+1)$^+$.

Step B: 2-((1r,4r)-4-(4-(2-((3-Chloro-4-fluorobenzyl)carbamoyl)imidazo[1,2-a]pyridin-6-yl)phenyl)cyclohexyl)acetic acid Compound 17 was prepared by essentially following the same procedures described for the step B of Example 1.

$^1$H NMR (400 MHz, DMSO-d$_6$) δ 9.18 (s, 1H), 8.95 (s, 1H), 8.47 (s, 1H), 7.69 (s, 1H), 7.66 (d, 1H), 7.60 (d, 1H), 7.50 (d, 1H), 7.34 (d, 2H), 7.32 (d, 2H), 6.95 (d, 1H), 6.61 (d, 1H), 4.37 (d, 2H), 2.53 (m, 1H, overlap with DMSO peak), 2.11 (d, 2H), 1.81-1.78 (m, 4H), 1.72-1.68 (m, 2H), 1.47 (q, 2H), 1.06 (q, 2H). MS 521.3 (M+1)⁺.

Example 18

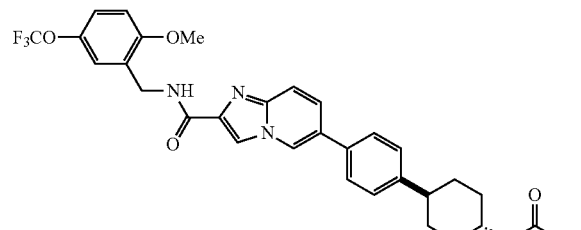

2-((1r,4r)-4-(4-(2-((2-Methoxy-5-(trifluoromethoxy)benzyl)carbamoyl)imidazo[1,2-a]-pyridin-6-yl)phenyl)cyclohexyl)acetic acid—Compound 18

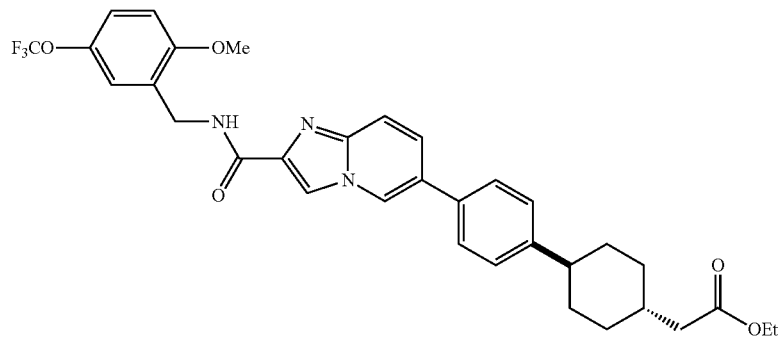

Step A: Ethyl 2-((1r,4r)-4-(4-(2-((2-methoxy-5-(trifluoromethoxy)benzyl)carbamoyl)-imidazo[1,2-a]pyridin-6-yl)phenyl)cyclohexyl)acetate The title compound was prepared from Intermediate XVIII and Intermediate LXV by essentially following the same procedures described for step A of Example 1.

¹H NMR (400 MHz, CDCl₃) δ 8.26 (t, 1H), 8.17 (s, 1H), 7.45 (t, 1H), 7.58 (d, 1H), 7.48 (dd, 1H), 7.46 (d, 2H), 7.30 (d, 2H), 7.22 (d, 1H), 7.09 (dd, 1H), 6.83 (d, 1H), 4.64 (d, 2H), 4.13 (q, 2H), 3.87 (s, 3H), 2.51 (tt, 1H), 2.23 (d, 2H), 1.86-1.82 (m, 5H), 1.65-1.63 (m, 1H), 1.54 (qd, 2H), 1.26 (t, 3H), 1.17 (q, 2H). MS 610.9 (M+1)⁺.

Step B: 2-((1r,4r)-4-(4-(2-((2-Methoxy-5-trifluoromethoxy)benzyl)carbamoyl)imidazo[1,2-a]pyridin-6-yl)phenyl)cyclohexyl)acetic acid Compound 18 was prepared by essentially following the same procedures described for the step B of Example 1.

¹H NMR (400 MHz, DMSO-d₆) δ 8.89 (s, 1H), 8.86 (t, 1H), 8.36 (s, 1H), 7.67 (s, 1H), 7.60 (d, 2H), 7.35 (d, 2H), 7.22 (dd, 1H), 7.07 (d, 1H), 4.43 (d, 2H), 3.85 (s, 3H), 2.53 (m, 1H, overlap with DMSO peak), 2.13 (d, 2H), 1.82-1.79 (m, 4H), 1.73-1.70 (m, 2H), 1.53 (q, 2H), 1.13 (q, 2H). MS 582.8 (M+1)⁺.

Example 19

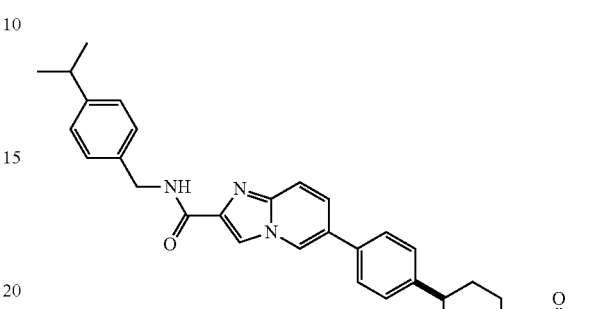

2-((1r,4r)-4-(4-(2-((4-Isopropyl)benzyl)carbamoyl)imidazo[1,2-a]pyridin-6-yl)phenyl)cyclohexyl)acetic acid—Compound 19

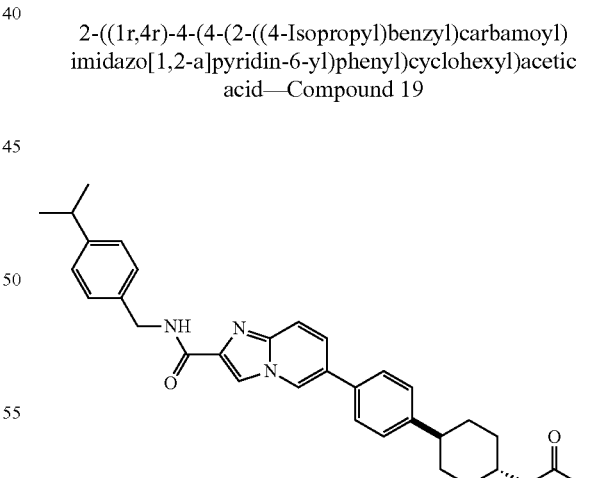

Step A: Ethyl 2-((1r,4r)-4-(4-(2-((4-isopropylbenzyl)carbamoyl)imidazo[1,2-a]pyridin-6-yl)phenyl)cyclohexyl)acetate The title compound was prepared from Intermediate XIX and Intermediate LXV by essentially following the same procedures described for step A of Example 1.

¹H NMR (400 MHz, CDCl₃) δ 8.26 (s, 1H), 8.19 (s, 1H), 7.68 (t, 1H), 7.54 (d, 1H), 7.45 (d, 3H), 7.28 (d, 3H), 7.17 (d, 2H), 4.62 (d, 2H), 4.12 (q, 2H), 2.87-2.86 (m, 1H), 2.51 (t, 1H), 2.22 (d, 2H), 1.98-1.85 (m, 5H), 1.72-1.67 (m, 1H), 1.53 (q, 2H), 1.27 (t, 3H), 1.24-1.06 (m, 8H). MS 538.8 (M+1)⁺.

Step B: 2-((1r,4r)-4-(4-(2-((4-Isopropylbenzyl)carbamoyl)imidazo[1,2-a]pyridin-6-yl)-phenyl)cyclohexyl)acetic acid Compound 19 was prepared by essentially following the same procedures described for the step B of Example 1.
¹H NMR (400 MHz, DMSO-d₆) δ 12.0 (s, 1H), 8.89 (s, 1H), 8.88 (t, 1H), 8.33 (s, 1H), 7.65 (d, 1H), 7.60 (d, 2H), 7.35 (d, 2H), 7.23 (d, 2H), 7.15 (d, 2H), 4.40 (d, 2H), 2.83 (m, 1H), 2.53 (m, 1H, overlap with DMSO peak), 2.13 (d, 2H), 1.83-1.80 (m, 4H), 1.75-1.74 (m, 1H), 1.70-1.62 (m, 1H), 1.49 (q, 2H), 1.15 (d, 6H), 1.10 (m, 2H). MS 510.8 (M+1)⁺.

Example 20

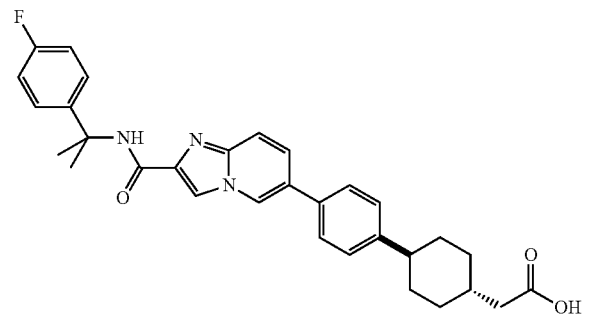

2-((1r,4r)-4-(4-(2-((2-(4-Fluorophenyl)propan-2-yl)carbamoyl)imidazo[1,2-a]pyridin-6-yl)phenyl)cyclohexyl)acetic acid—Compound 20

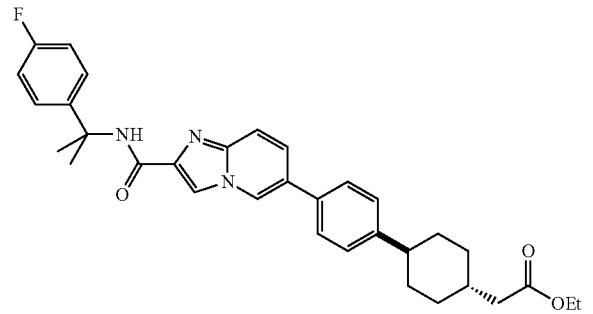

Step A: Ethyl 2-((1r,4r)-4-(4-(2-((2-(4-fluorophenyl)propan-2-yl)carbamoyl)imidazo[1,2-a]pyridin-6-yl)phenyl)cyclohexyl)acetate The title compound was prepared from Intermediate XX and Intermediate LXV by essentially following the same procedures described for step A of Example 1.
¹H NMR (400 MHz, CDCl₃) δ 8.25 (s, 1H), 8.07 (s, 1H), 7.60 (d, 1H), 7.49 (dd, 1H), 7.45 (t, 2H), 7.42 (d, 1H), 7.29 (d, 2H), 6.98 (t, 2H), 4.12 (q, 2H), 2.51-2.4 (m, 1H), 2.22 (d, 2H), 1.88-1.81 (m, 6H), 1.79 (s, 6H), 1.51 (q, 2H), 1.27 (t, 3H), 1.13 (q, 2H). MS 542.8 (M+1)⁺.

Step B: 2-((1r,4r)-4-(4-(2-((2-(4-Fluorophenyl)propan-2-yl)carbamoyl)imidazo[1,2-a]-pyridin-6-yl)phenyl)cyclohexyl)acetic acid Compound 20 was prepared by essentially following the same procedures described for the step B of Example 1.
¹H NMR (400 MHz, DMSO-d₆) δ 8.89 (s, 1H), 8.25 (s, 1H), 8.10 (s, 1H), 7.68 (s, 1H), 7.60 (d, 2H), 7.42 (d, 2H), 7.35 (d, 2H), 7.09 (t, 2H), 2.53 (m, 1H, overlap with DMSO peak), 2.13 (d, 2H), 1.83-1.75 (m, 6H), 1.70 (s, 6H), 1.49 (q, 2H), 1.14 (d, 2H). MS 514.8 (M+1)⁺.

Example 21

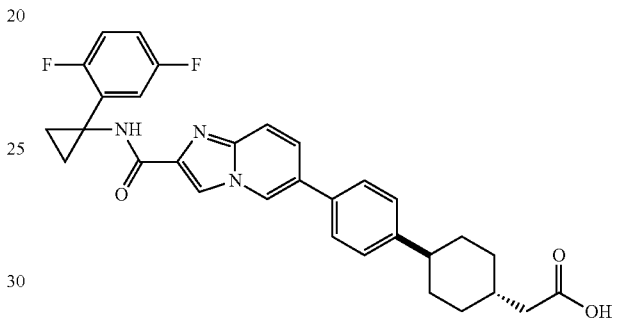

2-((1r,4r)-4-(4-(2-((1-(2,5-Difluorophenyl)cyclopropyl)carbamoyl)imidazo[1,2-a]pyridin-6-yl)phenyl)cyclohexyl)acetic acid—Compound 21

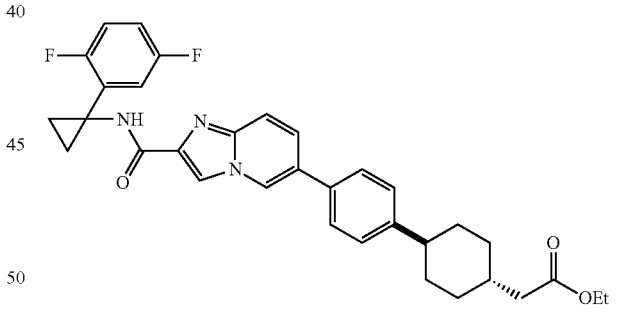

Step A: Ethyl 2-((1r,4r)-4-(4-(2-((1-(2,5-difluorophenyl)cyclopropyl)carbamoyl)imidazo-[1,2-a]pyridin-6-yl)phenyl)cyclohexyl)acetate The title compound was prepared from Intermediate XXI and Intermediate LXV by essentially following the same procedures described for step A of Example 1.
¹H NMR (400 MHz, CDCl₃) δ 8.27 (d, 1H), 8.22 (s, 1H), 8.07 (q, 3H), 7.57 (d, 1H), 7.48 (s, 1H), 7.44 (d, 2H), 7.40-7.35 (m, 1H), 7.28 (d, 2H), 6.92-6.82 (m, 2H), 4.13 (q, 2H), 2.50 (t, 1H), 2.23 (d, 2H), 1.90-1.84 (m, 5H), 1.71-1.68 (m, 1H), 1.52 (q, 2H), 1.34-1.23 (m, 7H), 1.16 (q, 2H). MS 559.0 (M+1)⁺.

Step B: 2-((1r,4r)-4-(4-(2-((1-(2,5-Difluorophenyl) cyclopropyl)carbamoyl)imidazo[1,2-a]-pyridin-6-yl) phenyl)cyclohexyl)acetic acid Compound 21 was prepared by essentially following the same procedures described for the step B of Example 1.

$^1$H NMR (400 MHz, DMSO-$d_6$) δ 8.88 (s, 1H), 8.87 (s, 1H), 8.27 (t, 2H), 7.69 (d, 1H), 7.64 (d, 1H), 7.59 (d, 2H), 7.34 (d, 2H), 7.16-7.10 (m, 2H), 2.53 (m, 1H, overlap with DMSO peak), 2.07 (d, 2H), 1.82-1.78 (m, 5H), 1.75-1.72 (m, 1H), 1.47 (q, 2H), 1.25-1.24 (m, 4H), 1.11 (q, 2H). MS 530.9 (M+1)$^+$.

Example 22

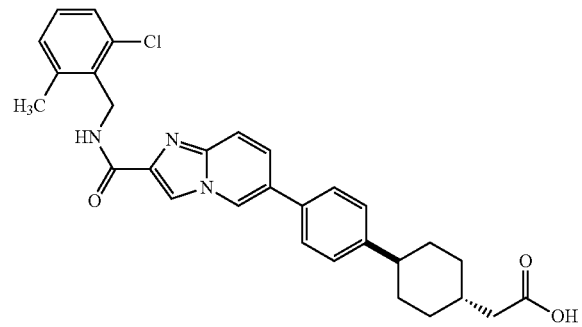

2-((1r,4r)-4-(4-(2-((2-Chloro-6-methylbenzyl)carbamoyl)imidazo[1,2-a]pyridin-6-yl)-phenyl)cyclohexyl)acetic acid—Compound 22

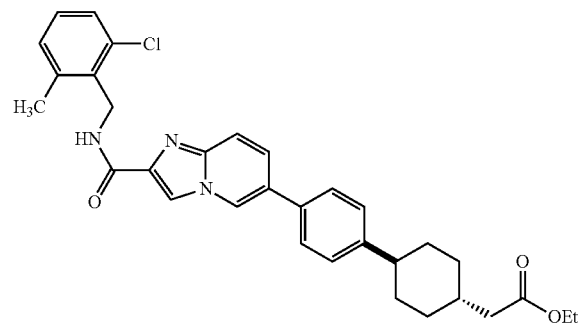

Step A: Ethyl 2-((1r,4r)-4-(4-(2-((2-chloro-6-methylbenzyl)carbamoyl)imidazo[1,2-a]-pyridin-6-yl)phenyl)cyclohexyl)acetate The title compound was prepared from Intermediate XXII and Intermediate LXV by essentially following the same procedures described for step A of Example 1.

$^1$H NMR (400 MHz, CDCl$_3$) δ 8.26 (s, 1H), 8.18 (s, 1H), 7.57 (d, 2H), 7.47 (d, 3H), 7.31 (d, 2H), 7.25 (d, 1H), 7.13 (t, 1H), 7.10 (s, 1H), 4.84 (d, 2H), 4.15 (q, 2H), 2.52 (t, 1H), 2.25 (d, 2H), 1.95-1.88 (m, 5H), 1.69-1.67 (m, 1H), 1.54 (qd, 2H), 1.27 (t, 3H), 1.18 (q, 2H). MS 545.3 (M+1)$^+$.

Step B: 2-((1r,4r)-4-(4-(2-((2-Chloro-6-methylbenzyl)carbamoyl)imidazo[1,2-a]pyridin-6-yl)phenyl) cyclohexyl)acetic acid Compound 22 was prepared by essentially following the same procedures described for the step B of Example 1.

$^1$H NMR (400 MHz, DMSO-$d_6$) δ 8.92 (s, 1H), 8.41 (s, 1H), 8.31 (s, 1H), 7.74 (d, 1H), 7.65 (d, 1H), 7.60 (d, 2H), 7.34 (d, 2H), 7.29 (d, 1H), 7.21 (t, 1H), 7.19 (s, 1H), 4.63 (d, 1H), 2.53 (m, 1H, overlap with DMSO peak), 2.13 (d, 2H), 1.82-1.78 (m, 5H), 1.75-1.64 (m, 1H), 1.47 (q, 2H), 1.11 (q, 2H). MS 517.2 (M+1)$^+$.

Example 23

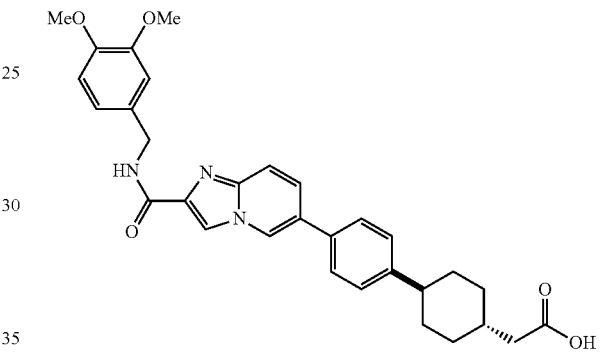

2-((1r,4r)-4-(4-(2-((3,4-Dimethoxybenzyl)carbamoyl)imidazo[1,2-a]pyridin-6-yl)phenyl)-cyclohexyl) acetic acid—Compound 23

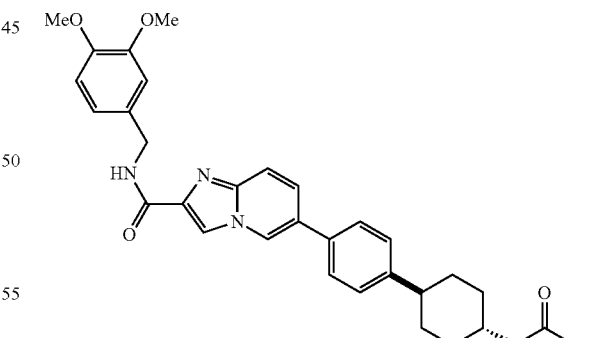

Step A: Ethyl 2-((1r,4r)-4-(4-(2-((3,4-dimethoxybenzyl)carbamoyl)imidazo[1,2-a]pyridin-6-yl)phenyl) cyclohexyl)acetate The title compound was prepared from Intermediate XXIII and Intermediate LXV by essentially following the same procedures described for step A of Example 1.

¹H NMR (400 MHz, CDCl₃) δ 8.28 (s, 1H), 8.20 (s, 1H), 7.65 (t, 1H), 7.56 (d, 1H), 7.48 (dd, 1H), 7.47 (d, 2H), 7.13 (t, 2H), 6.91 (s, 1H), 6.82 (d, 1H), 4.60 (d, 2H), 4.15 (q, 2H), 3.86 (s, 6H), 2.53 (tt, 1H), 2.25 (d, 2H), 1.95-1.85 (m, 6H), 1.54 (qd, 2H), 1.27 (t, 3H), 1.18 (qd, 2H). MS 556.3 (M+1)⁺.

Step B: 2-((1r,4r)-4-(4-(2-((3,4-Dimethoxybenzyl)carbamoyl)imidazo[1,2-a]pyridin-6-yl)-phenyl)cyclohexyl)acetic acid Compound 23 was prepared by essentially following the same procedures described for the step B of Example 1.

¹H NMR (400 MHz, DMSO-d₆) δ 9.24 (s, 1H), 9.10 (s, 1H), 8.54 (s, 1H), 7.96 (d, 1H), 7.25 (d, 1H), 7.64 (d, 2H), 7.38 (d, 2H), 6.98 (s, 1H), 6.88 (t, 2H), 4.42 (d, 2H), 3.71 (s, 6H), 2.53 (m, 1H, overlap with DMSO peak), 2.14 (d, 2H), 1.83-1.81 (m, 5H), 1.76-1.68 (m, 1H), 1.49 (q, 2H), 1.13 (q, 2H). MS 528.3 (M+1)⁺.

Example 24

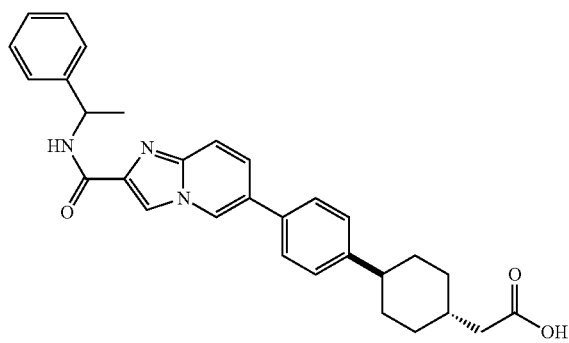

(R,S)-2-((1r,4r)-4-(4-(2-((1-Phenylethyl)carbamoyl)imidazo[1,2-a]pyridin-6-yl)phenyl)cyclo-hexyl)acetic acid—Compound 24

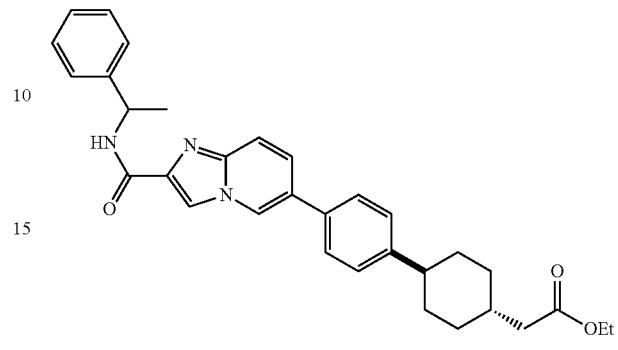

Step A: Racemic mixture of Ethyl 2-((1r,4r)-4-(4-(2-((1-phenylethyl)carbamoyl)imidazo[1,2-a]pyridin-6-yl)-phenyl)cyclohexyl)acetate The title compound was prepared from Intermediate XXIV and Intermediate LXV by essentially following the same procedures described for step A of Example 1.

¹H NMR (400 MHz, CDCl₃) δ 8.27 (s, 1H), 8.17 (s, 1H), 7.64 (t, 1H), 7.59 (d, 1H), 7.49 (dd, 1H), 7.48 (d, 2H), 7.43 (d, 2H), 7.33 (d, 4H), 7.26 (t, 1H), 5.36 (m, 1H), 4.15 (q, 2H), 2.53 (t, 1H), 2.25 (d, 2H), 1.93-1.88 (m, 6H), 1.63 (d, 3H), 1.54 (q, 2H), 1.27 (t, 3H), 1.18 (q, 2H). MS 510.3 (M+1)⁺.

Step B: (R,S)-2-((1r,4r)-4-(4-(2-((l-Phenylethyl)carbamoyl)imidazo[1,2-a]pyridin-6-yl)phenyl)-cyclohexyl)acetic acid Compound 24 was prepared by essentially following the same procedures described for the step B of Example 1.

¹H NMR (400 MHz, DMSO-d₆) δ 8.93 (s, 1H), 8.72 (s, 1H), 8.38 (s, 1H), 7.73 (s, 1H), 7.68 (s, 1H), 7.61 (d, 2H), 7.41 (d, 2H), 7.35 (d, 2H), 7.30 (t, 1H), 7.21 (t, 1H), 5.16 (m, 1H), 2.53 (m, 1H, overlap with DMSO peak), 2.13 (d, 2H), 1.83-1.80 (m, 5H), 1.79-1.75 (m, 1H), 1.50 (d, 3H), 1.47 (q, 2H), 1.12 (q, 2H). MS 482.3 (M+1)⁺.

Example 25

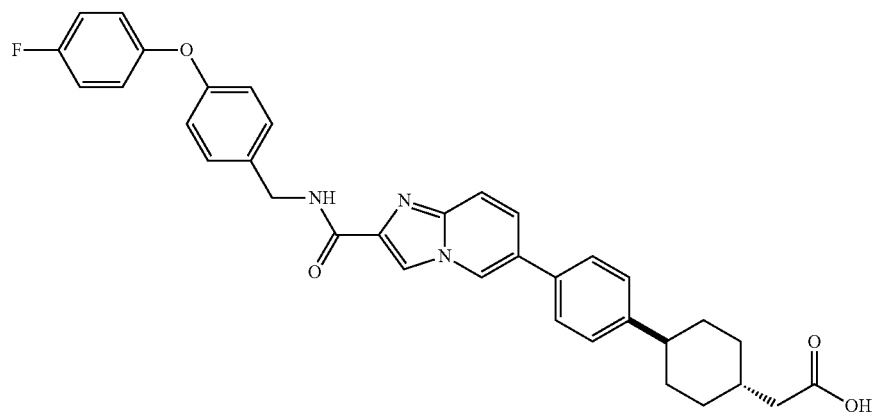

2-((1r,4r)-4-(4-(2-((4-(4-Fluorophenoxy)benzyl)carbamoyl)imidazo[1,2-a]pyridin-6-yl)-phenyl)cyclohexyl)acetic acid—Compound 25

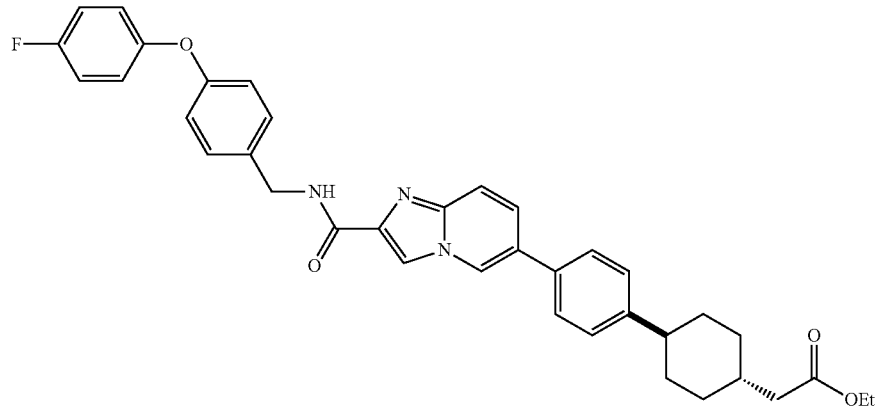

Step A: Ethyl 2-((1r,4r)-4-(4-(2-((4-(4-fluorophenoxy)benzyl)carbamoyl)imidazo[1,2-a]-pyridin-6-yl)phenyl)cyclohexyl)acetate The title compound was prepared from Intermediate XXV and Intermediate LXV by essentially following the same procedures described for step A of Example 1.

$^1$H NMR (400 MHz, CDCl$_3$) δ 8.28 (s, 1H), 8.20 (s, 1H), 7.74 (t, J=8.0 Hz, 1H), 7.69 (d, J=6.4 Hz, 1H), 7.58 (d, J=9.2 Hz, 1H), 7.48 (d, J=8.4 Hz, 2H), 7.34 (d, J=11.6 Hz, 3H), 7.21 (d, J=8.4 Hz, 2H), 7.01 (d, J=8.0 Hz, 1H), 6.97 (d, J=4.4 Hz, 1H), 6.93 (d, J=8.4 Hz, 2H), 4.65 (d, J=6.4 Hz, 2H), 4.15 (q, J=7.2 Hz, 2H), 2.51 (t, J=12.4 Hz, 1H), 2.23 (d, J=9.6 Hz, 2H), 1.93-1.81 (m, 6H), 1.53 (q, J=10.0 Hz, 2H), 1.27 (t, J=7.2 Hz, 3H), 1.17 (q, J=12.8 Hz, 2H). MS 606.3 (M+1)$^+$.

Step B: 2-((1r,4r)-4-(4-(2-((4-(4-Fluorophenoxy)benzyl)carbamoyl)imidazo[1,2-a]pyridin-6-yl)phenyl)cyclohexyl)acetic acid Compound 25 was prepared by essentially following the same procedures described for the step B of Example 1.

$^1$H NMR (400 MHz, DMSO-d$_6$) δ 9.07 (s, 1H), 8.97 (s, 1H), 8.42 (s, 1H), 7.78 (d, 1H), 7.68 (d, 1H), 7.62 (d, 2H), 7.35 (t, 3H), 7.18 (t, 2H), 7.02 (d, 1H), 7.00 (d, 1H), 6.94 (d, 2H), 4.44 (d, 2H), 2.53 (m, 1H, overlap with DMSO peak), 2.14 (d, 2H), 1.87-1.80 (m, 4H), 1.74-1.66 (m, 2H), 1.49 (d, 2H), 1.09 (q, 2H). MS 578.3 (M+1)$^+$.

Example 26

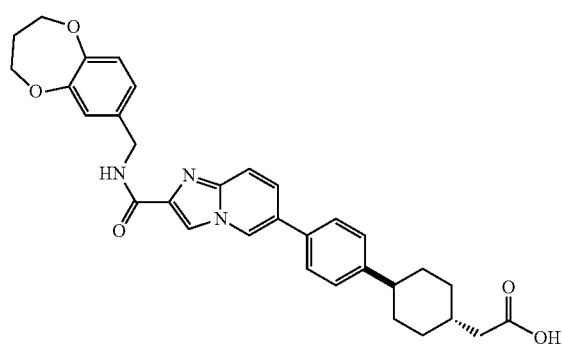

2-((1r,4r)-4-(4-(2-((3,4-Dihydro-2H-benzo[b][1,4]dioxepin-7-yl)methyl)carbamoyl)-imidazo[1,2-a]pyridin-6-yl)phenyl)cyclohexyl)acetic acid—Compound 26

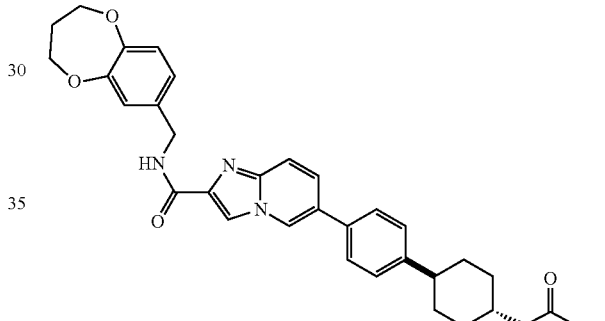

Step A: Ethyl 2-((1r,4r)-4-(4-(2-(((3,4-dihydro-2H-benzo[b][1,4]dioxepin-7-yl)methyl)-carbamoyl)imidazo[1,2-a]pyridin-6-yl)phenyl)cyclohexyl)acetate The title compound was prepared from Intermediate XXVI and Intermediate LXV by essentially following the same procedures described for step A of Example 1.

$^1$H NMR (400 MHz, CDCl$_3$) δ 8.27 (s, 1H), 8.16 (s, 1H), 7.76 (t, 1H), 7.59 (d, 1H), 7.48 (d, 1H), 7.47 (d, 2H), 7.31 (d, 2H), 7.04 (d, 1H), 6.92 (d, 1H), 6.88 (d, 1H), 4.66 (d, 2H), 4.27 (t, 2H), 4.20 (t, 2H), 4.15 (q, 2H), 2.53 (t, 1H), 2.25 (d, 2H), 2.20 (m, 2H), 1.93-1.85 (m, 6H), 1.53 (q, 2H), 1.23 (t, 3H), 1.18 (q, 2H). MS 568.3 (M+1)$^+$.

Step B: 2-((1r,4r)-4-(4-(2-(((3,4-Dihydro-2H-benzo[b][1,4]dioxepin-7-yl)methyl)carbamoyl)imidazo[1,2-a]pyridin-6-yl)phenyl)cyclohexyl)acetic acid Compound 26 was prepared by essentially following the same procedures described for the step B of Example 1.

$^1$H NMR (400 MHz, DMSO-d$_6$) δ 9.13 (s, 1H), 8.59 (s, 1H), 7.98 (s, 1H), 7.77 (d, 1H), 7.65 (d, 2H), 7.39 (d, 2H), 6.95 (m, 1H), 6.88 (s, 2H), 4.49 (m, 2H), 4.15 (m, 2H), 4.09 (m, 2H), 2.53 (m, 1H, overlap with DMSO peak), 2.14 (d, 2H), 2.12 (m, 2H), 1.84-1.81 (m, 5H), 1.76-1.72 (m, 1H), 1.49 (d, 2H), 1.13 (q, 2H). MS 540.3 (M+1)$^+$.

Example 27

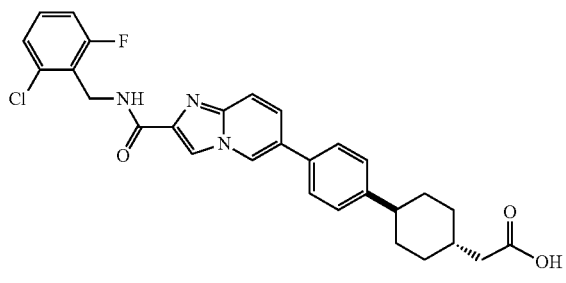

2-((1r,4r)-4-(4-(2-((2-Chloro-6-fluorobenzyl)carbamoyl)imidazo[1,2-a]pyridin-6-yl)-phenyl)cyclohexyl)acetic acid—Compound 27

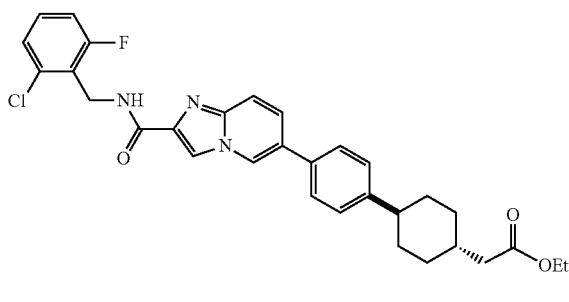

Step A: Ethyl 2-((1r,4r)-4-(4-(2-((2-chloro-6-fluorobenzyl)carbamoyl)imidazo[1,2-a]-pyridin-6-yl)phenyl)cyclohexyl)acetate The title compound was prepared from Intermediate XXVII and Intermediate LXV by essentially following the same procedures described for step A of Example 1.

$^1$H NMR (400 MHz, CDCl$_3$) δ 8.24 (s, 1H), 8.16 (s, 1H), 7.58 (d, 1H), 7.54 (s, 1H), 7.47-7.44 (m, 3H), 7.28 (d, 2H), 7.19 (d, 2H), 4.84 (d, 2H), 4.12 (q, 2H), 2.50 (t, 1H), 2.23 (d, 2H), 1.95-1.88 (m, 6H), 1.52 (q, 2H), 1.25 (t, 3H), 1.17 (q, 2H). MS 549.3 (M+1)$^+$.

Step B: 2-((1r,4r)-4-(4-(2-((2-Chloro-6-fluorobenzyl)carbamoyl)imidazo[1,2-a]pyridin-6-yl)phenyl)cyclohexyl)acetic acid Compound 27 was prepared by essentially following the same procedures described for the step B of Example 1.

$^1$H NMR (400 MHz, DMSO-d$_6$) δ 8.89 (s, 1H), 8.49 (t, 1H), 8.33 (s, 1H), 7.65 (d, 1H), 7.60 (d, 2H), 7.38-7.33 (m, 3H), 7.22 (t, 1H), 6.56 (s, 1H), 4.62 (d, 2H), 2.50 (m, 1H, overlap with DMSO peak), 2.13 (d, 2H), 1.82-1.80 (m, 6H), 1.49 (q, 2H), 1.15 (q, 2H). MS 521.2 (M+1)$^+$.

Example 28

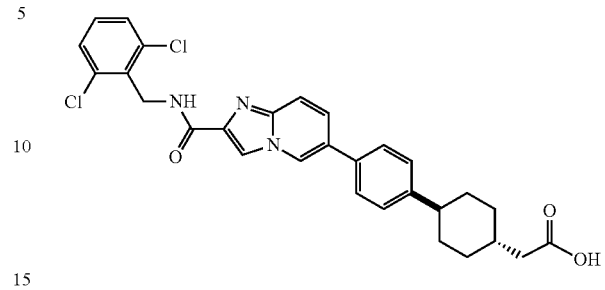

2-((1r,4r)-4-(4-(2-((2,6-Dichlorobenzyl)carbamoyl)imidazo[1,2-a]pyridin-6-yl)phenyl)-cyclohexyl)acetic acid—Compound 28

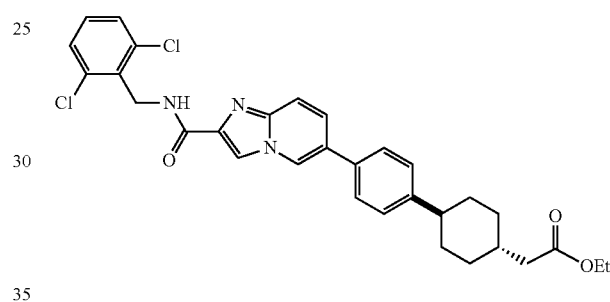

Step A: Ethyl 2-((1r,4r)-4-(4-(2-((2,6-dichlorobenzyl)carbamoyl)imidazo[1,2-a]pyridin-6-yl)phenyl)cyclohexyl)acetate The title compound was prepared from Intermediate XXVIII and Intermediate LXV by essentially following the same procedures described for step A of Example 1.

$^1$H NMR (400 MHz, CDCl$_3$) δ 8.24 (s, 1H), 8.16 (s, 1H), 7.54 (d, 2H), 7.47-7.43 (m, 3H), 7.28 (t, 4H), 7.16 (d, 1H), 4.96 (d, 2H), 4.11 (q, 2H), 2.49 (tt, 1H), 2.22 (d, 2H), 1.92-1.79 (m, 6H), 1.50 (qd, 2H), 1.24 (t, 3H), 1.14 (qd, 2H). MS 565.2 (M+1)$^+$.

Step B: 2-((1r,4r)-4-(4-(2-((2,6-Dichlorobenzyl)carbamoyl)imidazo[1,2-a]pyridin-6-yl)-phenyl)cyclohexyl)acetic acid Compound 28 was prepared by essentially following the same procedures described for the step B of Example 1.

$^1$H NMR (400 MHz, DMSO-d$_5$) δ 8.94 (s, 1H), 8.42 (s, 1H), 8.28 (s, 1H), 7.87 (d, 1H), 7.79 (d, 1H), 7.74 (d, 1H), 7.62 (d, 3H), 7.52 (d, 1H), 7.37 (d, 2H), 7.28 (d, 1H), 4.75 (d, 2H), 2.50 (m, 1H, overlap with DMSO peak), 2.15 (d, 2H), 1.84-1.74 (m, 6H), 1.50 (q, 2H), 1.12 (q, 2H). MS 537.4 (M+1)$^+$.

Example 29

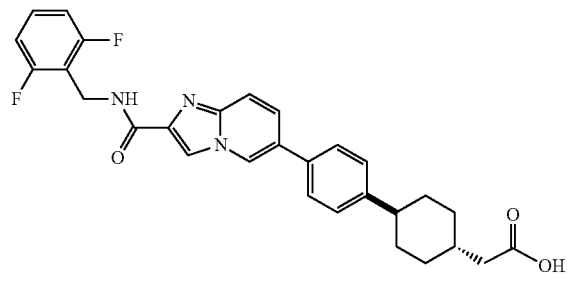

2-((1r,4r)-4-(4-(2-((2,6-Difluorobenzyl)carbamoyl)imidazo[1,2-a]pyridin-6-yl)phenyl)-cyclohexyl)acetic acid—Compound 29

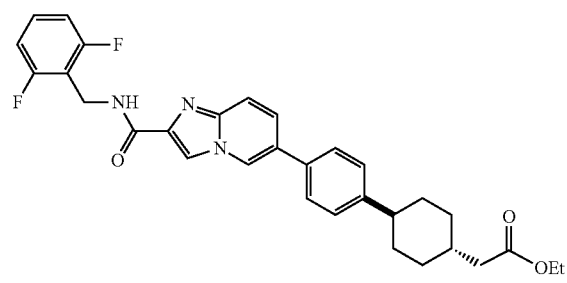

Step A: Ethyl 2-((1r,4r)-4-(4-(2-((2,6-difluorobenzyl)carbamoyl)imidazo[1,2-a]pyridin-6-yl)phenyl)cyclohexyl)acetate The title compound was prepared from Intermediate XXIX and Intermediate LXV by essentially following the same procedures described for step A of Example 1.

$^1$H NMR (400 MHz, CDCl$_3$) δ 8.24 (s, 1H), 8.15 (s, 1H), 7.64 (t, 1H), 7.55 (d, 1H), 7.47-7.42 (m, 3H), 7.27 (d, 2H), 7.21-7.17 (m, 1H), 6.89 (t, 2H), 4.74 (d, 2H), 4.11 (q, 2H), 2.49 (tt, 1H), 2.22 (d, 2H), 1.94-1.80 (m, 6H), 1.50 (qd, 2H), 1.24 (t, 3H), 1.15 (q, 2H). MS 532.3 (M+1)$^+$.

Step B: 2-((1r,4r)-4-(4-(2-((2,6-Difluorobenzyl)carbamoyl)imidazo[1,2-a]pyridin-6-yl)-phenyl)cyclohexyl)acetic acid Compound 29 was prepared by essentially following the same procedures described for the step B of Example 1.

$^1$H NMR (400 MHz, DMSO-d$_6$) δ 9.05 (s, 1H), 9.03 (s, 1H), 8.48 (s, 1H), 7.91 (d, 1H), 7.72 (d, 1H), 7.64 (d, 2H), 7.40-7.38 (m, 3H), 7.10 (t, 2H), 4.57 (d, 2H), 2.50 (m, 1H, overlap with DMSO peak), 2.15 (d, 2H), 1.90-1.81 (m, 6H), 1.51 (q, 2H), 1.16 (q, 2H). MS 504.9 (M+1)$^+$.

Example 30

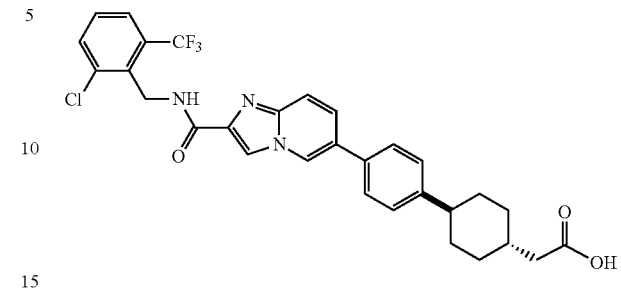

2-((1r,4r)-4-(4-(2-((2-Chloro-6-(trifluoromethyl)benzyl)carbamoyl)imidazo[1,2-a]pyridin-6-yl)phenyl)cyclohexyl)acetic acid—Compound 30

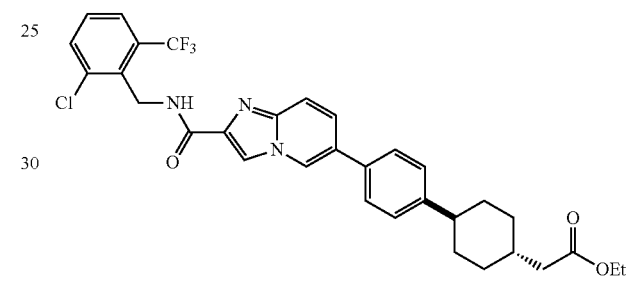

Step A: Ethyl 2-((1r,4r)-4-(4-(2-((2-chloro-6-(trifluoromethyl)benzyl)carbamoyl)imidazo-[1,2-a]pyridin-6-yl)phenyl)cyclohexyl)acetate The title compound was prepared from Intermediate XXX and Intermediate LXV by essentially following the same procedures described for step A of Example 1.

$^1$H NMR (400 MHz, CDCl$_3$) δ 8.25 (s, 1H), 8.19 (s, 1H), 7.61 (d, 2H), 7.53 (d, 1H), 7.46-7.44 (m, 4H), 7.38 (d, 1H), 7.28 (d, 2H), 4.95 (d, 2H), 4.12 (q, 2H), 2.51-2.47 (m, 1H), 2.23 (d, 2H), 1.93-1.82 (m, 6H), 1.52 (q, 2H), 1.25 (t, 3H), 1.15 (q, 2H). MS 599.3 (M+1)$^+$.

Step B: 2-((1r,4r)-4-(4-(2-((2-Chloro-6-(trifluoromethyl)benzyl)carbamoyl)imidazo[1,2-a]-pyridin-6-yl)phenyl)cyclohexyl)acetic acid Compound 30 was prepared by essentially following the same procedures described for the step B of Example 1.

$^1$H NMR (400 MHz, DMSO-d$_6$) δ 8.97 (s, 1H), 8.54 (s, 1H), 8.43 (s, 1H), 7.79 (d, 1H), 7.68 (d, 1H), 7.61 (d, 2H), 7.49 (d, 2H), 7.39-7.35 (m, 3H), 4.76 (d, 2H), 2.49 (m, 1H, overlap with DMSO peak), 2.13 (d, 2H), 1.84-1.70 (m, 6H), 1.51 (q, 2H), 1.15 (q, 2H). MS 571.2 (M+1)$^+$.

Example 31

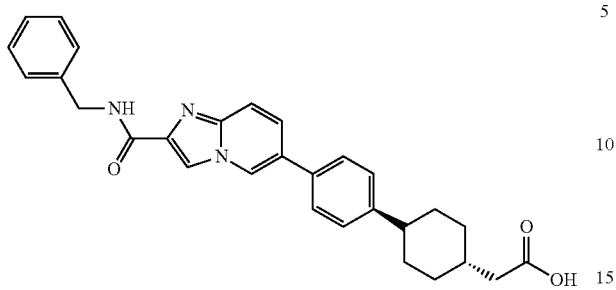

2-((1r,4r)-4-(4-(2-(Benzylcarbamoyl)imidazo[1,2-a]pyridin-6-yl)phenyl)cyclohexyl)acetic acid—Compound 31

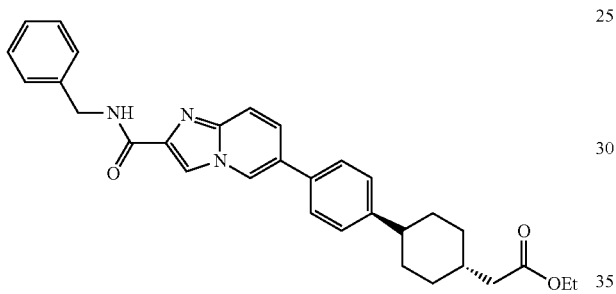

Step A: Ethyl 2-((1r,4r)-4-(4-(2-(benzylcarbamoyl)imidazo[1,2-a]pyridin-6-yl)phenyl)-cyclohexyl)acetate The title compound was prepared from Intermediate XXXI and Intermediate LXV by using procedures analogous to those described for step A of Example 1.

$^1$H NMR (400 MHz DMSO-d$_6$) δ 8.96 (t, 1H), 8.92 (1H, s), 8.36 (1H, s), 7.68-7.61 (m, 4H), 7.38-7.21 (m, 7H), 4.47 (d, 2H), 4.07 (q, 2H), 2.50 (1H, overlapped with DMSO peaks), 2.23 (d, 2H), 1.84-1.80 (m, 5H), 1.51 (q, 2H), 1.21-1.11 (m, 5H). MS 496.3 (M+1)$^+$.

Step B: 2-((1r,4r)-4-(4-(2-(Benzylcarbamoyl)imidazo[1,2-a]pyridin-6-yl)phenyl)cyclo-hexyl)acetic acid Compound 31 was prepared by using procedures analogous to those described for step B of Example 1.

$^1$H NMR (400 MHz DMSO-d$_6$) δ 9.44 (s, 1H), 9.15 (s, 1H), 8.60 (s, 1H), 7.98 (d, 1H), 7.77 (d, 1H), 7.66 (d, 2H), 7.45-7.23 (m, 7H), 4.51 (d, 2H), 2.50 (1H, overlapped with DMSO peaks), 2.15 (d, 2H), 1.85-1.72 (m, 5H), 1.51 (q, 2H), 1.13 (q, 2H). MS 468.3 (M+1)$^+$.

Example 32

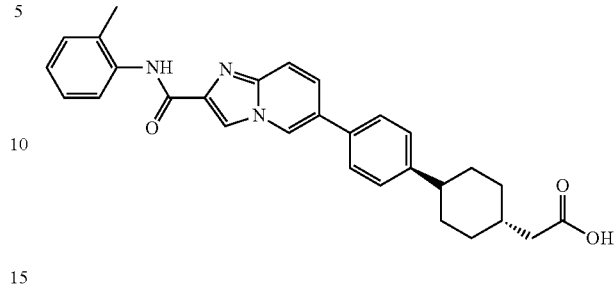

2-((1r,4r)-4-(4-(2-(o-Tolylcarbamoyl)imidazo[1,2-a]pyridin-6-yl)phenyl)cyclohexyl)acetic acid—Compound 32

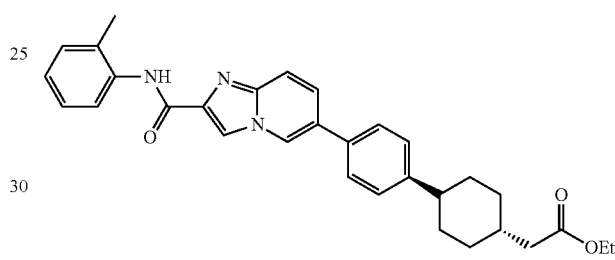

Step A: Ethyl 2-((1r,4r)-4-(4-(2-(o-tolylcarbamoyl)imidazo[1,2-a]pyridin-6-yl)phenyl)cyclohexyl)acetate The title compound was prepared from Intermediate XXXII and Intermediate LXV by using procedures analogous to those described for step A of Example 1.

$^1$H NMR (400 MHz CDCl$_3$) δ 9.23 (s, 1H), 8.31 (s, 1H), 8.28 (s, 1H), 8.21 (d, 1H), 7.66 (d, 1H), 7.55-7.50 (m, 3H), 7.33 (d, 2H), 7.29-7.26 (m, 2H), 7.09 (t, 1H), 4.15 (q, 2H), 2.55 (t, 1H), 2.46 (s, 3H), 2.26 (d, 2H), 1.97-1.91 (m, 5H), 1.55 (q, 2H), 1.28 (t, 3H), 1.20 (q, 2H). MS 496.3 (M+1)$^+$.

Step B: 2-((1r,4r)-4-(4-(2-(o-Tolylcarbamoyl)imidazo[1,2-a]pyridin-6-yl)phenyl)cyclohexyl)acetic acid Compound 32 was prepared by using procedures analogous to those described for step B of Example 1.

$^1$H NMR (400 MHz DMSO-d$_6$) δ 9.74 (s, 1H), 8.95 (s, 1H), 8.49 (s, 1H), 7.79-7.74 (m, 3H), 7.64 (d, 2H), 7.38 (d, 2H), 7.28-7.21 (m, 2H), 7.12 (t, 1H), 2.50 (1H, overlapped with DMSO peaks), 2.32 (s, 3H), 2.15 (d, 2H), 1.90-1.76 (m, 5H), 1.52 (q, 2H), 1.16 (q, 2H). MS 468.3 (M+1)$^+$.

Example 33

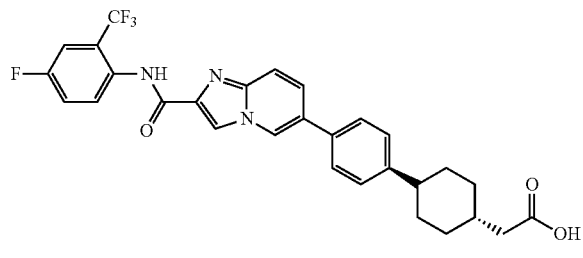

2-((1r,4r)-4-(4-(2-((4-Fluoro-2-(trifluoromethyl)phenyl)carbamoyl)imidazo[1,2-a]pyridin-6-yl)phenyl)cyclohexyl)acetic acid—Compound 33

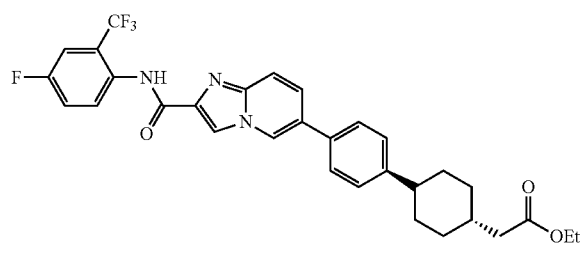

Step A: Ethyl 2-((1r,4r)-4-(4-(2-((4-fluoro-2-(trifluoromethyl)phenyl)carbamoyl)imidazo-[1,2-a]pyridin-6-yl)phenyl)cyclohexyl)acetate The title compound was prepared from Intermediate XXXIII and Intermediate LXV by using procedures analogous to those described for step A of Example 1.

$^1$H NMR (400 MHz CDCl$_3$) δ 8.39-8.36 (m, 1H), 8.31 (s, 1H), 8.27 (s, 1H), 7.71 (d, 1H), 7.58 (d, 1H), 7.49 (d, 2H), 7.39-7.28 (m, 4H), 4.14 (q, 2H), 2.56-2.50 (m, 1H), 2.04 (d, 2H), 1.95-1.85 (m, 5H), 1.54 (dq, 2H), 1.27 (t, 3H), 1.19 (q, 2H). MS 568.3 (M+1)$^+$.

Step B: 2-((1r,4r)-4-(4-(2-((4-Fluoro-2-(trifluoromethyl)phenyl)carbamoyl)imidazo[1,2-a]pyridin-6-yl)phenyl)cyclohexyl)acetic acid Compound 33 was prepared by using procedures analogous to those described for step B of Example 1.

$^1$H NMR (400 MHz DMSO-d$_6$) δ 12.09 (s, 1H), 10.00 (s, 1H), 9.00 (s, 1H), 8.10 (br s, 1H), 7.80-7.44 (m, 6H), 7.43 (d, 2H), 2.50 (1H, overlapped with DMSO peaks), 2.20 (d, 2H), 1.90-1.87 (m, 5H), 1.56 (q, 2H), 1.19 (q, 2H). MS 540.2 (M+1)$^+$.

Example 34

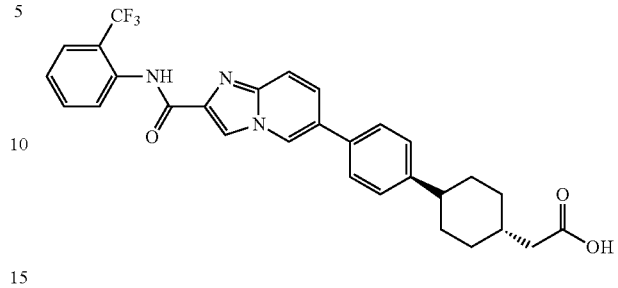

2-((1r,4r)-4-(4-(2-((2-(Trifluoromethyl)phenyl)carbamoyl)imidazo[1,2-a]pyridin-6-yl)phenyl)cyclohexyl)acetic acid—Compound 34

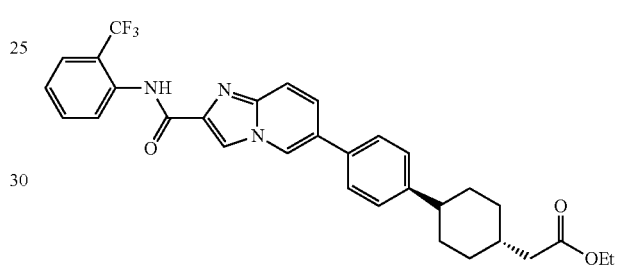

Step A: Ethyl 2-((1r,4r)-4-(4-(2-((2-(trifluoromethyl)phenyl)carbamoyl)imidazo[1,2-a]pyridin-6-yl)phenyl)cyclohexyl)acetate The title compound was prepared from Intermediate XXXIV and Intermediate LXV by using procedures analogous to those described for step A of Example 1.

$^1$H NMR (400 MHz CDCl$_3$) δ 9.82 (s, 1H), 8.53 (d, 1H), 8.31-8.30 (m, 1H), 8.27 (s, 1H), 7.71-7.52 (m, 4H), 7.50 (d, 2H), 7.33 (d, 2H), 7.26-7.22 (m, 1H), 4.15 (q, 2H), 2.58-2.51 (m, 1H), 2.26 (d, 2H), 1.97-1.89 (m, 5H), 1.59-1.51 (m, 2H), 1.27 (t, 3H), 1.19 (q, 2H). MS 550.3 (M+1)$^+$.

Step B: 2-((1r,4r)-4-(4-(2-((2-(Trifluoromethyl)phenyl)carbamoyl)imidazo[1,2-a]pyridin-6-yl)phenyl)cyclohexyl)acetic acid Compound 34 was prepared by using procedures analogous to those described for step B of Example 1.

$^1$H NMR (400 MHz DMSO-d$_6$) δ 12.09 (s, 1H), 9.98 (s, 1H), 9.01 (s, 1H), 8.61 (br s, 1H), 8.24 (d, 2H), 7.86-7.82 (m, 3H), 7.70 (d, 2H), 7.48-7.43 (m, 3H, 2.50 (1H, overlapped with DMSO peaks), 2.21 (d, 2H), 2.03-1.87 (m, 5H), 1.56 (q, 2H), 1.19 (q, 2H) MS 522.3 (M+1)$^+$.

Example 35

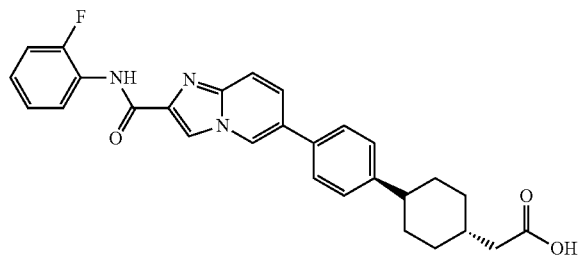

2-((1r,4r)-4-(4-(2-((2-Fluorophenyl)carbamoyl)imidazo[1,2-a]pyridin-6-yl)phenyl)cyclohexyl)acetic acid—Compound 35

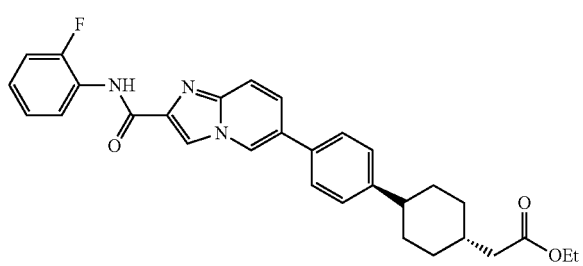

Step A: Ethyl 2-((1r,4r)-4-(4-(2-((2-fluorophenyl)carbamoyl)imidazo[1,2-a]pyridin-6-yl)phenyl)cyclohexyl)acetate The title compound was prepared from Intermediate XXXV and Intermediate LXV by using procedures analogous to those described for step A of Example 1.

$^1$H NMR (400 MHz DMSO) δ 9.87 (s, 1H), 8.96 (s, 1H), 8.54 (br s, 1H), 8.09 (br s, 1H), 7.79-7.21 (m, 9H), 4.03 (q, 2H), 2.50 (1H, overlapped with DMSO peaks), 2.24 (d, 2H), 1.88-1.75 (m, 5H), 1.48 (br s, 2H), 1.21-1.07 (m, 5H). MS 500.3 (M+1)$^+$.

Step B: 2-((1r,4r)-4-(4-(2-((2-Fluorophenyl)carbamoyl)imidazo[1,2-a]pyridin-6-yl)phenyl)cyclohexyl)acetic acid Compound 35 was prepared by using procedures analogous to those described for step B of Example 1.

$^1$H NMR (400 MHz DMSO-d$_6$) δ 12.19 (s, 1H), 9.95 (s, 1H), 8.92 (s, 1H), 8.50 (br s, 1H), 8.03 (br s, 1H), 7.75-7.18 (m, 9H), 2.50 (1H, overlapped with DMSO peaks), 2.12 (d, 2H), 1.81-1.71 (m, 5H), 1.47 (d, 2H), 1.10 (d, 2H). MS 472.2 (M+1)$^+$.

Example 36

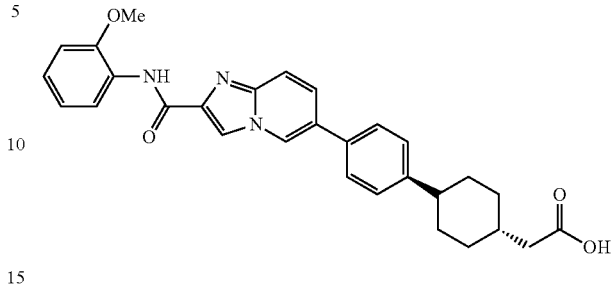

2-((1r,4r)-4-(4-(2-((2-Methoxyphenyl)carbamoyl)imidazo[1,2-a]pyridin-6-yl)phenyl)cyclohexyl)acetic acid—Compound 36

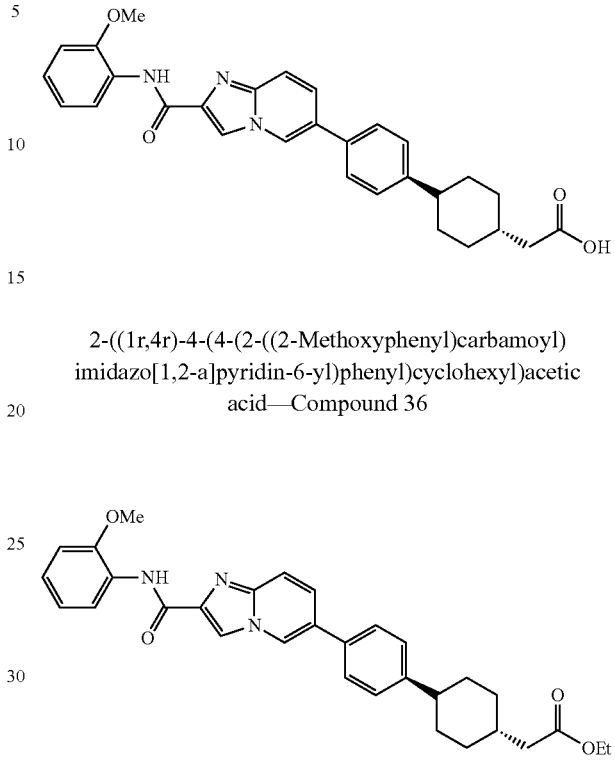

Step A: Ethyl 2-((1r,4r)-4-(4-(2-((2-methoxyphenyl)carbamoyl)imidazo[1,2-a]pyridin-6-yl)phenyl)cyclohexyl)acetate The title compound was prepared from Intermediate XXXVI and Intermediate LXV by using procedures analogous to those described for step A of Example 1.

$^1$H NMR (400 MHz CDCl$_3$) δ 9.86 (s, 1H), 8.53 (d, 1H), 8.31 (s, 1H), 8.25 (s, 1H), 7.73 (d, 1H), 7.56 (d, 1H), 7.49 (d, 2H), 7.31 (d, 2H), 7.08 (dt, 1H), 6.99 (dt, 1H), 6.93 (dd, 1H), 4.14 (q, 2H), 3.98 (s, 3H), 2.57-2.49 (m, 1H), 2.24 (d, 2H), 1.95-1.82 (m, 5H), 1.54 (dq, 2H), 1.27 (t, 3H), 1.68 (q, 2H). MS 512.3 (M+1)$^+$.

Step B: 2-((1r,4r)-4-(4-(2-((2-Methoxyphenyl)carbamoyl)imidazo[1,2-a]pyridin-6-yl)phenyl)cyclohexyl)acetic acid Compound 36 was prepared by using procedures analogous to those described for step B of Example 1.

$^1$H NMR (400 MHz DMSO-d$_6$) δ 12.00 (br s, 1H), 9.72 (s, 1H), 8.95 (s, 1H), 8.48 (s, 1H), 8.39 (d, 1H), 7.77-7.69 (m, 2H), 7.60 (d, 1H), 7.34 (d, 2H), 7.11-7.05 (m, 2H), 6.96 (t, 1H), 3.98 (s, 3H), 2.50 (1H, overlapped with DMSO peaks), 2.22 (d, 2H), 1.67-1.68 (m, 5H), 1.48 (d, 2H), 1.14 (d, 2H). MS 484.2 (M+1)$^+$.

Example 37

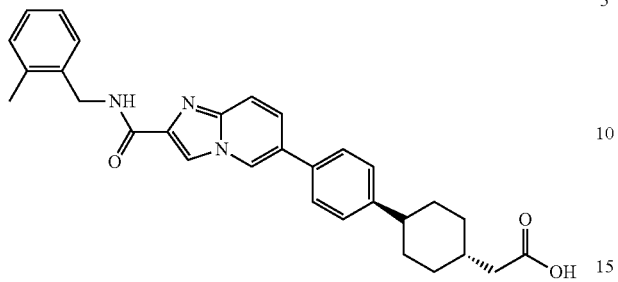

2-((1r,4r)-4-(4-(2-((2-Methylbenzyl)carbamoyl)imi-
dazo[1,2-a]pyridin-6-yl)phenyl)cyclohexyl)acetic
acid—Compound 37

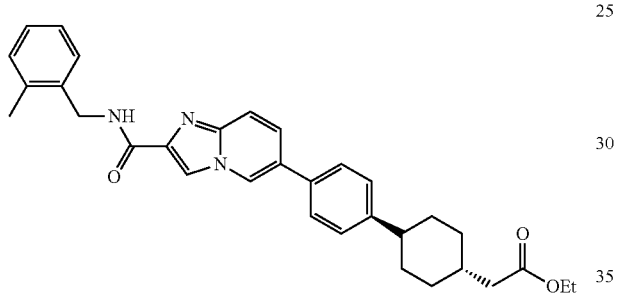

Step A: Ethyl 2-((1r,4r)-4-(4-(2-((2-methylbenzyl)carbamoyl)imidazo[1,2-a]pyridin-6-yl)phenyl)cyclohexyl)acetate The title compound was prepared from Intermediate XXX-VII and Intermediate LXV by using procedures analogous to those described for step A of Example 1.

$^1$H NMR (400 MHz CDCl$_3$) δ 8.31 (s, 1H), 8.26 (s, 1H), 7.71-7.58 (m, 2H), 7.56-7.47 (m, 3H), 7.37-7.30 (m, 3H), 7.20-7.15 (m, 3H), 4.66 (d, 2H), 4.14 (q, 2H), 2.57-2.49 (m, 1H), 2.24 (s, 3H), 2.24 (d, 2H), 1.94-1.83 (m, 5H), 1.53 (dq, 2H), 1.28 (t, 3H), 1.18 (q, 2H). MS 510.3 (M+1)$^+$.

Step B: 2-((1r,4r)-4-(4-(2-((2-Methylbenzyl)carbamoyl)imidazo[1,2-a]pyridin-6-yl)phenyl)cyclohexyl)acetic acid Compound 37 was prepared by using procedures analogous to those described for step B of Example 1.

$^1$H NMR (300 MHz DMSO-d$_6$) δ 12.10 (br s, 1H), 8.95 (s, 1H), 8.82 (t, 1H), 8.40 (s, 1H), 7.76-7.62 (m, 4H), 7.38 (d, 2H), 7.26 (br s, 1H), 7.16-7.12 (m, 3H), 4.47 (d, 2H), 2.50 (1H, overlapped with DMSO peaks), 2.34 (s, 3H), 2.16 (d, 2H), 1.86-1.71 (m, 5H), 1.51 (m, 2H), 1.14 (m, 2H). MS 482.3 (M+1)$^+$.

Example 38

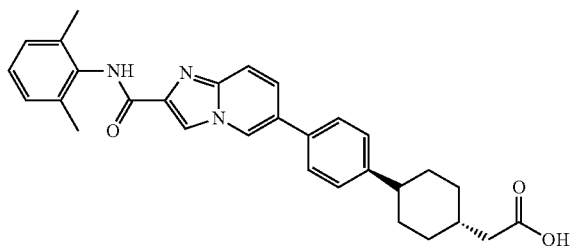

2-((1r,4r)-4-(4-(2-((2,6-Dimethylphenyl)carbamoyl)imidazo[1,2-a]pyridin-6-yl)phenyl)cyclohexyl)acetic
acid—Compound 38

Step A: Ethyl 2-((1r,4r)-4-(4-(2-((2,6-dimethylphenyl)carbamoyl)imidazo[1,2-a]pyridin-6-yl)phenyl)cyclohexyl)acetate The title compound was prepared from Intermediate XXX-VIII and Intermediate LXV by using procedures analogous to those described for step A of Example 1.

$^1$H NMR (400 MHz CDCl$_3$) δ 8.73 (s, 1H), 8.34 (s, 1H), 8.27 (s, 1H), 7.67 (d, 1H), 7.56-7.50 (m, 3H), 7.33 (d, 2H), 7.14-7.06 (m, 3H), 4.16 (q, 2H), 2.55 (t, 1H), 2.34 (s, 6H), 2.26 (d, 2H), 1.94-1.82 (m, 5H), 1.51 (d, 2H), 1.27-1.18 (m, 5H). MS 510.3 (M+1)$^+$.

Step B: 2-((1r,4r)-4-(4-(2-((2,6-Dimethylphenyl)carbamoyl)imidazo[1,2-a]pyridin-6-ylphenyl)cyclohexyl)acetic acid Compound 38 was prepared by using procedures analogous to those described for step B of Example 1.

$^1$H NMR (400 MHz DMSO-d$_6$) δ 9.91 (br s, 1H), 9.00 (br s, 1H), 8.50 (br s, 1H), 7.79-7.75 (m, 2H), 7.67-7.65 (m, 2H), 7.42-7.39 (m, 2H), 7.14-7.12 (m, 3H), 2.50 (1H, overlapped with DMSO peaks), 2.22-2.15 (m, 8H), 1.84-1.72 (m, 5H), 1.53 (m, 2H), 1.15 (m, 2H). MS 482.3 (M+1)$^+$.

Example 39

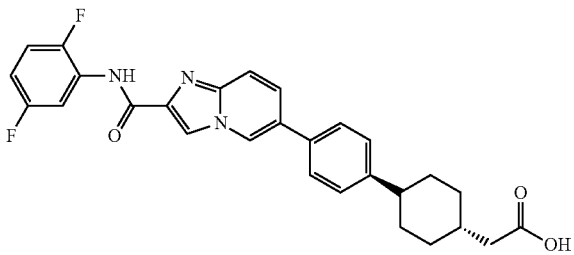

2-((1r,4r)-4-(4-(2-((2,5-Difluorophenyl)carbamoyl)imidazo[1,2-a]pyridin-6-yl)phenyl)cyclohexyl)acetic acid—Compound 39

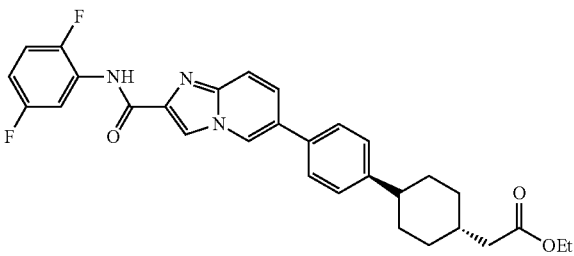

Step A: Ethyl 2-((1r,4r)-4-(4-(2-((2,5-difluorophenyl)carbamoyl)imidazo[1,2-a]pyridin-6-yl)phenyl)cyclohexyl)acetate The title compound was prepared from Intermediate XXXIX and Intermediate LXV by using procedures analogous to those described for step A of Example 1.

$^1$H NMR (400 MHz CDCl$_3$) δ 9.57 (s, 1H), 8.42-8.37 (m, 1H), 8.31 (s, 1H), 8.27 (s, 1H), 7.68 (d, 1H), 7.55 (d, 1H), 7.50 (d, 2H), 7.33 (d, 2H), 7.09 (m, 1H), 6.76 (m, 1H), 4.15 (q, 2H), 2.55 (t, 1H), 2.26 (d, 2H), 2.00-1.83 (m, 5H), 1.57-1.48 (m, 2H), 1.31-1.18 (m, 5H). MS 518.2 (M+1)$^+$.

Step B: 2-((1r,4r)-4-(4-(2-((2,5-Difluorophenyl)carbamoyl)imidazo[1,2-a]pyridin-6-yl)phenyl)cyclohexyl)acetic acid Compound 39 was prepared by using procedures analogous to those described for step B of Example 1.

$^1$H NMR (400 MHz DMSO-d$_6$) δ 9.91 (s, 1H), 8.96 (s, 1H), 8.57 (br s, 1H), 8.01 (br s, 1H), 7.78-7.64 (m, 4H), 7.48-7.34 (m, 3H), 7.06 (br s, 1H), 2.50 (1H, overlapped with DMSO peaks), 2.24-2.16 (m, 2H), 1.89-1.72 (m, 5H), 1.51 (m, 2H), 1.15 (m, 2H). MS 490.2 (M+1)$^+$.

Example 40

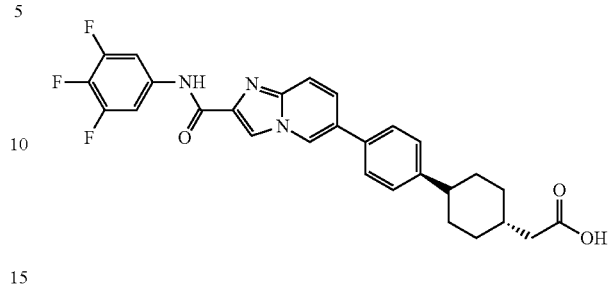

2-((1r,4r)-4-(4-(2-((3,4,5-Trifluorophenyl)carbamoyl)imidazo[1,2-a]pyridin-6-yl)phenyl)cyclohexyl)acetic acid—Compound 40

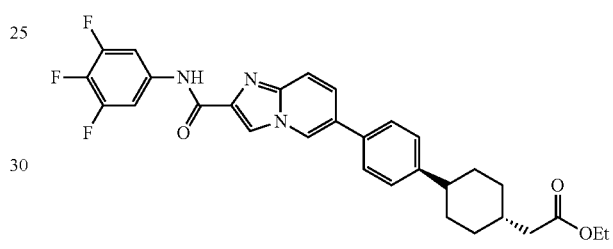

Step A: Ethyl 2-((1r,4r)-4-(4-(2-((3,4,5-trifluorophenyl)carbamoyl)imidazo[1,2-a]pyridin-6-yl)phenyl)cyclohexyl)acetate The title compound was prepared from Intermediate XL and Intermediate LXV by using procedures analogous to those described for step A of Example 1.

$^1$H NMR (400 MHz CDCl$_3$) δ 9.25 (s, 1H), 8.31 (s, 1H), 8.26 (s, 1H), 7.64 (d, 1H), 7.55 (dd, 1H), 7.52-7.48 (m, 4H), 7.33 (d, 2H), 4.14 (q, 2H), 2.53 (t, 1H), 2.26 (d, 2H), 1.94-1.91 (m, 5H), 1.58 (q, 2H), 1.30-1.21 (m, 5H). MS 536.3 (M+1)$^+$.

Step B: 2-((1r,4r)-4-(4-(2-((3,4,5-Trifluorophenyl)carbamoyl)imidazo[1,2-a]pyridin-6-yl)phenyl)cyclohexyl)acetic acid Compound 40 was prepared by using procedures analogous to those described for step B of Example 1.

$^1$H NMR (400 MHz DMSO-d$_6$) δ 10.87 (br s, 1H), 8.98 (br s, 1H), 8.57 (br s, 1H), 7.97-7.94 (m, 2H), 7.76-7.64 (m, 4H), 7.42-7.36 (m, 3H), 2.50 (1H, overlapped with DMSO peaks), 2.24-2.16 (m, 2H), 1.88-1.72 (m, 5H), 1.52 (m, 2H), 1.18 (m, 2H). MS 508.2 (M+1)$^+$.

Example 41

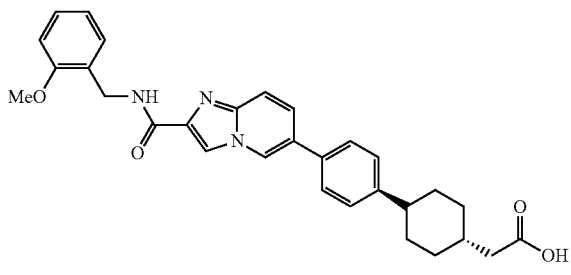

2-((1r,4r)-4-(4-(2-((2-Methoxybenzyl)carbamoyl)imidazo[1,2-a]pyridin-6-yl)phenyl)cyclohexyl)acetic acid—Compound 41

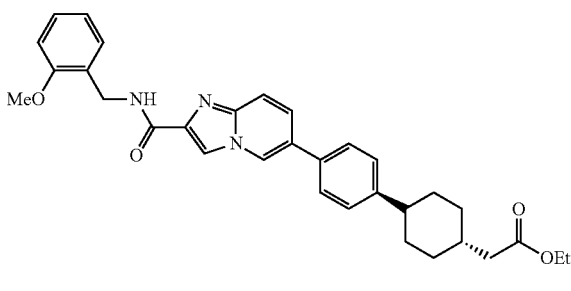

Step A: Ethyl 2-((1r,4r)-4-(4-(2-((2-methoxybenzyl)carbamoyl)imidazo[1,2-a]pyridin-6-yl)phenyl)cyclohexyl)acetate The title compound was prepared from Intermediate XLI and Intermediate LXV by using procedures analogous to those described for step A of Example 1.

$^1$H NMR (400 MHz CDCl$_3$) δ 8.27 (s, 1H), 8.18 (s, 1H), 7.76 (t, 1H), 7.59 (d, 1H), 7.50-7.47 (m, 3H), 7.38 (d, 1H), 7.24 (m, 1H), 7.31 (d, 2H), 6.94-6.88 (m, 2H), 4.68 (d, 2H), 4.15 (q, 2H), 3.90 (s, 3H), 2.54 (t, 1H), 2.26 (d, 2H), 1.96-1.89 (m, 5H), 1.54 (q, 2H), 1.30-1.18 (m, 5H). MS 526.2 (M+1)$^+$.

Step B: 2-((1r,4r)-4-(4-(2-((2-Methoxybenzyl)carbamoyl)imidazo[1,2-a]pyridin-6-yl)phenyl)cyclohexyl)acetic acid Compound 41 was prepared by using procedures analogous to those described for step B of Example 1.

$^1$H NMR (400 MHz CD$_3$OD+CDCl$_3$) δ 8.70 (s, 1H), 8.34 (br s, 1H), 7.86 (br s, 1H), 7.70-7.56 (m, 4H), 7.35-7.26 (m, 4H), 7.00-6.90 (m, 2H), 2.54 (br s, 1H), 2.13-2.11 (m, 2H), 1.97-1.80 (m, 5H), 1.57 (q, 2H), 1.21 (q, 2H). MS 498.3 (M+1)$^+$.

Example 42

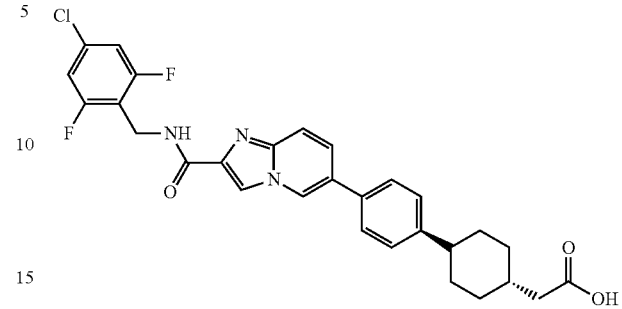

2-((1s,4s)-4-(4-(2-((4-chloro-2,6-difluorobenzyl)carbamoyl)imidazo[1,2-a]pyridin-6-yl)phenyl)cyclohexyl)acetic acid—Compound 42

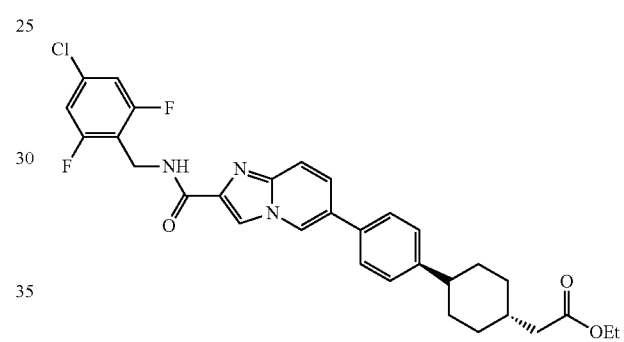

Step A: Ethyl 2-((1s,4s)-4-(4-(2-((4-Chloro-2,6-difluorobenzyl)carbamoyl)imidazo[1,2-a]pyridin-6-yl)phenyl)cyclohexyl)acetate The title compound was prepared from Intermediate XLII and Intermediate LXV by using procedures analogous to those described for step A of Example 1.

$^1$H NMR (400 MHz CDCl$_3$) δ 8.29 (s, 1H), 8.18 (s, 1H), 7.68-7.61 (m, 1H), 7.60-7.53 (m, 1H), 7.48 (d, 2H), 7.32 (d, 2H), 6.99-6.20 (m, 2H), 4.73 (d, 2H), 4.15 (q, 2H), 2.59-2.48 (m, 1H), 2.98-2.20 (m, 2H), 1.98-1.82 (m, 5H), 1.60-1.48 (m, 2H), 1.30-1.11 (m, 5H).

Step B: 2-((1s,4s)-4-(4-(2-((4-Chloro-2,6-difluorobenzyl)carbamoyl)imidazo[1,2-a]pyridin-6-yl)phenyl)cyclohexyl)acetic acid Compound 42 was prepared by using procedures analogous to those described for step B of Example 1.

$^1$H NMR (400 MHz DMSO-d$_6$) δ 8.91 (s, 1H), 8.79 (t, 1H), 8.33 (s, 1H), 7.71-7.59 (m, 4H), 7.42-7.30 (m, 4H), 4.50 (d, 2H), 2.50 (1H, overlapped with DMSO peaks), 2.14 (d, 2H), 1.90-1.69 (m, 5H), 1.50 (q, 2H), 1.13 (q, 2H).

Example 43

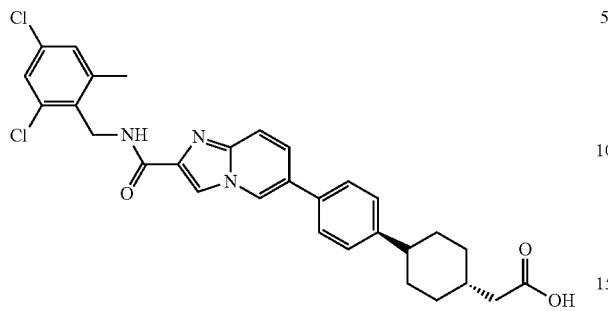

2-((1s,4s)-4-(4-(2-((2,4-Dichloro-6-methylbenzyl)carbamoyl)imidazo[1,2-a]pyridin-6-yl)phenyl)cyclohexyl)acetic acid—Compound 43

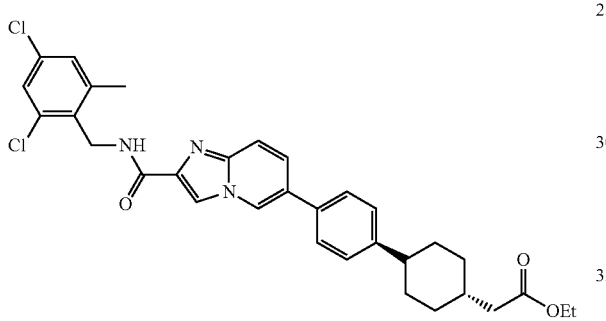

Step A: Ethyl 2-((1s,4s)-4-(4-(2-((2,4-dichloro-6-methylbenzyl)carbamoyl)imidazo[1,2-a]pyridin-6-yl)phenyl)cyclohexyl)acetate The title compound was prepared from Intermediate XLIII and Intermediate LXV by using procedures analogous to those described for step A of Example 1.

$^1$H NMR (400 MHz CDCl$_3$) δ 8.30 (s, 1H), 8.19 (s, 1H), 7.70-7.54 (m, 2H), 7.48 (d, 2H), 7.33 (d, 2H), 7.29-7.24 (m, 2H), 7.11 (d, 1H), 4.79 (d, 2H), 4.15 (q, 2H), 2.58-2.48 (m, 4H), 2.25 (d, 2H), 1.98-1.82 (m, 5H), 1.62-1.48 (m, 2H), 1.31-1.12 (m, 5H).

Step B: 2-((1s,4s)-4-(4-(2-((2,4-Dichloro-6-methylbenzyl)carbamoyl)imidazo[1,2-a]pyridin-6-yl)phenyl)cyclohexyl)acetic acid Compound 43 was prepared by using procedures analogous to those described for step B of Example 1.

$^1$H NMR (400 MHz DMSO-d$_6$) δ 8.92-8.89 (m, 1H), 8.38-8.32 (m, 2H), 7.71-7.58 (m, 4H), 7.48-7.44 (m, 1H), 7.39-7.30 (m, 3H), 4.60 (d, 2H), 2.50 (1H, overlapped with DMSO peaks), 2.48 (s, 3H), 2.14 (d, 2H), 1.90-1.70 (m, 5H), 1.50 (q, 2H), 1.43 (q, 2H).

Example 44

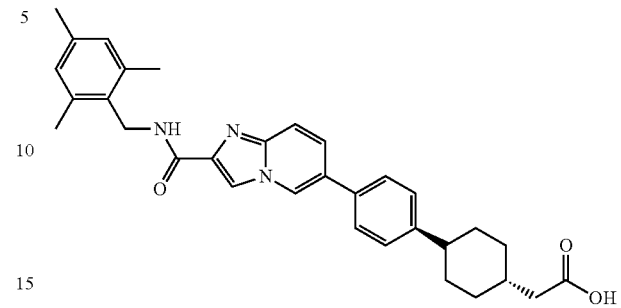

2-((1s,4s)-4-(4-(2-((2,4,6-Trimethylbenzyl)carbamoyl)imidazo[1,2-a]pyridin-6-yl)phenyl)cyclohexyl)acetic acid—Compound 44

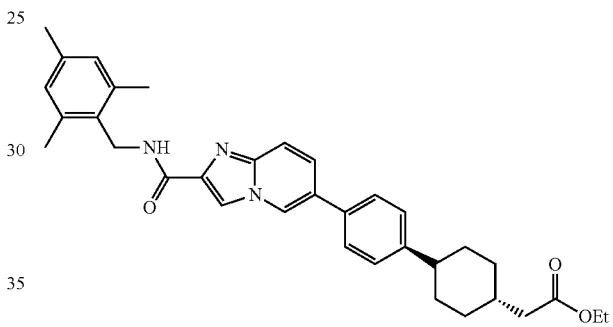

Step A: Ethyl 2-((1s,4s)-4-(4-(2-((2,4,6-trimethylbenzyl)carbamoyl)imidazo[1,2-a]pyridin-6-yl)phenyl)cyclohexyl)acetate The title compound was prepared from Intermediate XLIV and Intermediate LXV by using procedures analogous to those described for step A of Example 1.

$^1$H NMR (400 MHz CDCl$_3$) δ 8.90-8.80 (m, 1H), 8.20-8.18 (m, 1H), 7.58-7.52 (m, 1H), 7.51-7.45 (m, 3H), 7.32 (d, 2H), 7.21 (br s, 1H), 6.90-6.87 (s, 2H), 4.66 (d, 2H), 4.15 (q, 2H), 2.58-2.48 (m, 1H), 2.39 (s, 6H), 2.30-2.22 (m, 5H), 1.99-1.82 (m, 5H), 1.61-1.48 (m, 2H), 1.31-1.12 (m, 5H).

Step B: 2-((1s,4s)-4-(4-(2-((2,4,6-Trimethylbenzyl)carbamoyl)imidazo[1,2-a]pyridin-6-yl)phenyl)cyclohexyl)acetic acid Compound 44 was prepared by using procedures analogous to those described for step B of Example 1.

$^1$H NMR (400 MHz DMSO-d$_6$) δ 12.08 (br s, 1H), 8.92-8.89 (m, 1H), 8.35 (s, 1H), 7.99 (t, 1H), 7.73-7.58 (m, 4H), 7.36 (d, 2H), 6.84 (s, 2H), 4.48 (d, 2H), 2.50 (1H, overlapped with DMSO peaks), 2.34 (s, 6H), 2.21 (s, 3H), 2.15 (d, 2H), 1.90-1.68 (m, 5H), 1.50 (q, 2H), 1.14 (q, 2H).

Example 45

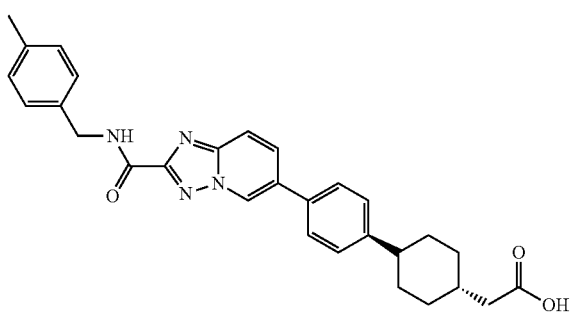

2-((1s,4s)-4-(4-(2-((4-Methylbenzyl)carbamoyl)-[1,2,4]triazolo[1,5-a]pyridin-6-yl)phenyl)cyclohexyl)acetic acid—Compound 45

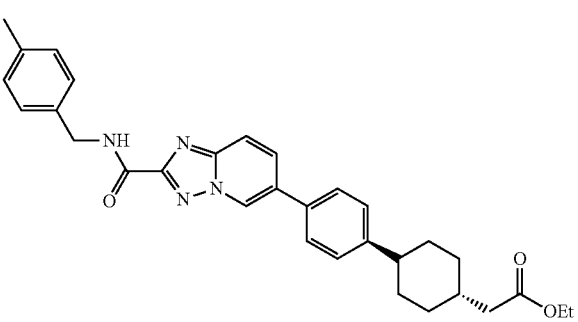

Step A: Ethyl 2-((1s,4s)-4-(4-(2-((4-methylbenzyl)carbamoyl)-[1,2,4]triazolo[1,5-a]pyridin-6-yl)phenyl)cyclohexyl)acetate The title compound was prepared from Intermediate XLV and Intermediate LXV by using procedures analogous to those described for step A of Example 1.

$^1$H NMR (400 MHz CDCl$_3$) δ 8.77 (s, 1H), 7.86-7.74 (m, 2H), 7.65-7.59 (t, 1H), 7.50 (d, 2H), 7.35 (d, 2H), 7.28 (d, 2H), 7.16 (d, 2H), 4.69 (d, 2H), 4.15 (q, 2H), 2.59-2.49 (m, 1H), 2.35 (s, 3H), 2.26 (d, 2H), 1.99-1.82 (m, 5H), 1.62-1.48 (m, 2H), 1.31-1.12 (m, 5H).

Step B: 2-((1s,4s)-4-(4-(2-((4-methylbenzyl)carbamoyl)-[1,2,4]triazolo[1,5-a]pyridin-6-yl)phenyl)cyclohexyl)acetic acid Compound 45 was prepared by using procedures analogous to those described for step B of Example 1.

$^1$H NMR (400 MHz DMSO-d$_6$) δ 9.35 (t, 1H), 9.32-9.28 (m, 1H), 8.10 (dd, 1H), 7.96 (d, 1H), 7.72 (d, 2H), 7.39 (d, 2H), 7.23 (d, 2H), 7.13 (d, 2H), 4.45 (d, 2H), 2.50 (1H, overlapped with DMSO peaks), 2.33 (s, 3H), 2.14-2.06 (m, 2H), 1.89-1.69 (m, 5H), 1.51 (q, 2H), 1.13 (q, 2H).

Example 46

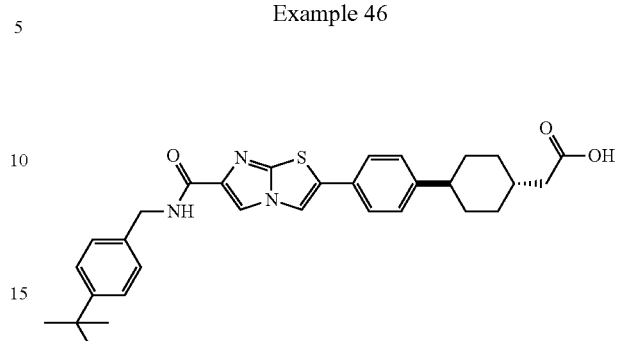

2-((1r,4r)-4-(4-(6-((4-(tert-Butyl)benzyl)carbamoyl)imidazo[2,1-b]thiazol-2-yl)phenyl)-cyclohexyl)acetic acid—Compound 46

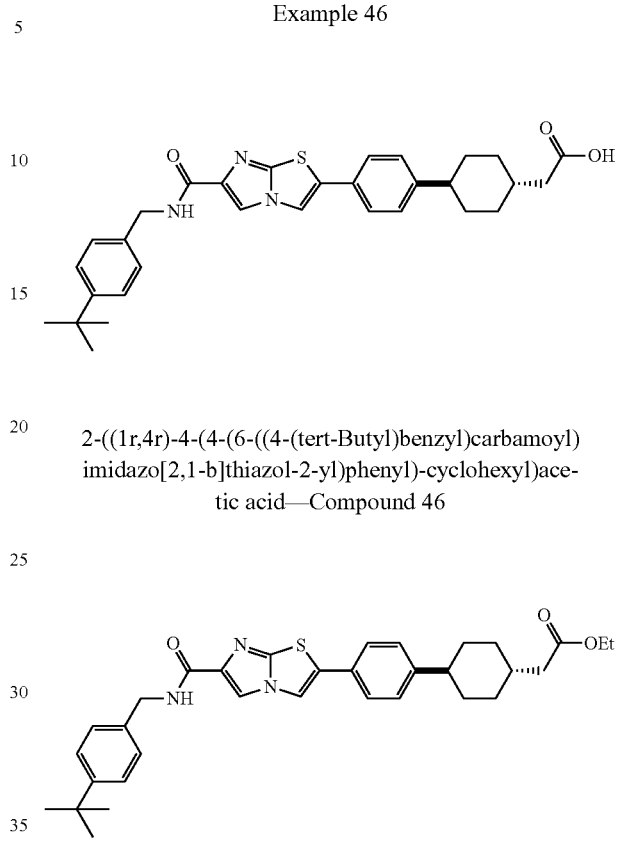

Step A: Ethyl 2-((1r,4r)-4-(4-(6-((4-(tert-butyl)benzyl)carbamoyl)imidazo[2,1-b]thiazol-2-yl)phenyl)cyclohexyl)acetate The title compound, was prepared from Intermediate XLVI and Intermediate LXV by using procedures analogous to those described for step A of Example 1.

$^1$H NMR (400 MHz, CDCl$_3$) 8.02 (s, 1H), 7.60 (s, 1H), 7.41 (d, 2H), 7.34 (d, 2H), 7.29 (s, 2H), 7.26 (d, 2H), 4.58 (d, 2H), 4.13 (d, 2H), 2.49 (t, 1H), 2.23 (d, 2H), 1.89 (d, 4H), 1.84 (m, 1H), 1.50 (q, 2H), 1.25 (t, 3H), 1.16 (q, 2H). MS 558.8 (M+1)$^+$.

Step B: 2-((1r,4r)-4-(4-(6-((4-(tert-Butyl)benzyl)carbamoyl)imidazo[2,1-b]thiazol-2-yl)phenyl)cyclohexyl)acetic acid Compound 46 was prepared by essentially following the same procedures described for the step B of Example 1.

$^1$H NMR (400 MHz, DMSO-d$_6$) δ 8.68 (t, 1H), 8.38 (s, 1H), 7.14 (s, 1H), 7.53 (d, 2H), 7.31 (d, 2H), 7.29 (d, 2H), 7.19 (d, 2H), 4.35 (d, 2H), 2.46 (m, 1H, overlap with DMSO peak), 2.06 (d, 2H), 1.83-1.75 (m, 5H), 1.44 (q, 2H), 1.21 (s, 9H), 1.07 (q, 2H). MS 530.8 (M+1)$^+$.

Example 47

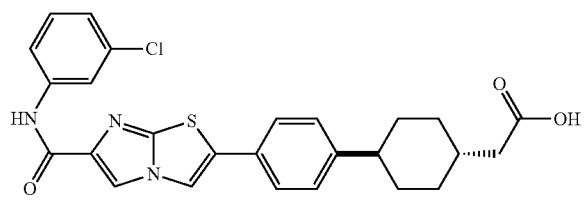 [SMILES: CCOC(=O)C[C@H]1CC[C@H](c2ccc(-c3cn4cc(C(=O)Nc5cccc(Cl)c5)nc4s3)cc2)CC1]

2-((1r,4r)-4-(4-(6-((3-Chlorophenyl)carbamoyl)imi-dazo[2,1-b]thiazol-2-yl)phenyl)cyclo-hexyl)acetic acid—Compound 47

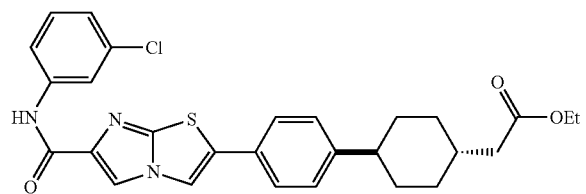

Step A: Ethyl 2-((1r,4r)-4-(4-(6-((3-chlorophenyl)carbamoyl)imidazo[2,1-b]thiazol-2-yl)-phenyl)cy-clohexyl)acetate The title compound was prepared from Intermediate XLVII and Intermediate LXV by essentially following the same procedures described for step A of Example 1.

$^1$H NMR (400 MHz, CDCl$_3$) δ 8.99 (s, 1H), 8.08 (s, 1H), 7.86 (t, 1H), 7.64 (s, 1H), 7.43 (d, 3H), 7.26 (dd, 4H), 4.13 (q, 2H), 2.51 (t, 1H), 2.23 (d, 2H), 1.92-1.89 (m, 5H), 1.71-1.68 (m, 1H), 1.52 (m, 2H, overlap with water peak), 1.25 (t, 3H), 1.16 (q, 2H). MS 523.5 (M+1)$^+$.

Step B: 2-((1r,4r)-4-(4-(6-((3-Chlorophenyl)carbamoyl)imidazo[2,1-b]thiazol-2-yl)phenyl)-cyclohexyl)acetic acid Compound 47 was prepared by essentially following the same procedures described for the step B of Example 1.

$^1$H NMR (400 MHz, DMSO-d$_6$) δ 10.33 (s, 1H), 8.43 (s, 1H), 8.34 (s, 1H), 8.04 (s, 1H), 7.78 (d, 1H), 7.55 (d, 2H), 7.30 (d, 2H), 7.09 (d, 1H), 6.83 (s, 1H), 6.60 (s, 1H), 2.53 (m, 1H, overlap with DMSO peak), 2.11 (d, 2H), 1.91-1.78 (m, 6H), 1.45 (q, 2H), 1.11 (q, 2H). MS 495.2 (M+1)$^+$.

Example 48

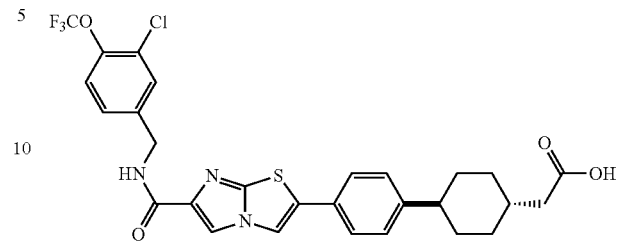

2-((1r,4r)-4-(4-(6-((3-Chloro-4-(trifluoromethoxy)benzyl)carbamoyl)imidazo[2,1-b]thiazol-2-yl)phenyl)cyclohexyl)acetic acid—Compound 48

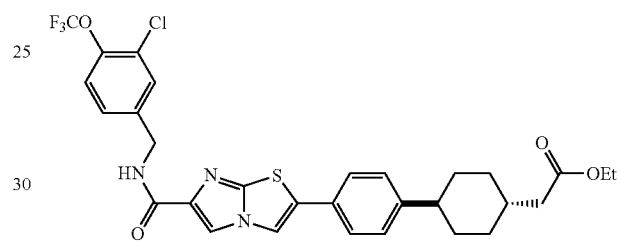

Step A: Ethyl 2-((1r,4r)-4-(4-(6-((3-chloro-4-(trifluoromethoxy)benzyl)carbamoyl)imidazo-[2,1-b]thiazol-2-yl)phenyl)cyclohexyl)acetate The title compound was prepared from Intermediate XLVIII and Intermediate LXV by essentially following the same procedures described for step A of Example 1.

$^1$H NMR (400 MHz, CDCl$_3$) δ 8.02 (s, 1H), 7.62 (s, 1H), 7.51 (t, 1H), 7.46 (s, 1H), 7.42 (d, 2H), 7.27-7.26 (m, 3H), 7.25 (s, 1H), 4.60 (d, 2H), 4.13 (q, 2H), 2.50 (t, 1H), 2.23 (d, 2H), 1.91-1.88 (m, 6H), 1.49 (q, 2H), 1.25 (t, 3H), 1.16 (q, 2H). MS 621.2 (M+1)$^+$.

Step B: 2-((1r,4r)-4-(4-(6-((3-Chloro-4-(trifluoromethoxy)benzyl)carbamoyl)imidazo[2,1-b]thiazol-2-yl)phenyl)cyclohexyl)acetic acid Compound 48 was prepared by essentially following the same procedures described for the step B of Example 1.

$^1$H NMR (400 MHz, DMSO-d$_6$) δ 8.91 (s, 1H), 8.37 (s, 1H), 8.17 (s, 1H), 7.58 (s, 1H), 7.53 (d, 2H), 7.49 (d, 1H), 7.36 (d, 1H), 7.32 (d, 2H), 4.41 (d, 2H), 2.53 (m, 1H, overlap with DMSO peak), 2.12 (d, 2H), 1.92-1.78 (m, 6H), 1.43 (q, 2H), 1.12 (q, 2H). MS 593.2 (M+1)$^+$.

Example 49

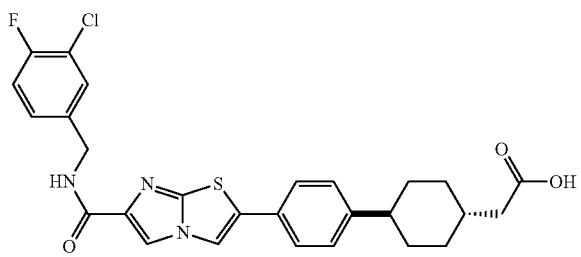 [SMILES: O=C(O)C[C@H]1CC[C@H](c2ccc(-c3cn4cc(C(=O)NCc5ccc(F)c(Cl)c5)nc4s3)cc2)CC1]

2-((1r,4r)-4-(4-(6-((3-Chloro-4-fluorobenzyl)carbamoyl)imidazo[2,1-b]thiazol-2-yl)phenyl)-cyclohexyl)acetic acid—Compound 49

Step A: Ethyl 2-((1r,4r)-4-(4-(6-((3-chloro-4-fluorobenzyl)carbamoyl)imidazo[2,1-b]-thiazol-2-yl)phenyl)cyclohexyl)acetate

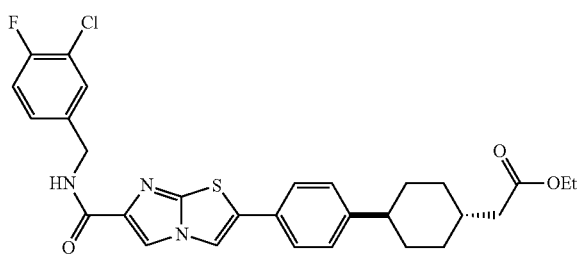 [SMILES: CCOC(=O)C[C@H]1CC[C@H](c2ccc(-c3cn4cc(C(=O)NCc5ccc(F)c(Cl)c5)nc4s3)cc2)CC1]

The title compound was prepared from Intermediate XLIX and Intermediate LXV by essentially following the same procedures described for step A of Example 1.

$^1$H NMR (400 MHz, CDCl$_3$) δ 8.02 (s, 1H), 7.61 (s, 1H), 7.48 (t, 1H), 7.42 (d, 2H), 7.38 (dd, 1H), 7.26 (d, 2H), 7.21-7.19 (m, 1H), 7.07 (t, 1H), 4.56 (d, 2H), 4.13 (q, 2H), 2.49 (t, 1H), 2.23 (d, 2H), 1.91-1.85 (m, 6H), 1.50 (q, 2H), 1.25 (t, 3H), 1.16 (q, 2H). MS 555.2 (M+1)$^+$.

Step B: 2-((1r,4r)-4-(4-(6-((3-Chloro-4-fluorobenzyl)carbamoyl)imidazo[2,1-b]thiazol-2-yl)phenyl)cyclohexyl)acetic acid Compound 49 was prepared by essentially following the same procedures described for the step B of Example 1.

$^1$H NMR (400 MHz, DMSO-d$_6$) δ 8.86 (s, 1H), 8.37 (s, 1H), 8.16 (s, 1H), 7.52 (d, 2H), 7.46 (qd, 2H), 4.39 (d, 2H), 2.53 (m, 1H, overlap with DMSO peak), 2.09 (d, 2H), 1.94-1.78 (m, 6H), 1.44 (q, 2H), 1.09 (q, 2H). MS 527.2 (M+1)$^+$.

Example 50

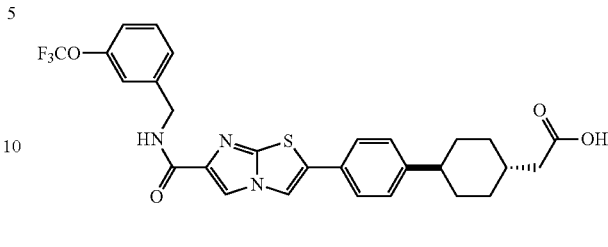

2-((1r,4r)-4-(4-(6-((3-(Trifluoromethoxy)benzyl)carbamoyl)imidazo[2,1-b]thiazol-2-yl)-phenyl)cyclohexyl)acetic acid—Compound 50

Step A: Ethyl 2-((1r,4r)-4-(4-(6-((3-(trifluoromethoxy)benzyl)carbamoyl)imidazo[2,1-b]-thiazol-2-yl)phenyl)cyclohexyl)acetate

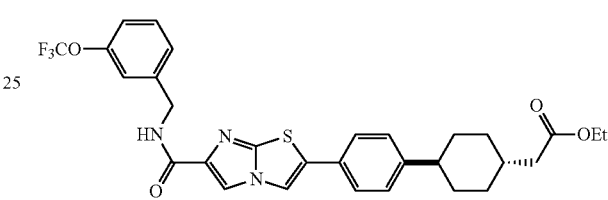

The title compound was prepared from Intermediate L and Intermediate LXV by essentially following the same procedures described for step A of Example 1.

$^1$H NMR (400 MHz, CDCl$_3$) δ 8.05 (s, 1H), 7.64 (s, 1H), 7.52 (t, 1H), 7.44 (dd, 2H), 7.35 (d, 1H), 7.29 (t, 3H), 7.21 (s, 1H), 7.12 (d, 1H), 4.65 (d, 2H), 4.12 (q, 2H), 2.52 (t, 1H), 2.25 (d, 2H), 1.93-1.88 (m, 6H), 1.52 (q, 2H), 1.26 (t, 3H), 1.18 (q, 2H). MS 586.6 (M+1)$^+$.

Step B: 2-((1r,4r)-4-(4-(6-((3-(Trifluoromethoxy)benzyl)carbamoyl)imidazo[2,1-b]thiazol-2-yl)-phenyl)cyclohexyl)acetic acid Compound 50 was prepared by essentially following the same procedures described for the step B of Example 1.

$^1$H NMR (400 MHz, DMSO-d$_6$) δ 8.90 (s, 1H), 8.37 (s, 1H), 8.19 (s, 1H), 7.54 (d, 2H), 7.43 (t, 1H), 7.33 (d, 3H), 7.26 (s, 1H), 7.20 (d, 1H), 4.45 (d, 2H), 2.53 (m, 1H, overlap with DMSO peak), 2.11 (d, 2H), 1.83-1.68 (m, 6H), 1.45 (q, 2H), 1.11 (q, 2H). MS 558.6 (M+1)$^+$.

Example 51

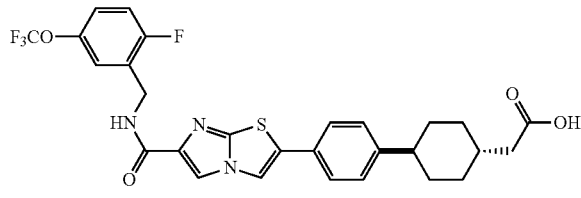 [SMILES: O=C(O)C[C@H]1CC[C@H](c2ccc(-c3cn4cc(C(=O)NCc5cc(OC(F)(F)F)ccc5F)nc4s3)cc2)CC1]

2-((1r,4r)-4-(4-(6-((2-Fluoro-5-(trifluoromethoxy)benzyl)carbamoyl)imidazo[2,1-b]thiazol-2-yl)phenyl)cyclohexyl)acetic acid—Compound 51

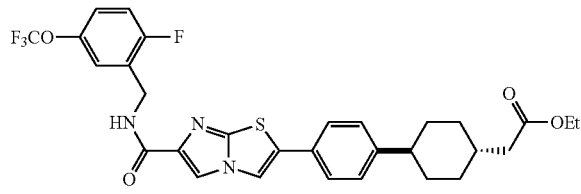 [SMILES: CCOC(=O)C[C@H]1CC[C@H](c2ccc(-c3cn4cc(C(=O)NCc5cc(OC(F)(F)F)ccc5F)nc4s3)cc2)CC1]

Step A: Ethyl 2-((1r,4r)-4-(4-(6-((2-fluoro-5-trifluoromethoxy)benzyl)carbamoyl)imidazo-[2,1-b]thiazol-2-yl)phenyl)cyclohexyl)acetate The title compound was prepared from Intermediate LI and Intermediate LXV by essentially following the same procedures described for step A of Example 1.

$^1$H NMR (400 MHz, CDCl$_3$) δ 8.04 (s, 1H), 7.63 (s, 1H), 7.53 (t, 1H), 7.43 (d, 2H), 7.27 (d, 2H), 7.08 (d, 2H), 4.68 (d, 2H), 4.15 (q, 2H), 2.51 (t, 1H), 2.25 (d, 2H), 1.93-1.90 (m, 6H), 1.52 (q, 2H), 1.27 (t, 3H), 1.17 (q, 2H). MS 604.2 (M+1)$^+$.

Step B: 2-((1r,4r)-4-(4-(6-((2-Fluoro-5-(trifluoromethoxy)benzyl)carbamoyl)imidazo[2,1-b]thiazol-2-yl)phenyl)cyclohexyl)acetic acid Compound 51 was prepared by essentially following the same procedures described for step B of Example 1.

$^1$H NMR (400 MHz, DMSO-d$_6$) δ 8.02 (s, 1H), 7.61 (s, 1H), 7.52 (d, 1H), 7.42 (d, 2H), 7.26 (d, 2H), 7.06 (q, 2H), 4.65 (d, 2H), 2.49 (t, 1H), 2.23 (d, 2H), 1.91-1.85 (m, 6H), 1.50 (q, 2H), 1.16 (q, 2H). MS 576.2 (M+1)$^+$.

Example 52

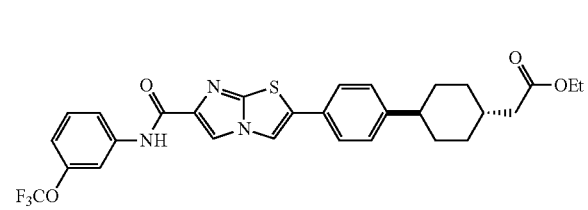

2-((1r,4r)-4-(4-(6-((3-(Trifluoromethoxy)phenyl)carbamoyl)imidazo[2,1-b]thiazol-2-yl)-phenyl)cyclohexyl)acetic acid—Compound 52

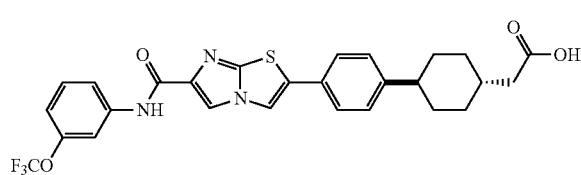 [SMILES: O=C(O)C[C@H]1CC[C@H](c2ccc(-c3cn4cc(C(=O)Nc5cccc(OC(F)(F)F)c5)nc4s3)cc2)CC1]

Step A: Ethyl 2-((1r,4r)-4-(4-(6-((3-(trifluoromethoxy)phenyl)carbamoyl)imidazo[2,1-b]-thiazol-2-yl)phenyl)cyclohexyl)acetate The title compound was prepared from Intermediate LII and Intermediate LXV by essentially following the same procedures described for step A of Example 1.

$^1$H NMR (400 MHz, CDCl$_3$) δ 9.06 (s, 1H), 8.11 (s, 1H), 7.79 (s, 1H), 7.64 (s, 1H), 7.53 (t, 1H), 7.43 (d, 2H), 7.34 (d, 1H), 7.27 (d, 2H), 6.95 (d, 1H), 4.13 (q, 2H), 2.49 (t, 1H), 2.23 (d, 2H), 1.92-1.82 (m, 6H), 1.50 (q, 2H), 1.25 (t, 3H), 1.16 (q, 2H). MS 572.2 (M1-1)$^+$.

Step B: 2-((1r,4r)-4-(4-(6-((3-(Trifluoromethoxy)phenyl)carbamoyl)imidazo[2,1-b]thiazol-2-yl)phenyl)cyclohexyl)acetic acid Compound 52 was prepared by essentially following the same procedures described for the step B of Example 1.

$^1$H NMR (400 MHz, DMSO-d$_6$) δ 10.47 (s, 1H), 8.43 (d, 1H), 8.34 (d, 1H), 8.03 (s, 1H), 7.89-7.84 (m, 1H), 7.54 (m, 2H), 7.42 (m, 1H), 7.32 (m, 2H), 7.02-7.01 (m, 1H), 2.53 (m, 1H, overlap with DMSO peak), 2.01 (d, 2H), 1.82-1.68 (m, 6H), 1.46-1.42 (m, 2H), 1.08-1.07 (m, 2H). MS 544.3 (M+1)$^+$.

Example 53

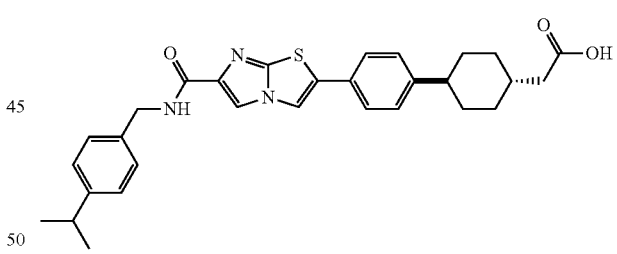

2-((1r,4r)-4-(4-(6-((4-Isopropylbenzyl)carbamoyl)imidazo[2,1-b]thiazol-2-yl)phenyl)cyclohexyl)acetic acid—Compound 53

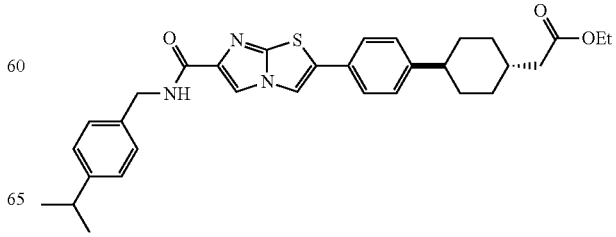

Step A: Ethyl 2-((1r,4r)-4-(4-(6-((4-isopropylbenzyl)carbamoyl)imidazo[2,1-b]thiazol-2-yl)-phenyl)cyclohexyl)acetate The title compound was prepared from Intermediate LIII and Intermediate LXV by essentially following the same procedures described for step A of Example 1.
$^1$H NMR (400 MHz, CDCl$_3$) δ 8.02 (s, 1H), 7.60 (s, 1H), 7.41 (d, 3H), 7.27 (d, 3H), 7.18 (d, 2H), 4.58 (d, 2H), 4.13 (q, 2H), 2.87 (m, 1H), 2.49 (t, 1H), 2.23 (d, 2H), 1.91-1.85 (m, 6H), 1.50 (q, 2H), 1.25 (t, 3H), 1.22 (d, 6H), 1.16 (q, 2H). MS 544.2 (M+1)$^+$.

Step B: 2-((1r,4r)-4-(4-(6-((4-Isopropylbenzyl)carbamoyl)imidazo[2,1-b]thiazol-2-yl)-phenyl)cyclohexyl)acetic acid Compound 53 was prepared by essentially following the same procedures described for the step B of Example 1.
$^1$H NMR (400 MHz, DMSO-d$_6$) δ 8.68 (t, 1H), 8.38 (s, 1H), 8.15 (s, 1H), 7.52 (d, 2H), 7.31 (d, 2H), 7.19 (d, 2H), 7.13 (d, 2H), 4.35 (d, 2H), 2.86-2.77 (m, 1H), 2.46 (m, 1H, overlap with DMSO peak), 2.10 (d, 2H), 1.80-1.75 (m, 6H), 1.44 (q, 2H), 1.13 (d, 2H), 1.08 (q, 2H). MS 516.3 (M+1)$^+$.

Example 54

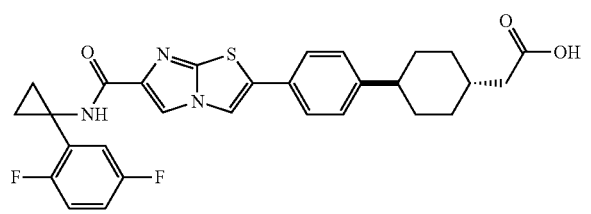

2-((1r,4r)-4-(4-(6-((1-(2,5-Difluorophenyl)cyclopropyl)carbamoyl)imidazo[2,1-b]thiazol-2-yl)phenyl)cyclohexyl)acetic acid—Compound 54

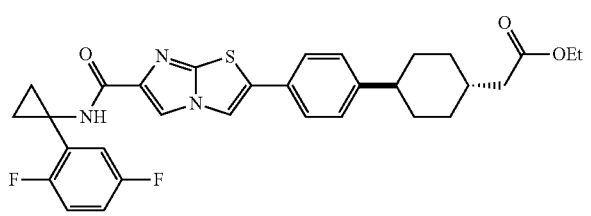

Step A: Ethyl 2-((1r,4r)-4-(4-(6-((1-(2,5-difluorophenyl)cyclopropyl)carbamoyl)imidazo-[2,1-b]thiazol-2-yl)phenyl)cyclohexyl)acetate The title compound was prepared from Intermediate LIV and Intermediate LXV by essentially following the same procedures described for step A of Example 1.
$^1$H NMR (400 MHz, CDCl$_3$) δ 7.92 (s, 1H), 7.83 (s, 1H), 7.57 (s, 1H), 7.40 (d, 2H), 7.36 (m, 1H), 7.26 (s, 1H), 6.95-6.88 (m, 2H), 4.13 (q, 2H), 2.49 (t, 1H), 2.23 (d, 2H), 1.94-1.88 (m, 6H), 1.45 (q, 2H), 1.25 (m, 7H), 1.15 (q, 2H). MS 564.3 (M+1)$^+$.

Step B: 2-((1r,4r)-4-(4-(6-((1-(2,5-Difluorophenyl)cyclopropyl)carbamoyl)imidazo[2,1-b]-thiazol-2-yl)phenyl)cyclohexyl)acetic acid Compound 54 was prepared by essentially following the same procedures described for the step B of Example 1.
$^1$H NMR (400 MHz, DMSO-d$_6$) δ 8.73 (s, 1H), 8.36 (s, 1H), 8.10 (s, 1H), 7.52 (d, 2H), 7.31 (d, 3H), 7.15-7.07 (m, 2H), 2.47 (m, 1H, overlap with DMSO peak), 2.09 (d, 2H), 1.77-1.75 (m, 5H), 1.44 (q, 2H), 1.20 (m, 4H), 1.07 (q, 2H). MS 536.2 (M+1)$^+$.

Example 55

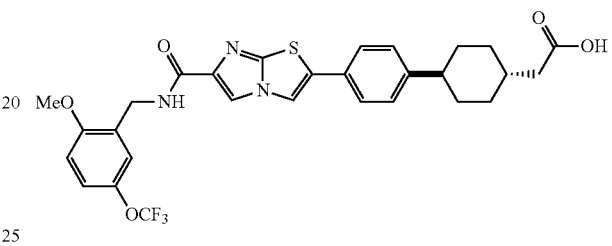

2-((1r,4r)-4-(4-(6-((2-Methoxy-5-(trifluoromethoxy)benzyl)carbamoyl)imidazo[2,1-b]-thiazol-2-yl)phenyl)cyclohexyl)acetic acid—Compound 55

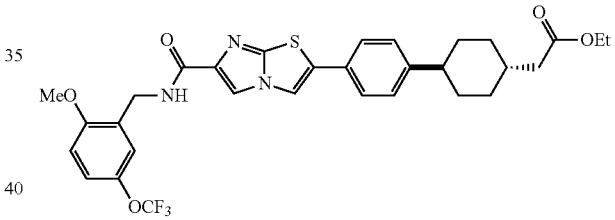

Step A: Ethyl 2-((1r,4r)-4-(4-(6-((2-methoxy-5-(trifluoromethoxy)benzyl)carbamoyl)-imidazo[2,1-b]thiazol-2-yl)phenyl)cyclohexyl)acetate The title compound was prepared from Intermediate LV and Intermediate LXV by essentially following the same procedures described for step A of Example 1.
$^1$H NMR (400 MHz, CDCl$_3$) δ 8.01 (s, 1H), 7.60 (s, 1H), 7.54 (t, 1H), 7.41 (d, 2H), 7.19 (d, 2H), 7.09 (d, 2H), 6.83 (d, 1H), 6.83 (s, 1H), 4.60 (d, 2H), 4.13 (q, 2H), 3.87 (s, 3H), 2.49 (t, 1H), 2.23 (d, 2H), 1.95-1.80 (m, 6H), 1.50 (q, 2H), 1.25 (t, 3H), 1.16 (q, 2H). MS 616.3 (M+1)$^+$.

Step B: 2-((1r,4r)-4-(4-(6-((2-Methoxy-5-(trifluoromethoxy)benzyl)carbamoyl)imidazo[2,1-b]thiazol-2-yl)phenyl)cyclohexyl)acetic acid Compound 55 was prepared by essentially following the same procedures described for the step B of Example 1.
$^1$H NMR (400 MHz, DMSO-d$_6$) δ 8.65 (t, 1H), 8.39 (s, 1H), 8.19 (s, 1H), 7.54 (d, 2H), 7.32 (d, 2H), 7.20 (d, 1H), 7.05 (d, 3H), 4.37 (d, 2H), 3.83 (s, 3H), 2.46 (m, 1H, overlap with DMSO peak), 2.10 (d, 2H), 1.86-1.78 (m, 6H), 1.44 (q, 2H), 1.08 (q, 2H). MS 588.2 (M+1)$^+$.

Example 56

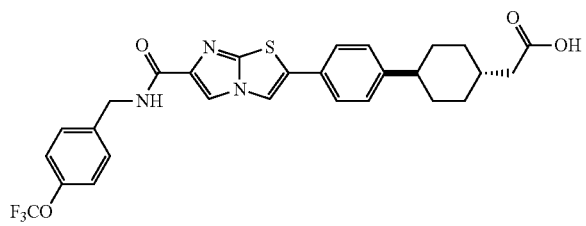

2-((1r,4r)-4-(4-(6-((4-(Trifluoromethoxy)benzyl)carbamoyl)imidazo[2,1-b]thiazol-2-yl)-phenyl)cyclohexyl)acetic acid—Compound 56

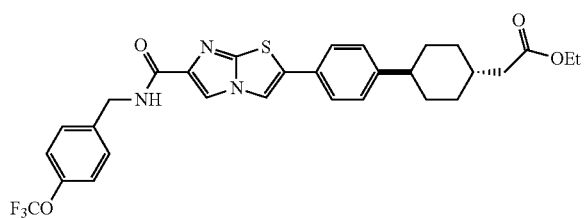

Step A: Ethyl 2-((1r,4r)-4-(4-(6-((4-(trifluoromethoxy)benzyl)carbamoyl)imidazo[2,1-b]-thiazol-2-yl)phenyl)cyclohexyl)acetate The title compound was prepared from Intermediate LVI and Intermediate LXV by essentially following the same procedures described for step A of Example 1.

$^1$H NMR (400 MHz, CDCl$_3$) δ 8.03 (s, 1H), 7.61 (s, 1H), 7.48 (t, 1H), 7.40 (d, 2H), 7.32 (d, 2H), 7.26 (d, 2H), 7.16 (d, 2H), 4.62 (d, 2H), 4.13 (d, 2H), 2.49 (t, 1H), 2.23 (d, 2H), 1.94-1.85 (m, 6H), 1.50 (q, 2H), 1.25 (t, 3H), 1.16 (q, 2H). MS 586.3 (M+1)$^+$.

Step B: 2-((1r,4r)-4-(4-(6-((4-(Trifluoromethoxy)benzyl)carbamoyl)imidazo[2,1-b]thiazol-2-yl)phenyl)cyclohexyl)acetic acid Compound 56 was prepared by essentially following the same procedures described for the step B of Example 1.

$^1$H NMR (400 MHz, DMSO-d$_6$) δ 12.0 (br s, 1H), 8.86 (t, 1H), 8.38 (s, 1H), 8.16 (s, 1H), 7.53 (d, 2H), 7.39 (d, 2H), 7.32 (d, 2H), 7.28 (d, 2H), 4.41 (d, 2H), 2.46 (m, 1H, overlap with DMSO peak), 2.11 (d, 2H), 1.84-1.75 (m, 6H), 1.44 (q, 2H), 1.08 (q, 2H). MS 558.2 (M+1)$^+$.

Example 57

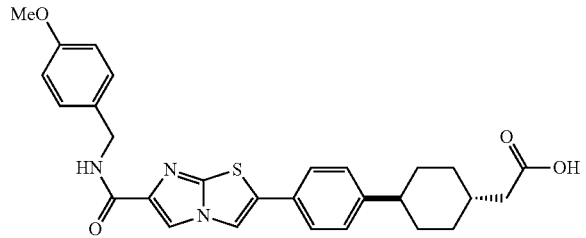

2-((1r,4r)-4-(4-(6-((4-Methoxybenzyl)carbamoyl)imidazo[2,1-b]thiazol-2-yl)phenyl)cyclo-hexyl)acetic acid—Compound 57

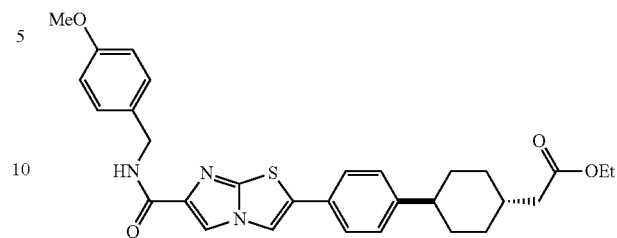

Step A: Ethyl 2-((1r,4r)-4-(4-(6-((4-methoxybenzyl)carbamoyl)imidazo[2,1-b]thiazol-2-yl)-phenyl)cyclohexyl)acetate The title compound was prepared from Intermediate LVII and Intermediate LXV by essentially following the same procedures described for step A of Example 1.

$^1$H NMR (400 MHz, CDCl$_3$) δ 8.01 (s, 1H), 7.60 (s, 1H), 7.41 (d, 1H), 7.38 (t, 1H), 7.27 (d, 3H), 6.85 (d, 2H), 4.55 (d, 2H), 4.18 (q, 2H), 3.78 (s, 3H), 2.49 (t, 1H), 2.23 (d, 2H), 1.92-1.84 (m, 6H), 1.50 (q, 2H), 1.25 (t, 3H), 1.16 (q, 2H). MS 532.2 (M+1)$^+$.

Step B: 2-((1r,4r)-4-(4-(6-((4-Methoxybenzyl)carbamoyl)imidazo[2,1-b]thiazol-2-yl)-phenyl)cyclohexyl)acetic acid Compound 57 was prepared by essentially following the same procedures described for the step B of Example 1.

$^1$H NMR (400 MHz, DMSO-d$_6$) δ 8.61 (s, 1H), 8.39 (s, 1H), 8.16 (s, 1H), 7.55 (d, 2H), 7.34 (d, 2H), 7.23 (d, 2H), 6.86 (d, 2H), 4.35 (d, 2H), 3.71 (s, 3H), 2.53 (m, 1H, overlap with DMSO peak), 2.13 (d, 2H), 1.87-1.80 (m, 6H), 1.46 (q, 2H), 1.16 (q, 2H). MS 504.0 (M+1)$^+$.

Example 58

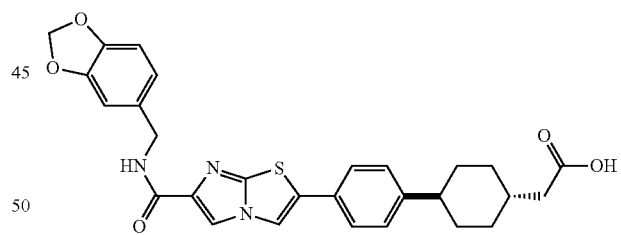

2-((1r,4r)-4-(4-(6-((Benzo[d][1,3]dioxol-5-ylmethyl)carbamoyl)imidazo[2,1-b]thiazol-2-yl)-phenyl)cyclohexyl)acetic acid—Compound 58

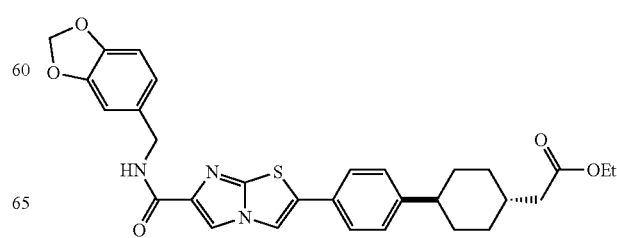

Step A: Ethyl 2-((1r,4r)-4-(4-(6-((benzo[d][1,3]di-oxol-5-ylmethyl)carbamoyl)imidazo[2,1-b]thiazol-2-yl)phenyl)cyclohexyl)acetate The title compound was prepared from Intermediate LVIII and Intermediate LXV by essentially following the same procedures described for step A of Example 1.

$^1$H NMR (400 MHz, CDCl$_3$) δ 8.01 (s, 1H), 7.61 (s, 1H), 7.41 (d, 3H), 6.95 (d, 1H), 6.82 (d, 2H), 6.74 (d, 2H), 5.92 (s, 2H), 4.52 (d, 2H), 4.13 (q, 2H), 2.49 (m, 1H), 2.23 (d, 2H), 1.95-1.88 (m, 6H), 1.54 (q, 2H), 1.25 (t, 3H), 1.16 (q, 2H). MS 546.2 (M+1)$^+$.

Step B: 2-((1r,4r)-4-(4-(6-((Benzo[d][1,3]dioxol-5-ylmethyl)carbamoyl)imidazo[2,1-b]-thiazol-2-yl)phenyl)cyclohexyl)acetic acid Compound 58 was prepared by essentially following the same procedures described for the step B of Example 1.

$^1$H NMR (400 MHz, DMSO-d$_6$) δ 8.70 (t, 1H), 8.39 (s, 1H), 8.16 (s, 1H), 7.54 (d, 2H), 7.33 (d, 2H), 6.87 (s, 1H), 6.82 (d, 1H), 6.76 (d, 1H), 5.94 (s, 2H), 4.30 (d, 2H), 2.48 (m, 1H, overlap with DMSO peak), 2.01 (d, 2H), 1.81-1.75 (m, 6H), 1.44 (q, 2H), 1.04 (q, 2H). MS 518.0 (M+1)$^+$.

Example 59

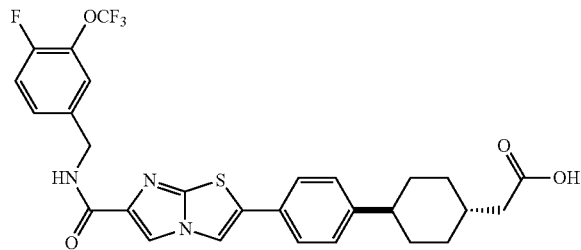

2-((1r,4r)-4-(4-(6-((4-Fluoro-3-(trifluoromethoxy)benzyl)carbamoyl)imidazo[2,1-b]thiazol-2-yl)phenyl)cyclohexyl)acetic acid—Compound 59

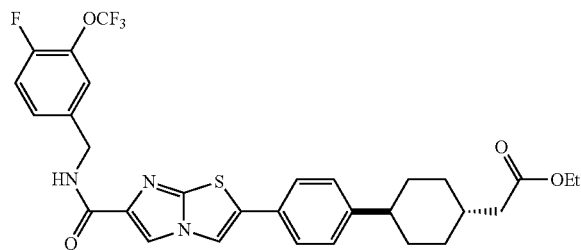

Step A: Ethyl 2-((1r,4r)-4-(4-(6-((4-fluoro-3-(trifluoromethoxy)benzyl)carbamoyl)imidazo-[2,1-b]thiazol-2-yl)phenyl)cyclohexyl)acetate The title compound was prepared from Intermediate LIX and Intermediate LXV by essentially following the same procedures described for step A of Example 1.

$^1$H NMR (400 MHz, CDCl$_3$) δ 8.02 (s, 1H), 7.61 (s, 1H), 7.51 (d, 1H), 7.42 (d, 2H), 7.27 (t, 4H), 7.14 (t, 1H), 4.95 (d, 2H), 4.13 (q, 2H), 2.50 (t, 1H), 2.23 (d, 2H), 1.92-1.87 (m, 6H), 1.50 (q, 2H), 1.25 (t, 3H), 1.16 (q, 2H). MS 604.1 (M+1)$^+$.

Step B: 2-((1r,4r)-4-(4-(6-((4-Fluoro-3-(trifluoromethoxy)benzyl)carbamoyl)imidazo[2,1-b]-thiazol-2-yl)phenyl)cyclohexyl)acetic acid Compound 59 was prepared by essentially following the same procedures described for the step B of Example 1.

$^1$H NMR (400 MHz, DMSO-d$_6$) δ 8.95-8.89 (br s, 1H), 8.39 (s, 1H), 8.15 (s, 1H), 7.53 (d, 2H), 7.46 (d, 1H), 7.41 (d, 1H), 7.37 (dd, 1H), 7.32 (d, 2H), 4.41 (d, 2H), 2.53 (m, 1H, overlap with DMSO peak), 2.11 (d, 2H), 1.81-1.71 (m, 6H), 1.45 (qd, 2H), 1.10 (q, 2H). MS 576.1 (M+1)$^+$.

Example 60

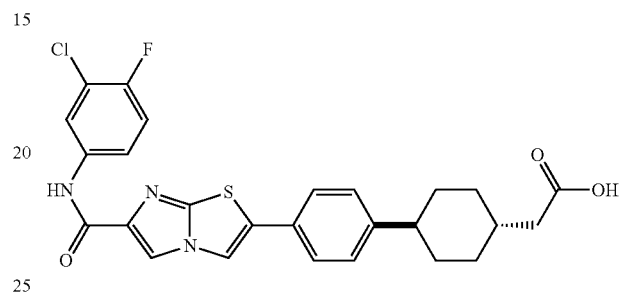

2-((1r,4r)-4-(4-(6-((3-Chloro-4-fluorophenyl)carbamoyl)imidazo[2,1-b]thiazol-2-yl)-phenyl)cyclohexyl)acetic acid—Compound 60

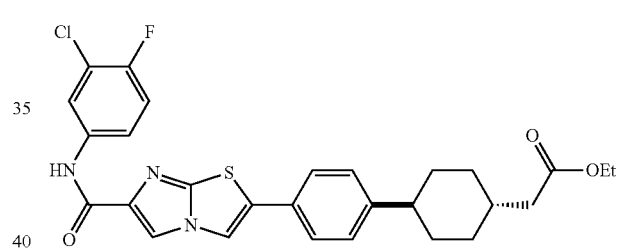

Step A: Ethyl 2-((1r,4r)-4-(4-(6-((3-chloro-4-fluorophenyl)carbamoyl)imidazo[2,1-b]-thiazol-2-yl)phenyl)cyclohexyl)acetate The title compound was prepared from Intermediate LX and Intermediate LXV by essentially following the same procedures described for step A of Example 1.

$^1$H NMR (400 MHz, CDCl$_3$) δ 8.97 (s, 1H), 8.08 (s, 1H), 7.92 (dd, 1H), 7.63 (s, 1H), 7.49 (d, 1H), 7.43 (d, 2H), 7.27 (t, 2H), 7.10 (t, 1H), 4.13 (q, 2H), 2.51 (t, 1H), 2.23 (d, 2H), 1.92-1.86 (m, 6H), 1.51 (q, 2H), 1.26 (t, 3H), 1.17 (q, 2H). MS 541.2 (M+1)$^+$.

Step B: 2-((1r,4r)-4-(4-(6-((3-Chloro-4-fluorophenyl)carbamoyl)imidazo[2,1-b]thiazol-2-yl)phenyl)cyclohexyl)acetic acid Compound 60 was prepared by essentially following the same procedures described for the step B of Example 1.

$^1$H NMR (400 MHz, DMSO-d$_6$) δ 10.45 (s, 1H), 8.44 (s, 1H), 8.36 (s, 1H), 8.17 (dd, 1H), 7.84-7.81 (m, 1H), 7.56 (d, 2H), 7.35 (t, 3H), 2.48 (m, 1H, overlap with DMSO peak), 2.08 (d, 2H), 1.88-1.71 (m, 6H), 1.46 (q, 2H), 1.09 (q, 2H). MS 513.2 (M+1)$^+$.

Example 61

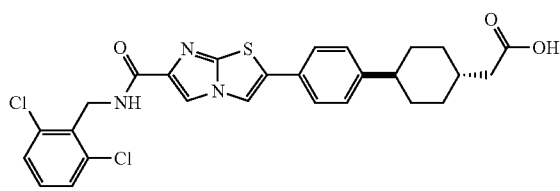 [SMILES: O=C(O)C[C@H]1CC[C@H](c2ccc(-c3cn4cc(C(=O)NCc5c(Cl)cccc5Cl)nc4s3)cc2)CC1]

2-((1r,4r)-4-(4-(6-((2,6-dichlorobenzyl)carbamoyl)imidazo[2,1-b]thiazol-2-yl)phenyl)cyclohexyl)acetic acid—Compound 61

Step A: Ethyl 2-((1r,4r)-4-(4-(6-((2,6-dichlorobenzyl)carbamoyl)imidazo[2,1-b]thiazol-2-yl)_phenyl)cyclohexyl)acetate

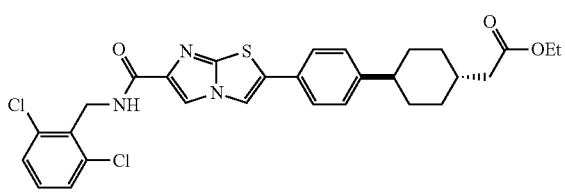 [SMILES: CCOC(=O)C[C@H]1CC[C@H](c2ccc(-c3cn4cc(C(=O)NCc5c(Cl)cccc5Cl)nc4s3)cc2)CC1]

The title compound was prepared from Intermediate LXI and Intermediate LXV by essentially following the same procedures described for step A of Example 1.

$^1$H NMR (400 MHz, CDCl$_3$) δ 8.01 (s, 1H), 7.60 (s, 1H), 7.39 (d, 2H), 7.34 (m, 1H), 7.30 (d, 2H), 7.23 (d, 2H), 7.16 (d, 1H), 4.92 (d, 2H), 4.12 (q, 2H), 3.5-2.4 (m, 1H), 2.22 (d, 2H), 1.89-1.87 (m, 5H), 1.51-1.49 (m, 2H), 1.24 (t, 3H), 1.2-1.15 (m, 2H). MS 572.9 (M+1)$^+$.

Step B: 2-((1r,4r)-4-(4-(6-((2,6-dichlorobenzyl)carbamoyl)imidazo[2,1-b]thiazol-2-yl)phenyl)cyclohexyl)acetic acid Compound 61 was prepared by essentially following the same procedures described for the step B of Example 1.

$^1$H NMR (400 MHz, DMSO-d$_6$) δ 8.38 (s, 1H), 8.18 (s, 1H), 7.52 (d, 2H), 7.48-7.45 (m, 3H), 7.36-7.34 (m, 2H), 4.52 (d, 2H), 2.50 (m, 1H, overlap with DMSO peak), 2.30-2.26 (m, 2H), 1.73-1.65 (m, 5H), 1.45-1.39 (m, 2H), 1.10-0.98 (m, 2H). MS 544.6 (M+1)$^+$.

Example 62

2-((1r,4r)-4-(4-(6-((2-chloro-6-fluorobenzyl)carbamoyl)imidazo[2,1-b]thiazol-2-yl)phenyl)cyclohexyl)acetic acid—Compound 62

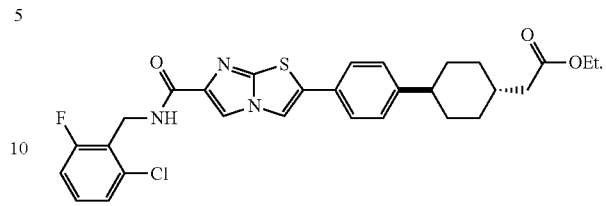

Step A: Ethyl 2-((1r,4r)-4-(4-(6-((2-chloro-6-fluorobenzyl)carbamoyl)imidazo[2,1-b]thiazol-2-yl)phenyl)cyclohexyl)acetate The title compound was prepared from Intermediate LXII and Intermediate LXV by essentially following the same procedures described for step A of Example 1.

$^1$H NMR (400 MHz, CDCl$_3$) δ 7.99 (s, 1H), 7.59 (s, 1H), 7.39 (d, 3H), 7.23 (d, 2H), 7.18 (d, 2H), 6.98 (td, 1H), 4.79 (d, 2H), 4.12 (q, 2H), 2.48 (t, 1H), 2.22 (d, 2H), 1.89-1.81 (m, 5H), 1.48 (q, 2H), 1.24 (t, 3H), 1.13-1.11 (m, 2H). MS 555.7 (M+1)$^+$.

Step B: 2-((1r,4r)-4-(4-(6-((2-chloro-6-fluorobenzyl)carbamoyl)imidazo[2,1-b]thiazol-2-yl)phenyl)cyclohexyl)acetic acid Compound 62 was prepared by essentially following the same procedures described for the step B of Example 1.

$^1$H NMR (400 MHz, DMSO-d$_6$) δ 8.38 (s, 1H), 8.30 (d, 1H), 8.16 (s, 1H), 7.53 (d, 2H), 7.36-7.31 (m, 3H), 7.20 (t, 1H), 4.57 (d, 2H), 2.50 (m, 1H, overlap with DMSO peak), 2.11 (d, 2H), 1.79-1.73 (m, 5H), 1.50-1.41 (m, 2H), 1.11-1.08 (m, 2H). MS 527.7 (M+1)$^+$.

Example 63

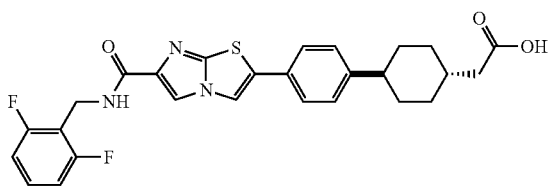

2-((1r,4r)-4-(4-(6-((2,6-difluorobenzyl)carbamoyl)imidazo[2,1-b]thiazol-2-yl)phenyl)cyclohexyl)acetic acid—Compound 63

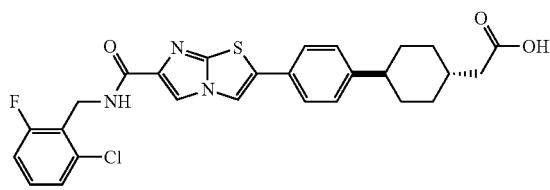 [SMILES: O=C(O)C[C@H]1CC[C@H](c2ccc(-c3cn4cc(C(=O)NCc5c(F)cccc5Cl)nc4s3)cc2)CC1]

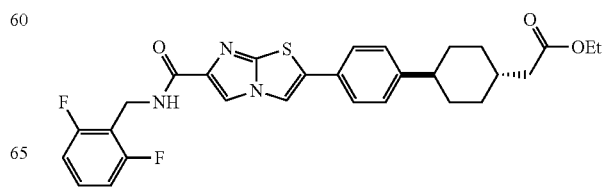

Step A: Ethyl 2-((1r,4r)-4-(4-(6-((2,6-difluorobenzyl)carbamoyl)imidazo[2,1-b]thiazol-2-yl)phenyl)cyclohexyl)acetate The title compound was prepared from Intermediate LXIII and Intermediate LXV by essentially following the same procedures described for step A of Example 1.

$^1$H NMR (400 MHz, CDCl$_3$) δ 8.01 (s, 1H), 7.59 (s, 1H), 7.43 (t, 1H), 7.39 (d, 2H), 7.24-7.22 (m, 2H), 6.88-6.84 (m, 2H), 4.69 (d, 2H), 4.11 (q, 2H), 2.47 (t, 1H), 2.21 (d, 2H), 1.89-1.79 (m, 5H), 1.48 (q, 2H), 1.23 (t, 3H), 1.15-1.12 (m, 2H). MS 538.8 (M+1)$^+$.

Step B: 2-((1r,4r)-4-(4-(6-((2,6-difluorobenzyl)carbamoyl)imidazo[2,1-b]thiazol-2-yl)phenyl)cyclohexyl)acetic acid Compound 63 was prepared by essentially following the same procedures described for the step B of Example 1.

$^1$H NMR (400 MHz, DMSO-d$_6$) δ 8.47-8.43 (m, 1H), 8.38 (s, 1H), 8.16 (s, 1H), 7.53 (d, 2H), 7.32 (d, 2H), 7.07-7.02 (m, 2H), 4.48 (d, 2H), 2.50 (m, 1H, overlap with DMSO peak), 2.12 (d, 2H), 1.88-1.79 (m, 5H), 1.45 (q, 2H), 1.06 (q, 2H). MS 510.9 (M+1)$^+$.

Example 64

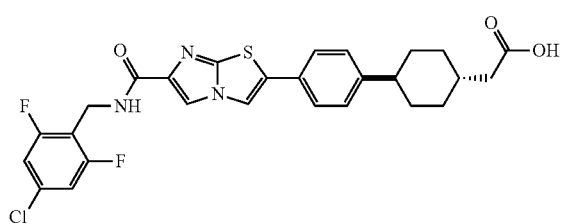 [SMILES: O=C(O)C[C@H]1CC[C@H](c2ccc(-c3cn4cc(C(=O)NCc5c(F)cc(Cl)cc5F)nc4s3)cc2)CC1]

2-((1r,4r)-4-(4-(6-((4-chloro-2,6-difluorobenzyl)carbamoyl)imidazo[2,1-b]thiazol-2-yl)phenyl)cyclohexyl)acetic acid—Compound 64

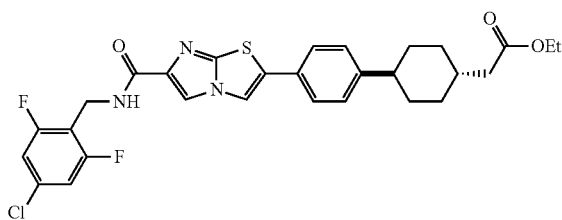 [SMILES: CCOC(=O)C[C@H]1CC[C@H](c2ccc(-c3cn4cc(C(=O)NCc5c(F)cc(Cl)cc5F)nc4s3)cc2)CC1]

Step A: Ethyl 2-((1r,4r)-4-(4-(6-((4-chloro-2,6-difluorobenzyl)carbamoyl)imidazo[2,1-b]thiazol-2-yl)phenyl)cyclohexyl)acetate The title compound was prepared from Intermediate LXIV and Intermediate LXV by essentially following the same procedures described for step A of Example 1.

$^1$H NMR (400 MHz, CDCl$_3$) δ 7.99 (s, 1H), 7.59 (s, 1H), 7.40 (d, 2H), 7.24 (d, 2H), 6.92 (d, 2H), 4.66 (d, 2H), 4.11 (q, 2H), 2.48 (t, 1H), 2.21 (d, 2H), 1.90-1.81 (m, 5H), 1.49 (q, 2H), 1.35 (m, 3H), 1.30 (m, 2H). MS 573.6 (M+1)$^+$.

Step B: 2-((1r,4r)-4-(4-(6-((4-chloro-2,6-difluorobenzyl)carbamoyl)imidazo[2,1-b]thiazol-2-yl)phenyl)cyclohexyl)acetic acid Compound 64 was prepared by essentially following the same procedures described for the step B of Example 1.

$^1$H NMR (400 MHz, DMSO-d$_6$) δ 12.10 (br s, 1H), 8.57 (s, 1H), 8.39 (s, 1H), 8.19 (s, 1H), 7.53 (d, 2H), 7.31 (m, 4H), 4.44 (d, 2H), 2.50 (m, 1H, overlap with DMSO peak), 2.12 (d, 2H), 1.86-1.82 (m, 5H), 1.47 (m, 2H), 1.08 (m, 2H). MS 545.6 (M+1)$^+$.

Example 65

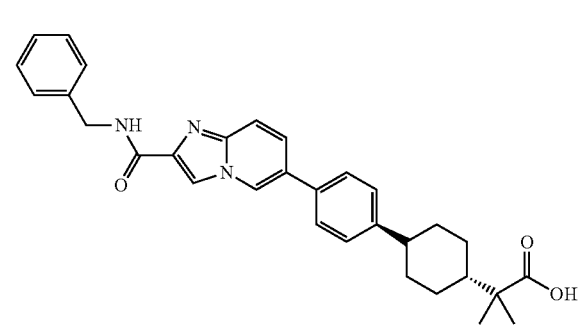

2-((1r,4r)-4-(4-(2-(Benzylcarbamoyl)imidazo[1,2-a]pyridin-6-yl)phenyl)cyclohexyl)-2-methylpropanoic acid—Compound 65

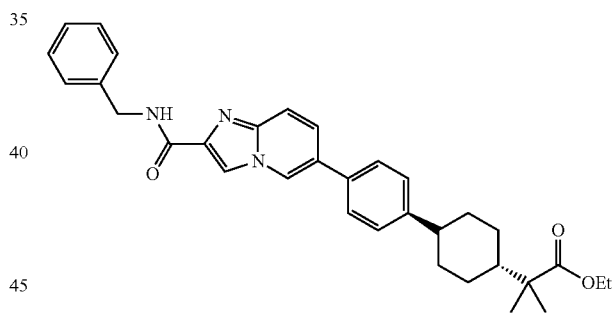

Step A: Ethyl 2-((1r,4r)-4-(4-(2-(benzylcarbamoyl)imidazo[1,2-a]pyridin-6-yl)phenyl)cyclohexyl)-2-methylpropanoate The title compound was prepared from Intermediate XXXI and Intermediate LXVI by using procedures analogous to those described for step A of Example 1.

$^1$H NMR (400 MHz CDCl$_3$) δ 8.29-8.28 (m, 1H), 8.20 (s, 1H), 7.69 (t, 1H), 7.58 (d, 1H), 7.51-7.47 (m, 3H), 7.40-7.28 (m, 7H), 4.68 (d, 2H), 4.15 (q, 2H), 2.55-2.49 (m, 1H), 1.97 (d, 2H), 1.78-1.69 (m, 3H), 1.52 (dq, 2H), 1.30-1.22 (m, 5H), 1.16 (s, 6H). MS 524.4 (M+1)$^+$.

Step B: 2-((1r,4r)-4-(4-(2-Benzylcarbamoyl)imidazo[2-a]pyridin-6-yl)phenyl)cyclohexyl)-2-methylpropanoic acid Compound 65 was prepared by essentially following the same procedures described for the step B of Example 1.

¹H NMR (400 MHz DMSO-d₆) δ 12.02 (br s, 1H), 8.92-8.88 (m, 2H), 8.32 (s, 1H), 7.67-7.58 (m, 4H), 7.35-7.26 (m, 6H), 7.22-7.18 (m, 1H), 4.44 (d, 2H), 2.50 (1H, overlapped with DMSO peaks), 1.86 (d, 2H), 1.70-1.59 (m, 3H), 1.45 (q, 2H), 1.18 (q, 2H), 1.03 (s, 6H). MS 496.3 (M+1)⁺.

Example 66

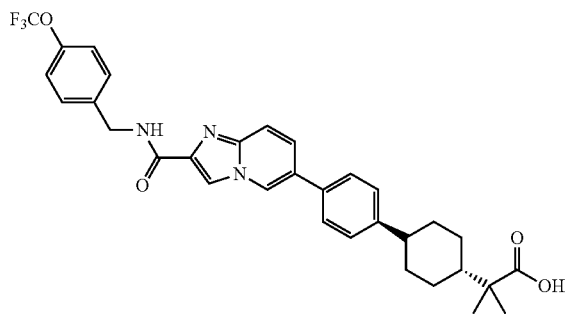

2-Methyl-2-((1r,4r)-4-(4-(2-((4-(trifluoromethoxy)benzyl)carbamoyl)imidazo[1,2-a]pyridin-6-yl)phenyl)cyclohexyl)propanoic acid—Compound 66

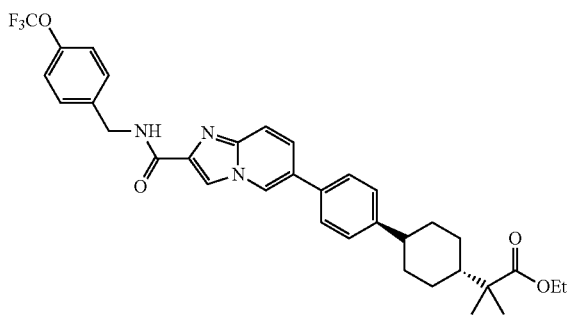

Step A: Ethyl 2-methyl-2-((1r,4r)-4-(4-(2-((4-(trifluoromethoxy)benzyl)carbamoyl)imidazo[1,2-a]pyridin-6-yl)phenyl)cyclohexyl)propanoate The title compound was prepared from Intermediate I and Intermediate LXVI by using procedures analogous to those described for step A of Example 1.

¹H NMR (400 MHz CDCl₃) δ 8.29-8.28 (m, 1H), 8.20 (s, 1H), 7.69 (t, 1H), 7.58 (d, 1H), 7.52 (d, 1H), 7.48 (d, 2H), 7.41 (d, 2H), 7.31 (d, 2H), 7.18 (d, 2H), 7.67 (d, 2H), 4.16 (q, 2H), 2.56-2.49 (m, 1H), 1.98 (d, 2H), 1.78-1.69 (m, 3H), 1.52 (dq, 2H), 1.30-1.23 (m, 5H), 1.16 (s, 6H). MS 608.3 (M+1)⁺.

Step B: 2-Methyl-2-((1r,4r)-4-(4-(2-((4-(trifluoromethoxy)benzyl)carbamoyl)imidazo[1,2-a]pyridin-6-yl)phenyl)cyclohexyl)propanoic acid Compound 66 was prepared by using procedures analogous to those described for step B of Example 1.

¹H NMR (400 MHz DMSO-d₆) δ 12.00 (s, 1H), 9.03 (t, 1H), 8.89-8.88 (m, 1H), 8.33 (s, 1H), 7.68-7.58 (m, 4H), 7.41 (d, 2H), 7.33 (d, 2H), 7.28 (d, 2H), 4.46 (d, 2H), 2.50 (1H, overlapped with DMSO peaks), 1.84 (d, 2H), 1.70-1.59 (m, 3H), 1.50-1.41 (q, 2H), 1.22-1.14 (q, 2H), 1.03 (s, 6H). MS 580.3 (M+1)⁺.

Example 67

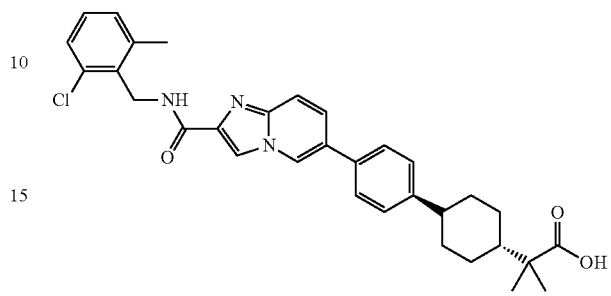

2-((1s,4s)-4-(4-(2-((2-Chloro-6-methylbenzyl)carbamoyl)imidazo[1,2-a]pyridin-6-yl)phenyl)cyclohexyl)-2-methylpropanoic acid—Compound 67

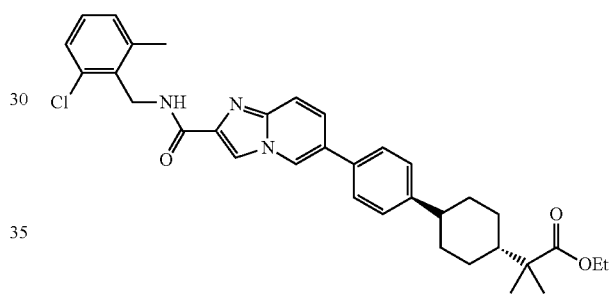

Step A: Ethyl 2-((1s,4s)-4-(4-(2-((2-chloro-6-methylbenzyl)carbamoyl)imidazo[1,2-a]pyridin-6-yl)phenyl)cyclohexyl)-2-methylpropanoate The title compound was prepared from Intermediate XXII and Intermediate LXVI by using procedures analogous to those described for step A of Example 1.

¹H NMR (400 MHz CDCl₃) δ 8.29 (s, 1H), 8.19 (s, 1H), 7.65-7.61 (m, 1H), 7.58-7.51 (m, 1H), 7.47 (d, 2H), 7.32 (d, 2H), 7.27-7.23 (m, 1H), 7.16-7.08 (m, 2H), 4.85 (d, 2H), 4.16 (q, 2H), 2.56-2.46 (m, 4H), 2.20-1.94 (m, 2H), 1.79-1.67 (m, 3H), 1.51 (dq, 2H), 1.31-1.22 (m, 5H), 1.15 (s, 6H).

Step B: 2-((1s,4s)-4-(4-(2-((2-Chloro-6-methylbenzyl)carbamoyl)imidazo[1,2-a]pyridin-6-yl)phenyl)cyclohexyl)-2-methylpropanoic acid Compound 67 was prepared by using procedures analogous to those described for step B of Example 1.

¹H NMR (400 MHz DMSO-d₆) δ 12.08 (s, 1H), 8.89 (s, 1H), 8.35 (s, 1H), 8.16 (t, 1H), 7.69-7.58 (m, 4H), 7.38-7.29 (m, 3H), 7.25-7.16 (m, 3H), 4.64 (d, 2H), 2.47 (s, 3H), 2.50 (1H, overlapped with DMSO peaks), 1.88 (d, 2H), 1.74-1.58 (m, 3H), 1.48 (q, 2H), 1.22 (q, 2H), 1.05 (s, 6H).

Test Example

Test example illustrates the assay used to determine biological activity (inhibition of DGAT1 activity) of compounds according to the present invention. The utility of the compounds of the present invention, and their use in the practice of the invention for the treatment of a disease, condition, or disorder modulated by DGAT1 inhibition, and for the practice of a method for inhibiting DGAT1 activity, can be evidenced by activity in at least one of protocols described in this Example; and also by the ability of compounds of the invention to inhibit DGAT1 activity as shown in Table 1.

The identification of compounds of the present invention as DGAT1 inhibitors was readily achieved using a radiometric and high throughput screening assay.

For this assay, a source of DGAT1 was needed. In that regard, a commercially available plasmid for expression of DGAT1 (e.g., pCMV6-recombinant human DGAT1 plasmid) was transfected for 24 hours in Hep3B cells. After transfection of the plasmid, human DGAT-1 expression was analyzed by Western blot or RT-PCR using whole cell extracts. For establishment of a human DGAT1 overexpressed stable cell line, the cells were grown and maintained in cell culture medium supplemented with high glucose, 10% fetal bovine serum (FBS) and 200 µg/ml G-418, in a 5% $CO_2$ environment for 4 weeks. Cell pellets thus obtained were resuspended in homogenization buffer [250 mM sucrose, 10 mM Tris-HCl (pH 7.4) and 1 mM EDTA], lysed using a homogenization apparatus, and then cell debris was removed by centrifugation at 600×g for 15 minutes. The harvested cell lysate was shown to have human DGAT1 activity.

A second source of DGAT1 activity was human or mouse liver microsomes.

The identification of the inventive compounds as DGAT inhibitors was readily achieved using a high throughput screening radiometric assay. Human and mouse DGAT activity were determined as follows.

Assay buffer [20 mM HEPES (pH 7.4), 100 mM $MgCl_2$ and 0.04% bovine serum albumin (BSA)] containing 500 µM of enzyme substrate (didecanoyl glycerol) and 7.5 µM radiolabeled acyl-CoA substrate ([$^{14}C$]decanoyl-CoA) was added to each well of a phospholipid-coated radiometric assay plate. A small aliquot of cell lysate having human DGAT1 activity (5 µg/well) obtained in above, of human liver microsomes having human DGAT1 activity (5 µg/well), or of mouse liver microsomes having mouse DGAT1 activity (5 µg/well) was added to the assay plate to start the reaction, and the reaction was allowed to proceed for 60 minutes at 25° C. The reaction was terminated upon the addition of an equal volume (100 µL) of isopropanol. The plates were sealed, incubated overnight and counted the next morning on a liquid scintillation counter and luminometer.

DGAT1 catalyzes the transfer of the radiolabelled decanoyl group onto the sn-3 position of didecanoyl glycerol. The resultant radiolabeled tridecanoyl glycerol (tricaprin) preferentially binds to the hydrophobic coating on the phospholipid-coated radiometric assay plate. The proximity of the radiolabeled product to the solid scintillant incorporated into the bottom of the radiometric assay plate induced for release from the scintillant, which was measured in the liquid scintillation counter and luminometer.

Various concentrations (0.0008 µM, 0.004 µM, 0.02 µM, 0.1 µM, 0.5 µM, 2.5 µM and 10.0 µM) of the compounds of Examples were added to individual wells prior to the addition of the cell lysates, or human or mouse liver microsomes. $IC_{50}$ values of the compounds were determined from concentration-dependent inhibition curves by using commercially available software. As shown in Table 1, the almost compounds of the present invention were found to exhibit DGAT1 inhibition with a low $IC_{50}$ value (i.e., in the range of 100 nM or less).

TABLE 1

| | DGAT1 inhibition activity | | |
|---|---|---|---|
| Compound | human $IC_{50}$ (nM) | Source of human DGAT activity* | mouse $IC_{50}$ (nM) |
| 1 | <10 | A | <50 |
| 2 | <10 | A | <200 |
| 3 | <10 | A | <75 |
| 4 | <150 | B | <75 |
| 5 | <100 | B | <125 |
| 6 | <75 | B | <150 |
| 7 | <175 | B | <100 |
| 8 | <125 | B | <50 |
| 9 | <50 | A | <50 |
| 10 | <75 | A | <75 |
| 11 | <50 | A | <75 |
| 12 | <25 | A | <150 |
| 13 | 25.4 | A | 19.0 |
| 14 | 37.9 | A | <1.0 |
| 15 | 17.8 | A | 9.9 |
| 16 | 7.0 | A | 11.7 |
| 17 | 34.5 | A | 12.2 |
| 18 | <10 | A | <1 |
| 19 | <10 | A | <1 |
| 20 | 4.0 | A | 1.2 |
| 21 | <10 | A | <10 |
| 22 | 12.7 | B | 7.6 |
| 23 | <25 | B | <25 |
| 24 | 38.3 | B | 30.1 |
| 25 | 16.8 | B | 5.3 |
| 26 | 29.5 | B | 9.9 |
| 27 | <10 | A | <50 |
| 28 | <10 | A | <50 |
| 29 | <25 | A | <75 |
| 30 | <10 | A | <10 |
| 31 | <50 | B | <100 |
| 32 | <1 | A | <1 |
| 33 | <250 | A | <750 |
| 34 | <150 | A | <450 |
| 35 | <200 | A | <550 |
| 36 | <100 | A | <75 |
| 37 | <10 | A | <50 |
| 38 | <200 | A | <1 |
| 39 | <10 | A | <1 |
| 40 | <1 | A | <50 |
| 41 | <25 | B | <75 |
| 42 | <10 | B | <10 |
| 43 | <10 | B | <10 |
| 44 | <25 | B | <10 |
| 45 | <50 | B | <50 |
| 46 | <1 | B | <50 |
| 47 | <10 | B | <150 |
| 48 | <225 | B | <200 |
| 49 | <10 | B | <25 |
| 50 | <50 | B | <25 |
| 51 | <50 | B | <50 |
| 52 | <10 | B | <10 |
| 53 | <25 | B | <100 |
| 54 | <10 | B | <25 |
| 55 | <10 | B | <25 |
| 56 | <10 | B | <50 |
| 57 | <10 | A | <150 |
| 58 | <100 | A | <325 |
| 59 | <25 | A | <25 |
| 60 | <10 | A | <100 |
| 61 | <10 | A | <10 |
| 62 | <10 | A | <25 |
| 63 | <25 | A | <25 |
| 64 | <10 | A | <10 |
| 65 | <10 | B | <125 |
| 66 | <10 | B | <50 |
| 67 | <25 | B | <50 |

*Source of human DGAT activity:
A = cell lysate from Hep3B cells overexpressing human DGAT1; and
B = human liver microsomes Therefore, the compounds of the present invention (or the pharmaceutical composition comprising such compound)

can be useful in preventing or treating a disease, disorder, or condition modulated by DGAT1 inhibition.

What is claimed is:
1. A compound having a formula (IA), (IB) or (IC), or a pharmaceutically acceptable salt, solvate, or ester thereof:

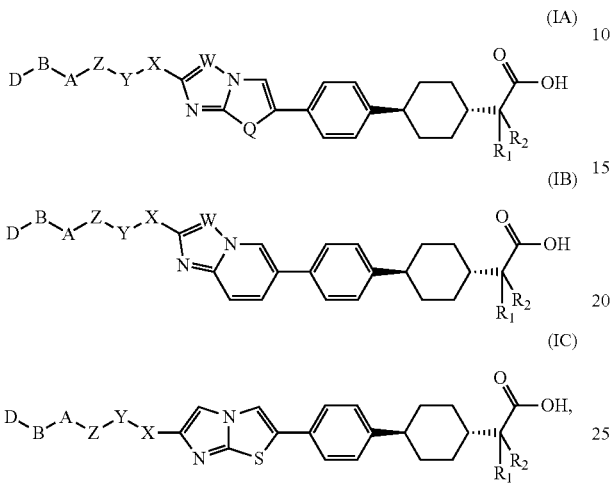

wherein,
Q is S or —CH═CH—;
$R_1$ is H or $(C_1-C_3)$alkyl;
$R_2$ is H or $(C_1-C_3)$alkyl;
W is CH or N;
X is absent, O, $NR_3$, or $CR_4R_5$;
Y is C(O), C(S), S(O), S(O)$_2$, or $CR_4R_5$;
Z is absent, $NR_3$, O, or $CR_4R_5$;
A is absent, $(CR_4R_5)_m$ wherein m is an integer ranging from 1 to 4, —C(CH$_2$CH$_2$)—, C(O), S(O), or S(O)$_2$;
B is absent, $(CR_4R_5)_m$ wherein n is an integer ranging from 1 to 3, C(O), S(O), S(O)$_2$, O, or $NR_3$;
D is H, $(C_1-C_7)$alkyl, $(C_1-C_7)$alkoxy, $(C_1-C_7)$perfluoroalkoxy, $(C_1-C_7)$perfluoroalkyl, $NR_3R_6$ $(C_6-C_{10})$aryl group, a $(C_3-C_{10})$cycloalkyl, or a 3- to 11-membered heterocycle with 1 or 2 rings comprising 1 to 4 endocyclic hetero atoms selected from the group consisting of O, S, and N,
wherein the aryl groups and the said heterocycle present in D are optionally substituted with one or more substituents chosen from a radical G; in which: G, when present, is selected from the group consisting of a halogen atom, hydroxyl group, nitro, cyano, amino, $(C_1-C_7)$alkyl, $(C_1-C_7)$perfluoroalkyl, $(C_1-C_7)$acyl, $(C_1-C_7)$perfluoroacyl, $(C_1-C_7)$perfluoroalkoxy, CF$_3$CH$_2$O—, CF$_3$CH$_2$—, $(C_1-C_7)$alkoxy, $(C_1-C_7)$alkylthio, $(C_1-C_7)$alkylsulfonyl, $(C_1-C_7)$alkylsulfinyl, phenyl, phenoxy, $(\{CH_2\}_p)C(O)OR_3$, $(\{CH_2\}_p)OC(O)R_7$, $(\{CH_2\}_p)NR_3R_6$, $(\{CH_2\}_pR_8)$, $(\{CH_2\}_p)C(O)NR_3R_6$, $(\{CH_2\}_p)C(O)R_8$, $(\{CH_2\}_p)C(O)NR_3R_6$, $(\{CH_2\}_p)OC(O)R_8$, $(\{CH_2\}_p)NR_3C(O)NR_3R_6$, $(\{CH_2\}_p)NR_3C(O)R_8$, $(\{CH_2\}_p)NR_3C(S)NR_3R_6$, $(\{CH_2\}_p)NR_3C(S)R_8$, $(\{CH_2\}_p)NR_3C(O)R_3$, $(\{CH_2\}_p)NR_3C(O)OR_3$, $(\{CH_2\}_p)S(O)_2R_7$, $(\{CH_2\}_p)S(O)R_7$, $(\{CH_2\}_p)NR_3S(O)_2R_7$, $(\{CH_2\}_p)S(O)_2NR_3R_6$, $(\{CH_2\}_p)S(O)_2R_8$, $(CH_2\}_p)NR_3S(O)_2NR_3R_6$, $(\{CH_2\}_p)NR_3S(O)_2R_8$, $(\{CH_2\}_p)NR_3C(NR_3)NR_3R_6$, $(\{CH_2\}_pR_8)$, and a combination thereof (with the proviso that when G is a phenyl or phenoxy, it may option-
ally be substituted with one or more substituents chosen from the radical G other than phenyl or phenoxy); in which:
$R_3$ is H, $(C_1-C_5)$alkyl or $(C_3-C_{10})$cycloalkyl;
$R_4$ and $R_5$ being each independently hydrogen, or $(C_1-C_5)$ alkyl;
$R_6$ is H, $(C_1-C_5)$alkyl or $(C_1-C_{10})$cycloalkyl;
$R_7$ is $(C_1-C_5)$alkyl or $(C_3-C_{10})$cycloalkyl;
$R_8$ is a 3- to 10-membered heterocycle with 1 or 2 rings comprising 1 to 4 endocyclic hetero atoms selected from the group consisting of O, S and N;
p is an integer ranging from 0 to 5; and
q is an integer ranging from 1 to 5.
2. A compound having a formula (ID), (IE) or (IF), or a pharmaceutically acceptable salt, solvate, or ester thereof:

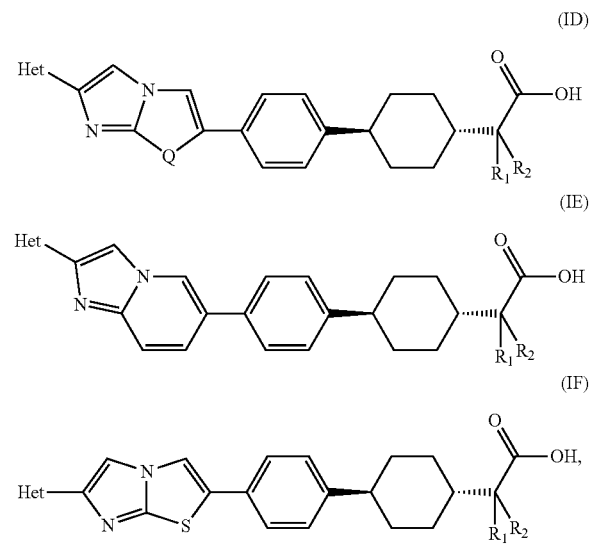

Wherein,
Q is S or —CH═CH—;
$R_1$ is H or $(C_1-C_3)$alkyl;
$R_2$ is H or $(C_1-C_3)$alkyl; and
Het is a Het is a 3- to 11-membered heterocycle with 1 or 2 rings comprising 1 to 4 endocyclic hetero atoms selected from the group consisting of O, S and N, wherein said heterocycle is optionally substituted with one or more substituents chosen from a radical G; in which: G is selected from the group consisting of a halogen atom, hydroxyl group, nitro, cyano, amino, $(C_1-C_7)$alkyl, $(C_1-C_7)$perfluoroalkyl, $(C_1-C_7)$acyl, $(C_1-C_7)$perfluoroacyl, $(C_1-C_7)$perfluoroalkoxy, CF$_3$CH$_2$O—, CF$_3$CH$_2$—, $(C_1-C_7)$alkoxy, $(C_1-C_7)$alkylthio, $(C_1-C_7)$alkylsulfonyl, $(C_1-C_7)$alkylsulfinyl, phenyl, phenoxy, $(\{CH_2\}_p)C(O)OR_3$, $\{CH_2\}_p)OC(O)R_7$, $(\{CH_2\}_p)NR_3R_6$, $(\{CH_2\}_pR_8)$, $(\{CH_2\}_p)C(O)NR_3R_6$, $(\{CH_2\}_p)C(O)R_8$, $(\{CH_2\}_p)OC(O)NR_3R_6$, $(\{CH_2\}_p)OC(O)R_8$, $(\{CH_2\}_p)NR_3C(O)NR_3R_6$, $(\{CH_2\}_p)NR_3C(O)R_8$, $(\{CH_2\}_p)NR_3C(S)NR_3R_6$, $(\{CH_2\}_p)NR_3C(S)R_8$, $(\{CH_2\}_p)NR_3C(O)R_3$, $(\{CH_2\}_p)NR_3C(O)OR_3$, $(\{CH_2\}_p)S(O)_2R_7$, $(\{CH_2\}_p)S(O)R_7$, $(\{CH_2\}_p)NR_3S(O)_2R_7$, $(\{CH_2\}_p)S(O)_2NR_3R_6$, $(\{CH_2\}_p)S(O)_2R_8$, $(\{CH_2\}_p)NR_3S(O)_2NR_3R_6$, $(\{CH_2\}_p)NR_3S(O)_2R_8$, $(\{CH_2\}_p)NR_3C(NR_3)NR_3R_6$, $(\{CH_2\}_pR_8)$, and a combination thereof (with the proviso that when G is a phenyl or phenoxy, it may optionally be substituted with one or more substituents chosen from the radical G other than phenyl or phenoxy); in which:

R$_3$ is H, (C$_1$-C$_5$)alkyl or (C$_3$-C$_{10}$)cycloalkyl;
R$_4$ and R$_5$ being each independently hydrogen, or (C$_1$-C$_5$) alkyl;
R$_6$ is H, (C$_1$-C$_5$)alkyl or (C$_3$-C$_{10}$)cycloalkyl;
R$_7$ is (C$_1$-C$_5$)alkyl or (C$_3$-C$_{10}$)cycloalkyl;
R$_8$ is a 3- to 10-membered heterocycle with 1 or 2 rings comprising 1 to 4 endocyclic hetero atoms selected from the group consisting of O, S and N;
p is an integer ranging from 0 to 5; and
q is an integer ranging from 1 to 5.

3. The compound of claim 1, wherein
R$_1$ and R$_2$ being each independently hydrogen;
W is CH or N;
X is absent;
Y is C(O);
Z is absent or NH;
A is absent, (C$_1$-C$_3$)alkyl, —C(CH$_2$CH$_2$)—, CH(CH$_3$)— or C(CH$_3$)$_2$—;
B is absent, (C$_1$-C$_3$)alkyl, —C(CH$_2$CH$_2$)—, CH(CH$_3$)— or C(CH$_3$)$_2$—; and
D is phenyl; phenyl substituted with one or more substituents chosen from a radical G selected from the group consisting of halogen, hydroxy, (C$_1$-C$_7$)alkyl, (C$_1$-C$_7$) alkoxy, CF$_3$CH$_2$O—, CF$_3$CH$_2$— and phenoxy substituted with halogen; benzo[d][1,3]dioxole; or 3,4-dihydro-2H-benzo[b][1,4]dioxepin.

4. The compound of claim 1 or 2, which is selected from the group consisting of:

1) 2-((1r,4r)-4-(4-(2-((4-(Trifluoromethoxy)benzyl)carbamoyl)imidazo[1,2-a]pyridin-6-yl)phenyl)cyclohexyl)acetic acid;
2) 2-((1r,4r)-4-(4-(2((4-(Trifluoromethyl)phenyl)carbamoyl)imidazo[1,2-a]pyridin-6-yl)phenyl)-cyclohexyl) acetic acid;
3) 2-((1r,4r)-4-(4-(2-((4-(Trifluoromethoxy)phenyl)carbamoyl)imidazo[1,2-a]pyridin-6-yl)-phenyl)cyclohexyl)acetic acid;
4) 2-((1r,4r)-4-(4-(2-((4-(Trifluoromethyl)benzyl)carbamoyl)imidazo[1,2-a]pyridin-6-yl)-phenyl)cyclohexyl)acetic acid;
5) 2-((1r,4r)-4-(4-(2-((3-Trifluoromethoxyl)phenyl)carbamoyl)imidazo[1,2a]pyridin-6-yl)-phenyl)cyclohexyl)acetic acid;
6) 2-((1r,4r)-4-(4-(2-((3-(Trifluoromethyl)phenyl)carbamoyl)imidazo[1,2-a]pyridin-6-yl)-phenyl)cyclohexyl)acetic acid;
7) 2-((1r,4r)-4-(4-(2-((3-(Trifluoromethoxy)benzyl)carbamoyl)imidazo[1,2-a]pyridin-6-yl)-phenyl)cyclohexyl)acetic acid;
8) 2-((1r,4r)-4-(4-(2-((4-tert-Butyl)benzyl)carbamoy)imidazo[1,2-a]pyridin-6-yl)phenyl)-cyclohexyl)acetic acid;
9) 2-((1r,4r)-4-(4-(2-((2-Fluoro-5-(trifluoromethoxy)benzyl)carbamoyl)imidazo[1,2-a]pyridin-6-yl)phenyl)cyclohexyl)acetic acid;
10) 2-((1r,4r)-4-(4-(2-((4-Fluoro-3-(trifluoromethoxy) benzyl)carbamoyl)imidazo[1,2-a]pyridin-6-yl)phenyl) cyclohexyl)acetic acid;
11) 2-((1r,4r)-4-(4-(2-((3-Fluoro-4-(trifluoromethyl)benzyl)carbamoyl)imidazo[1,2-a]pyridin-6-yl)phenyl)cyclohexyl)acetic acid;
12) 2-((1r,4r)-4-(4-(2-((4-Methoxybenzyl)carbamoyl) imidazo[1,2-a]pyridin-6-yl)phenyl)cyclo-hexypacctic acid;
13) 2-((1r,4r)-4-(4-(2-((3-Chloro-4-fluorophenyl)carbamoyl)imidazo[1,2-a]pyridin-6-yl)-phenyl)cyclohexypacetic acid;
14) 2-((1r,4r)-4-(4-(2-((Benzo[d][1,3]dioxo$_1$-5-ylmethyl)carbamoyl)imidazo[1,2-a]pyridin-6-yl)phenyl)cyclohexyl)acetic acid;
15) 2-((1r,4r)-4-(4-(2-((3,4-Dichlorophenyl)carbamoyl) imidazo[1,2-a]pyridin-6-yl)phenyl)-cyclohexyl)acetic acid;
16) 2-((1r,4r)-4-(4-(2-((3-Chlorophenyl)carbamoyl)imidazo[1,2-a]pyridin-6-yl)phenyl)cyclo-hexyl)acetic acid;
17) 2-((1r,4r)-4-(4-(2-((3-Chloro-4-fluorobenzyl)carbamoyl)imidazo[1,2-a]pyridin-6-yl)-phenyl)cyclohexyl) acetic acid;
18) 2-((1r,4r)-4-(4-(2-((2-Methoxy-5-(trifluoromethoxy) benzyl)carbamoyl)imidazo[1,2-a]pyridin-6-yl)phenyl) cyclohexyl)acetic acid;
19) 2-((1r,4r)-4-(4-(2-((4-Isopropylbenzyl)carbamoyl) imidazo[1,2-a]pyridin-6-yl)phenyl)cyclo-hexyl)acetic acid;
20) 2-((1r,4r)-4-(4-(2-((2-4-Fluorophenyl)propan-2-yl) carbamoyl)imidazo[1,2-a]pyridin-6-yl)phenyl)cyclohexyl)acetic acid;
21) 2-((1r,4r)-4-(4-(2-((1-(2,5-Difluorophenyl)cyclopropyl)carbamoyl)imidazo[1,2-a]pyridin-6-yl)phenyl)cyclohexyl)acetic acid;
22) 2-((1r,4r)-4-(4-(2-((2-Chloro-6-methylbenzyl)carbamoyl)imidazo[1,2-a]pyridin-6-yl)-phenyl)cyclohexyl)acetic acid;
23) 2-((1r,4r)-4-(4-(2-((3,4-Dimethoxybenzyl)carbamoyl) imidazo[1,2-a]pyridin-6-yl)phenyl)-cyclohexyl)acetic acid;
24) (R,S)-2-((1r,4r-4-(4-(2-((1-Phenylethyl)carbamoyl) imidazo[1,2-a]pyridin-6-yl)phenyl)cyclo-hexyl)acetic acid;
25) 2-((1r,4r)-4-(4-(2-((4-(4-Fluorophenoxy)benzyl)carbamoyl)imidazo[1,2-a]pyridin-6-yl)-phenyl)cyclohexyl)acetic acid;
26) 2-((1r,4r)-4-(4-(2-(((3,4-Dihydro-2H-benzo[b][1,4] dioxepin-7-yl)methyl)carbamoyl)-imidazo[1,2-a]pyridin-6-yl)phenyl)cyclohexyl)acetic acid;
27) 2-((1r,4r)-4-(4-(2-((2-Chloro-6-fluorobenzyl)carbamoyl)imidazo[1,2-a]pyridin-6-yl)-phenyl)cyclohexyl) acetic acid;
28) 2-((1r,4r)-4-(4-(2-((2-6-Dichlorobenzyl)carbamoyl) imidazo[1,2-a]pyridin-6-yl)phenyl)-cyclohexyl)acetic acid;
29) 2-((1r,4r)-4-(4-(2-((2,6-Difluorobenzyl)carbamoyl) imidazo[1,2-a]pyridin-6-yl)phenyl)-cyclohexyl)acetic acid;
30) 2-((1r,4r)-4-(4-(2-((2-Chloro-6-(trifluoromethyl)benzyl)carbamoyl)imidazo[1,2-a]pyridin-6-yl)phenyl)cyclohexyl)acetic acid;
31) 2-((1r,4r)-4-(4-(2-(Benzylcarbamoyl)imidazo[1,2-a] pyridin-6-yl)phenyl)-cyclohexyl)acetic acid;
32) 2-((1r,4r)-4-(4-(2-(o-Tolylcarbamoyl)imidazo[1,2-a] pyridin-6-yl)phenyl)-cyclohexyl)acetic acid;
33) 2-((1r,4r)-4-(4-(2-(4-Fluoro-2(trifluoromethyl)phenyl)carbamoyl)imidazo[1,2-a]pyridin-6-yl)phenyl)-cyclohexyl)acetic acid;
34) 2-((1r,4r)-4-(4-(2-((2-(Trifluoromethyl)phenyl)carbamoyl)imidazo[1,2-a]pyridin-6-yl)phenyl)-cyclohexyl)acetic acid;
35) 2-((1r,4r)-4-(4-(2-((2-Fluorophenyl)carbamoyl)imidazo[1,2-a]pyridin-6-yl)phenyl)-cyclohexyl)acetic acid;
36) 2-((1r,4r)-4-(4-(2-((2-Methoxphenyl)carbamoyl)imidazo[1,2-a]pyridin-6-yl)phenyl)-cyclohexyl)acetic acid;

37) 2-((1r,4r)-4-(4-(2-((2-Methylbenzyl)carbamoyl)imidazo[1,2-a]pyridin-6-yl)phenyl)-cyclohexyl)acetic acid;
38) 2-((1r,4r)-4-(4-(2-((2,6-Dimethylphenyl)carbamoyl)imidazo[1,2-a]pyridin-6-yl)phenyl)-cyclohexyl)acetic acid;
39) 2-((1r,4r)-4-(4-(2-((2,5-Difluorophenyl)carbamoyl)imidazo[1,2-a]pyridin-6-yl)phenyl)-cyclohexyl)acetic acid;
40) 2-((1r,4r)-4-(4-(2-((3,4,5-Trifluorophenyl)carbamoyl)imidazo[1,2-a]pyridin-6-yl)phenyl)-cyclohexyl)acetic acid;
41) 2-((1r,4r)-4-(4-(2-((2-Methoxybenzyl)carbamoyl)imidazo[1,2-a]pyridin-6-yl)phenyl)-cyclohexyl)acetic acid;
42) 2-((1s,4s)-4-(4-(2-((4-chloro-2,6-difluorobenzyl)carbamoyl)imidazo[1,2-a]pyridin-6-yl)phenyl)-cyclohexyl)acetic acid;
43) 2-((1s,4s)-4-(4-(2-((2,4-Dichloro-6-methylbenzyl)carbamoyl)imidazo[1,2-a]pyridin-6-yl)phenyl)-cyclohexyl)acetic acid;
44) 2-((1s,4s)-4-(4-(2-((2,4,6-Trimethylbenzyl)carbamoyl)imidazo[1,2-a]pyridin-6-yl)phenyl)-cyclohexyl)acetic acid;
45) 2-((1s,4s)-4-(4-(2-((4-Methylbenzyl)carbamoyl)-[1,2,4]triazolo[1,5-a]pyridin-6-yl)phenyl)-cyclohexyl)acetic acid;
46) 2-((1r,4r)-4-(4-(6-((4-(tert-Butyl)benzyl)carbamoyl)imidazo[1,2-b]pyridin-6-yl)phenyl)-cyclohexyl)acetic acid;
47) 2-((1r,4r)-4-(4-(6-((3-Chlorophenyl)carbamoyl)imidazo[1,2-b]pyridin-6-yl)phenyl)-cyclohexyl)acetic acid;
48) 2-((1r,4r)-4-(4-(6-((3-Chloro-4-(trifluoromethoxy)benzyl)carbamoyl)imidazo[2,1-b]thiazol-2phenyl)-cyclohexyl)acetic acid;
47) 2-((1r,4r)-4-(4-(6-((3-Chlorophenyl)carbamoyl)imidazo[2,1-b]thiazol-2-yl)phenyl)cyclo-hexyl)acetic acid;
48) 2-((1r,4r)-4-(4-(6-((3-Chloro-4-(trifluoromethoxy)benzyl)carbamoyl)imidazo[2,1-b]thiazol-2-yl)phyenyl)cyclohexyl)acetic acid;
49) 2-((1r,4r)-4-(4-(6-((3-Chloro-4-fluorobenzyl)carbamoyl)imidazo[2,1-b]thiazol-2-yl)phyenyl)-cyclohexyl) acetic acid;
50) 2-((1r,4r)-4-(4-(6-((3-(Trifluoromethoxy)benzyl)carbamoyl)imidazo[2,1-b]thiazol-2-yl)phyenyl)cyclohexyl)acetic acid;
51) 2-((1r,4r)-4-(4-(6-((2-Fluoro-5-(trifluoromethoxy)benzyl)carbamoyl)imidazo[2,1-b]thiazol-2-yl)phyenyl)cyclohexyl)acetic acid;
52) 2-((1r,4r)-4-(4-(6-((3-(Trifluoromethoxy)phenyl)carbamoyl)imidazo[2,1-b]thiazol-2-yl)phyenyl)cyclohexyl)acetic acid;
53) 2-((1r,4r)-4-(4-(6-((4-Isopropylbenzyl)carbamoyl)imidazo[2,1-b]thiazol-2-yl)phyenyl)cyclohexyl)acetic acid;
54) 2-((1r,4r)-4-(4-(6-((1-(2,5-Difluorophenyl)carbamoyl)imidazo[2,1-b]thiazol-2-yl)phyenyl)cyclohexyl) acetic acid;
55) 2-((1r,4r)-4-(4-(6-((2-Methoxy-5-(trifluoromethoxy)benzyl)carbamoyl)imidazo[2,1-b]thiazol-2-yl)phyenyl)cyclohexyl)acetic acid;
56) 2-((1r,4r)-4-(4-(6-((4-(Trifluoromethoxy)benzyl)carbamoyl)imidazo[2,1-b]thiazol-2-yl)phyenyl)cyclohexyl)acetic acid;
57) 2-((1r,4r)-4-(4-(6-((4-Methoxybenzyl)carbamoyl)imidazo[2,1-b]thiazol-2-yl)phyenyl)cyclo-hexyl)acetic acid;
58) 2-((1r,4r)-4-(4-(6-((Benzo[d][1,3]dioxol-5-ylmethyl)carbamoyl)imidazo[2,1-b]thiazol-2-yl)phyenyl)cyclohexyl)acetic acid;
59) 2-((1r,4r)-4-(4-(6-((4-Fluoro-3-(trifluoromethoxy)benzyl)carbamoyl)imidazo[2,1-b]thiazol-2-yl)phyenyl)cyclohexyl)acetic acid;
60) 2-((1r,4r)-4-(4-(6-((3-Chloro-4-fluorophenyl)carbamoyl)imidazo[2,1-b]thiazol-2-yl)phyenyl)cyclohexyl) acetic acid;
61) 2-((1r,4r)-4-(4-(6-((2,6-dichlorobenzyl)carbamoyl)imidazo[2,1-b]thiazol-2-yl)phyenyl)cyclohexyl)acetic acid;
62) 2-((1r,4r)-4-(4-(6-((2-chloro-6-fluorobenzyl)carbamoyl)imidazo[2,1-b]thiazol-2-yl)phyenyl)cyclohexyl) acetic acid;
63) 2-((1r,4r)-4-(4-(6-((2,6-difluorobenzyl)carbamoyl)imidazo[2,1-b]thiazol-2-yl)phyenyl)cyclohexyl)acetic acid;
64) 2-((1r,4r)-4-(4-(6-((4-chloro-2,6-difluorobenzyl)carbamoyl)imidazo[2,1-b]thiazol-2-yl)phyenyl)cyclohexyl)acetic acid;
65) 2-((1r,4r)-4-(4-(2-(Benzylcarbamoyl)imidazo[1,2-a]pyridin-6-yl)phyenyl)cyclohexyl)-2-methylpropanoic acid;
66) 2-Methyl-2-((1r,4r)-4-(4-(2-(trifluoromethoxy)benzyl)carbamoyl)imidazo[1,2-a]pyridin-6-yl)phyenyl)cyclohexyl) propanoic acid;
67) 2-((1s,4s)-4-(4-(2-((2-Chloro-6-methylbenzyl)carbamoyl)imidazo[1,2-a]pyridin-6-yl)phyenyl)cyclohexyl)-2-methylpropanoic acid.

5. A pharmaceutical composition for therapeutically treating a disease, disorder or condition modulated by DGAT1 inhibition, which comprises the compound or its pharmaceutically acceptable salt, solvate, or ester of claim 1,
wherein the disease, disorder or condition modulated by DGAT1 inhibition is selected from the group consisting of obesity; type 2 diabetes; complications associated with type 2 diabetes selected from the group consisting of angina, atherosclerosis, high blood pressure, neuropathy, nephropathy, diabetic retinopathy, skin ulcers, osteoporosis, vascular dementia and hearing impairment; heart disease associated with increased triglyceride levels, hypertension, metabolic syndrome, polycystic ovary syndrome and dyslipidemia; non-alcoholic fatty liver disease; and a combination thereof.

6. The pharmaceutical composition of claim 5, which further comprises at least one additional pharmaceutical agent selected from the group consisting of an anti-obesity agent, an anti-diabetic agent, an anti-dyslipidemia agent, and an anti-hypertensive agent.

7. A method for therapeutically treating a disease, disorder or condition modulated by DGAT1 inhibition in an individual comprising the step of administering the compound or its pharmaceutically acceptable salt, solvate, or ester of claim 1 to the individual in need thereof,
wherein the disease, disorder or condition modulated by DGAT1 inhibition is selected from the group consisting of obesity; type 2 diabetes; complications associated with type 2 diabetes selected from the group consisting of angina, atherosclerosis, high blood pressure, neuropathy, nephropathy, diabetic retinopathy, skin ulcers, osteoporosis, vascular dementia and hearing impairment; heart disease associated with increased triglyceride levels, hypertension, metabolic syndrome, polycystic ovary syndrome and dyslipidemia; non-alcoholic fatty liver disease; and a combination thereof.

8. The method of claim 7, which comprises the step of administering a medically effective amount of two pharmaceutical compositions comprising
   (i) a first composition comprising the compound, or its pharmaceutically acceptable salt, solvate, or ester of claim 1 and a pharmaceutically acceptable carrier; and
   (ii) a second composition comprising at least one additional pharmaceutical agent selected from the group consisting of an anti-obesity agent, an anti-diabetic agent, an anti-dyslipidemia agent, and an anti-hypertensive agent to the individual in need thereof.

9. The method of claim 8, wherein the first composition and the second composition are administered simultaneously, or sequentially and in any order.

* * * * *